United States Patent [19]
Morris et al.

[11] Patent Number: 6,124,306
[45] Date of Patent: Sep. 26, 2000

[54] THIOALKYL ALPHA SUBSTITUTED PYRIMIDINE COMPOUNDS

[75] Inventors: Joel Morris; Wade J. Adams, both of Kalamazoo; Janice M. Friis, Mattawan; Donn G. Wishka, Kalamazoo, all of Mich.

[73] Assignee: Pharmacia & Upjohn Company, Kalamazoo, Mich.

[21] Appl. No.: 09/157,975

[22] Filed: Sep. 21, 1998

Related U.S. Application Data

[63] Continuation of application No. PCT/US98/18507, Sep. 21, 1998
[60] Provisional application No. 60/059,656, Sep. 25, 1997.

[51] Int. Cl.$^7$ ............... C07D 239/34; C07D 403/12; A61K 31/505
[52] U.S. Cl. ............ 514/274; 514/232.5; 514/232.2; 514/233.8; 514/234.2; 514/234.5; 514/235.8; 514/252.14; 514/227.8; 514/228.2; 514/228.5; 514/252.16; 514/252.17; 514/256; 514/257; 514/258; 514/259; 514/261; 514/266; 544/315; 544/264; 544/278; 544/316; 544/296; 544/255; 544/317; 544/256; 544/262; 544/318; 544/295; 544/121; 544/253; 544/122; 544/115; 544/116; 544/123; 544/80; 544/117; 544/58.6; 544/81; 544/118; 544/90; 544/61
[58] Field of Search .................... 544/315, 316, 544/317, 318, 295, 122, 123, 58.6, 60, 61; 514/227.8, 228.2, 228.5, 235.8, 274, 232.5, 232.2, 233.8, 234.2, 234.5, 252.14, 256

[56] References Cited

U.S. PATENT DOCUMENTS

| 4,724,232 | 2/1988 | Rideout et al. ............... 514/50 |
| 5,025,016 | 6/1991 | Ahrens et al. ............ 514/274 |

FOREIGN PATENT DOCUMENTS

| 694 538 | 1/1996 | European Pat. Off. . |
| 477 778 | 4/1996 | European Pat. Off. . |
| 300 230 | 5/1992 | Germany . |
| 744867 | 10/1952 | United Kingdom . |
| WO 96/35678 | 11/1996 | WIPO . |

OTHER PUBLICATIONS

Schickaneder, H. et al., *2-[3-Pyridinylmethyl)thio]pyrimidine Derivatives: New Bronchosecretolytic Agents*, J. Med. Chem., 30:547–551 (1987).
Baker, B.R. et al., *Puromycin. Synthetic Studies. VI. Analogs of 6–Dimethylaminopurine*, J. Org. Chem., 19:1793–1801 (1954).
Science, 234:661–662 (1986).
Curran, J.W. et al., *The Epidemiology of AIDS: Current Status and Future Prospects*, Science, 229:1352–1357 (1985).
Pauwels, R. et al., *Potent and selective inhibition of HIV–1 replication in vitro by a novel series of TIBO derivatives*, Nature, 343:470–474 (1990).
Koppel, H.C., et al., *Pyrimidines. V. Analogs of 2–(o–Chlorobenzylthio)–4–dimethylamino–5–methylpyrimidine*, J. Org. Chem., 27:181–185 (1962).
Ward, A.D. and B.R. Baker, *Irreversible Enzyme Inhibitors. 200. Active–Site–Directed Inhibitors of Deoxycytidine Kinase*, J. Med. Chem., 20:88–92 (1977).
Budesinsky, Z. et al., *5–(3–Iodopropargyloxy)Pyrimidines as Effective Fungistatics*, Collect. Czech. Chem. Comm., 40:1078–1088 (1975);—CA 83:114326e.
Koppel, H.C., et al., *Pyrimidines. IV. Aziridinylpyrimidines*, J. Org. Chem., 26:1884–1890 (1961).
Tjarks, W. and D. Gabel, *Boron–Containing Thiouracil Derivatives for Neutron–Capture Therapy of Melanoma*, J. Med. Chem. 34:315–319 (1991).
Kropf, H. et al., *4–t–Butylperoxypyrimidine, 2–4–Di–t–butylperoxy– und 4,6–Di–t–butylperoxypyrimidine*, Synthesis, 397–400 (1981).
Vainilavicius, P. et al., *Hydrazones based on 5–ethyl–6–methyl–2–thiouracil*, Chemical Abstracts, vol. 80 (21) Abstract No. 120861e [1974].
Hashizume, K. and S. Inoue, *Model experiments on surugatoxin synthesis. III. Synthesis of 2,4–dibenzyloxy–6–ethylsulfonyl–5–nitropyrimidine*, Chemical Abstracts vol. 104 (3), Abstract No. 19434g [1986].
Chebib, M. and R.J. Quinn, *1–Phenylpyrazolo[3,4–d]pyrimidines as Adenosine Antagonists: the Effects of Substituents at C4 and C6*, Bioorganic & Medicinal Chemistry, 5(2):311–322 (1997).
Althaus, I.W., et al., *The Benzylthio–Pyrimidine U–31,355, a Potent Inhibitor of HIV–1 Reverse Transcriptase*, Biochemical Pharmacology, 51:743–750 (1996).
Merluzzi, V.J. et al., *Inhibition of HIV–1 Replication by a Nonnucleoside Reverse Trancriptase Inhibitor*, Science, 250:1411 (1990).

Primary Examiner—John M. Ford
Attorney, Agent, or Firm—Andrew M. Solomon

[57] ABSTRACT

The subject invention relates to pyrimidine-thioalkyl and alkylether compounds of Formula I

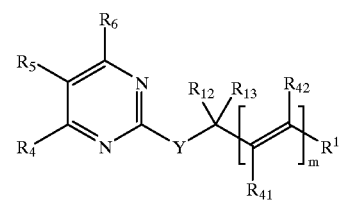

and pyrimidine-thioalkyl and alkylethers of Formula I, where $R_4$ is selected from the group consisting of —H or —$NR_{15}R_{16}$ where $R_{15}$ is —H and $R_{16}$ is —H, $C_1$–$C_6$ alkyl, —$NH_2$ or $R_{15}$ and $R_{16}$ taken together with the —N form 1-pyrrolidino, 1-morpholino or 1-piperidino; and $R_6$ is —S—$C_{1-6}$ alkyl (preferably —$SCH_3$);

The compounds of Formula I are useful in the treatment of individuals who are HIV positive.

24 Claims, No Drawings

THIOALKYL ALPHA SUBSTITUTED PYRIMIDINE COMPOUNDS

CROSS-REFERENCE TO RELATED APPLICATIONS

This application claims the benefit of the following provisional application: U.S. Ser. No. 60/059,656, filed Sep. 25, 1997, which is a con of PCT/US98/18507 filed Sep. 21, 1998.

BACKGROUND OF THE INVENTION

1. Field of Invention

The 6-thioalkyl pyrimidine-2-thioalkyl and alkylether derivatives of Formula I are useful in the treatment of individuals who are HIV positive, whether or not they show AIDS symptoms at the present time. The 6-thioalkyl pyrimidine-2-thioalkyl and alkylether derivatives of Formula I are useful in the preparation of the pyrimidine-thioalkyl and alkylether derivatives of Formula I.

2. Description of the Related Art

U.S. Pat. No. 5,025,016 (and EP 124 630) pyrimidine-thioalkyl pyridine derivatives corresponding to the general formula

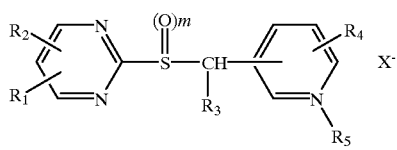

in which $R_1$ to $R_4$, independently of one another, represent hydrogen, lower alkyl, halogen, amino or hydroxy groups, $R_5$ represents a free electron pair or a lower alkyl group, a halogen atom, m has the value 0 or 1, the pyrimidine-thioalkyl group being bonded in the 2-, 3- or 4-position of the pyridine ring, and to therapeutically compatible acid addition salts thereof. The compounds allegedly exhibit surprisingly improved bronchosecretolytic and myucolytic activity as well as having been found to show antiphlogistic activity.

J. Med Chem. 1987, 30, 547–551 describes various 2-[(pyridinylmethyl)thiol-pyrimidine derivatives and the influence thereof on bronchosecretolytic properties in the phenol red screening model of the mouse in comparison to the known drug ambroxol.

EP 477 778 (Derwent 92-106190/14) describes various benzene, pyridine and pyrimidine derivatives as ACAT enzyme inhibitors, for treating arteriosclerosis, and cerebrovascular disease.

J. Org. Chem, 1954, 19, 1793–1801 describes pyrimidine derivatives, including 2-benzylmercapto-4-amino-6-pyrimidinol, 2-benzylmercapto-4-amino-6-chloropyrimidine, 2-benzylmercapto-4-amino-6-diethylaminopyrimidine as well as analogs of 6-dimethylaminopurine.

British Patent 744,867 (CA 51:2063i) describes various 2-R'-S-6-RR'N-substituted 4-aminopyrimidines.

An estimated one to one and one-half million people in the United States are infected with a human retrovirus, the human immunodeficiency virus type I (HIV-1) which is the etiological agent of acquired immunodeficiency syndrome, AIDS, see Science, 661–662 (1986). Of those infected, an estimated two hundred and fifty thousand people will develop AIDS in the next five years, see Science, 1352–1357 (1985). On Mar. 20, 1987, the FDA approved the use of the compound, AZT (zidovudine), to treat AIDS patients with a recent initial episode of *pneumocystis carinii* pneumonia, AIDS patients with conditions other than *pneumocystis carinii* pneumonia or patients infected with the virus with an absolute CD4 lymphocyte count of less than 200/mm$^3$ in the peripheral blood. AZT is a known inhibitor of viral reverse transcriptase, an enzyme necessary for human immunodeficiency virus replication.

U.S. Pat. No. 4,724,232 claims a method of treating humans having acquired immunodeficiency syndrome utilizing 3'-azido-3'-deoxy-thymidine (azidothymidine, AZT).

It is known in the art that certain antibiotics and polyanionic dyes inhibit retrovirus reverse transcriptase.

Many publications have reported the ability of various sulfated compounds to inhibit virus replication, including HIV.

Nature 343, 470 (1990) and Science 250, 1411 (1990) disclose potent benzodiazepin type reverse transcriptase inhibitors. The compounds of the present invention are not benzodiazepin type compounds.

J. Org. Chem. 1962, 27, 181–185 describes various 2-benzylthio pyrimidine derivatives, including 4-chloro-5-methyl-2-[(phenylmethyl)thio]-pyrimidine, 4-chloro-5-methyl-2-[[(2,4-dichloro-phenyl)methyl]thio]-pyrimidine, 4-chloro-5-methyl-2-[[(2-chloro-phenyl)methyl]thio]-pyrimidine, and 4-chloro-5-methyl-2-[[(4-chloro-phenyl)methyl]thio]-pyrimidine and their activity as antitumor compounds in screens against SA-180, CA 755, and L-1210 tumor systems.

J. Med. Chem. 1977, 20, 88–92 describes 2-alkoxy and 2-alkylthio-4-amino pyrimidines, including 2-[(phenylmethyl)thio]4-pyrimidinamine, 2-[[(4-chlorophenyl)methyl]thio]-4-pyrimidinamine, 2-[(3-pyridinylmethyl)thio]4-pyrimidinamine, and 2-(phenylmethoxy)-4-pyrimidinamine, and their activity as inhibitors of deoxycytidine kinase.

Collect. Czech. Chem. Comm. 1975, 40, 1078–1088 (CA 83:114326e) describes 5-(3-iodopropargyloxy)pyrimidines as effective fungistatics.

Synthesis 1981, 397–400 describes peroxypyrimidines.

J. Org. Chem. 1961, 26, 1884 describes the synthesis of aziridinyl pyrimidines as analogs of methioprim.

J. Med. Chem. 1991, 34, 315–319 describes derivatives of thiouracil which have dihydroxyboryl group at the C-5 position. These compounds are useful for B neutron-capture therapy of malignant melanoma.

WO 96/35678 (published Nov. 14, 1996) discloses various alpha-substituted pyrimidine-2-thioalkyl and alkylether compounds of Formula A

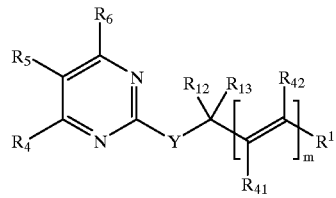

wherein
  $R_4$ is selected from the group consisting of —H, —OH, halo or —NR$_{15}$R$_{16}$ where R is —H and R$_{16}$ is —H, $C_1$–$C_6$ alkyl, —NH$_2$ or R$_{15}$ and R$_{16}$ taken together with the —N form 1-pyrrolidino, 4-morpholino or 1-piperidino;
  $R_5$ is selected from the group consisting of —H, —C$_2$H$_4$OH, —C$_2$H$_4$—O-TBDMS, halo, —C$_3$–C$_6$ cycloalkyl, $C_1$–$C_3$ alkoxy, —$CH_2CH_2Cl$ or $C_1$–$C_4$ alkyl, with the proviso that $R_5$ is not isobutyl;

or $R_4$ and $R_5$ are taken together to form a five or six-membered saturated or unsaturated ring which together with the pyrimidine ring form the group consisting of 7H-pyrrolo[2,3-d]pyrimidine, 5,6-dihydro-7H-pyrrolo[2,3-d]pyrimidine, furo[2,3-pyrimidine, 5,6-dihydro-furo[2,3-d]pyrimidine, thieno[2,3-d]pyrimidine, 5,6-dihydro-thieno[2,3-d]pyrimidine, 1H-pyrazolo[3,4-d]pyrimidine, 1H-purine, pyrimido[4,5-d]pyrimidine, pteridine, pyrido[2,3-dipyrimidine, or quinazoline, where the unsaturated ring may be optionally substituted with 1, 2 or 3, $C_1$–$C_6$ alkyl, $C_1$–$C_6$ alkoxy, —OH, —$CH_2OH$, or —$(CH_2)_n$—$N(R_{31})(R_{32})$, —$C_3$–$C_8$ cycloalkyl, —$CF_3$, -halo, —$CO_2(R_{31})$, —$CON(R_{31})(R_{32})$, —$CO(R_{31})$, —$(CH_2)_nN(R_{31})(CO(R_{33}))$, —$(CH_2)_nN(R_{31})(SO_2(R_{33}))$, and the saturated ring may be optionally substituted with 1, 2 or 3, —$C_1$–$C_6$ alkyl, —$C_1$–$C_6$ alkoxy, —OH, —$CH_2OH$, or —$(CH_2)_n$—$N(R_{31})(R_{32})$ or one oxo (=O); and $R_6$ is selected from the group consisting of —H, —OH, halo (preferably —Cl), —CN, —$CF_3$, —$CO_2(R_{61})$, —$C(O)R_{61}$ or —$C(O)N(R_{61})(R_{62})$ where $R_{61}$ and $R_{62}$ are the same or different and are selected from
—H,
$C_1$–$C_6$ alkyl,
phenyl optionally substituted with 1, 2, or 3-halo, $C_1$–$C_6$ alkyl, $C_1$–$C_6$ alkoxy, —$CF_3$, —OH, —CN, or where $R_{61}$ and $R_{62}$ taken together with the attached nitrogen to form a ring selected from -pyrrolidinyl, -piperidinyl, -4-morpholinyl, -4-thiomorpholinyl, -4-piperazinyl, or -4-($C_1$–$C_6$ alkyl)piperazinyl;

with the overall proviso that $R_4$ and $R_6$ are not both —H; and with the further proviso that and $R_{12}$ and $R_{13}$ are not both —H except when $R_6$ is selected from —CN, —$F_3$, —$CO_2(R_{61})$, —$C(O)R_{61}$ or —$C(O)N(R_{61})(R_{62})$, or $R_1$ is selected from —$CO_2R_{53}$ or —$C(O)N(R_{54})(R_{55})$.

SUMMARY OF INVENTION

Disclosed are 6-thioalkyl pyrimidine-2-thioalkyl and alkylether compounds of Formula I

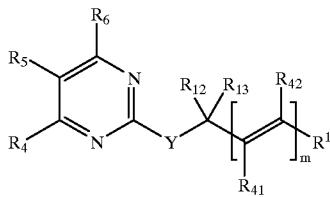

and therapeutically/pharmaceutically compatible acid addition salts thereof.

The compounds corresponding to Formula I may exist in various tautomeric formulas, and are included within the scope of Formula I.

DETAILED DESCRIPTION OF THE INVENTION

Disclosed are 6-thioalkyl pyrimidine-2-thioalkyl and alkylether compounds of Formula I

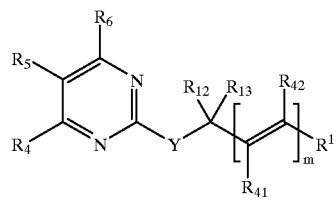

where m is 0 or 1;

$R^1$ is selected from the group consisting of —C≡CH, —$CO_2R_{53}$, —$CONR_{54}R_{55}$,

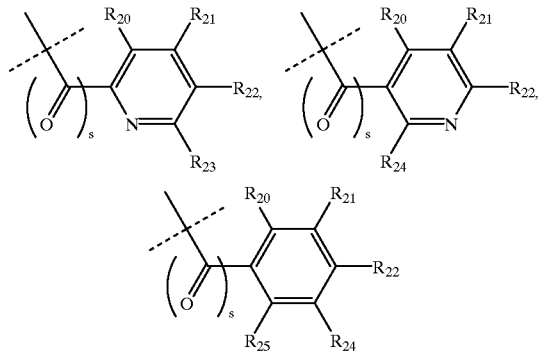

where s is 0 or 1 (preferably 0) and $R_{20}$, $R_{21}$, $R_{22}$, $R_{23}$, $R_{24}$, and $R_{25}$ are the same or different and are selected from —H, $C_1$–$C_6$ alkyl, $C_1$–$C_6$ alkenyl, $C_1$–$C_6$ alkoxy, $C_1$–$C_6$ alkylthio, —$C_3$–$C_8$ cycloalkyl, —$CF_3$, —$NO_2$, -halo, —OH, —CN, phenyl, phenylthio, -styryl, —$CO_2(R_{31})$, —$CON(R_{31})(R_{32})$, —$CO(R_{31})$, —$(CH_2)_n$—$N(R_{31})(R_{32})$, —$C(OH)(R_{31})(R_{33})$, —$(CH_2)_nN(R_{31})(CO(R_{33}))$, $(CH_2)_nN(R_{31})(SO_2(R_{33}))$, or where $R_{20}$ and $R_{21}$, or $R_{21}$ and $R_{22}$, or $R_{22}$ and $R_{23}$ are taken together to form a five or six-membered saturated or unsaturated ring containing 0 or 1 oxygen, nitrogen or sulfur, where the unsaturated ring may be optionally substituted with 1, 2 or 3, $C_1$–$C_6$ alkyl, $C_1$–$C_6$ alkoxy, —OH, —$CH_2OH$, $(CH_2)_n$—$N(R_{31})(R_{32})$, —$C_3$–$C_8$ cycloalkyl, —$CF_3$, -halo, $CO_2(R_{31})$, —$CON(R_{31})(R_{32})$, —$CO(R_{31})$, —$(CH_2)_nN(R_{31})(CO(R_{33}))$, —$(CH_2)_nN(R_{31})(SO_2(R_{33}))$, —CN, —$CH_2CF_3$ or —$CH(CF_3)_2$, or phenyl, and the saturated ring may be optionally substituted with 1, 2 or 3, —$C_1$–$C_6$ alkyl, —$C_1$–$C_6$ alkoxy, —OH, —$CH_2OH$ or —$(CH_2)_n$—$N(R_{31})(R_{32})$ or one oxo (=O);

where n is 0–3 and $R_{31}$, $R_{32}$, and $R_{33}$ are the same or different and are selected from
—H,
$C_1$–$C_6$ alkyl,
phenyl optionally substituted with 1, 2, or 3-halo, $C_1$–$C_6$ alkyl, $C_1$–$C_6$ alkoxy, —$CF_3$, —OH or —CN,
or where $R_{31}$ and $R_{32}$ taken together with the attached nitrogen to form a ring selected from -pyrrolidinyl, -piperidinyl, -4-morpholinyl, -4-thiomorpholinyl, -4-piperazinyl, -4-(1-$C_1$–$C_6$alkyl)piperazinyl,
or a member selected from the group consisting of:
1-cyclohexenyl, 2-pyrimidinyl, 4-pyrimidinyl, 5-pyrimidinyl, 2-imidazolyl, 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 1-methylimidazol-2-yl, quinoxalin-2-yl, piperon-5-yl, 4,7-dichlorobenzoxazol-2-yl, 4,6-dimethyl-pyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S-4-isopropenylcyclohexen-1-yl or 4-dihydronaphth-2-yl; where $R_{53}$ is selected from the group consisting of —H, $C_1$-$C_6$alkyl, $C_3$-$C_6$cycloalkyl, phenyl (optionally substituted with 1, 2, or 3-halo, $C_1$-$C_6$ alkyl, $C_1$-$C_6$ alkoxy, —$CF_3$, —OH, —CN), or a five or six-membered unsaturated ring containing 0 or 1 oxygen, nitrogen or sulfur, where the unsaturated ring may be optionally substituted with —H, $C_1$-$C_6$ alkyl, $C_1$-$C_6$ alkoxy, —OH, —$CH_2OH$, or —$(CH_2)_n$—$N(R_{31})$ $(R_{32})$; where $R_{54}$ and $R_{55}$ being the same or different are selected from —H. $C_1$-$C_6$ alkyl, allyl, or phenyl (optionally substituted with 1, 2, or 3-halo, $C_1$-$C_6$ alkyl, $C_1$-$C_6$ alkoxy or —$CF_3$), or taken together with the attached nitrogen to form a ring selected from -pyrrolidinyl, -piperidinyl, -4-morpholinyl, -4-thiomorpholinyl, -4-piperazinyl, -4-(1-$C_1$-$C_6$alkyl)piperazinyl;

$R_{41}$ and $R_{42}$, being the same or different, are selected from the group consisting of —H and $C_1$-$C_4$ alkyl;

$R_{12}$ is selected from the group consisting of —H, $C_1$-$C_6$ alkyl, —$C_3$-$C_6$ cycloalkyl, —CN, —$C(O)NH_2$, —$C(O)N(C_1$-$C_6$alkyl)($C_1$-$C_6$alkyl), —$CO_2H$, —$CO_2$ ($C_1$-$C_6$alkyl), —$CH_2OH$, —$CH_2NH_2$ or —$CF_3$;

$R_{13}$ is selected from the group consisting of —H, $C_1$-$C_6$ alkyl or —$CF_3$;

Y is selected from —S—, —S(O)—, —S(O)$_2$, or —O—;

$R_4$ is selected from the group consisting of —H, —OH, halo or —$NR_{15}R_{16}$ where $R_{15}$ is —H and $R_{16}$ is —H, $C_1$-$C_6$ alkyl, —$NH_2$ or $R_{15}$ and $R_{16}$ taken together with the —N form 1-pyrrolidino, 4-morpholino or 1-piperidino;

$R_5$ is selected from the group consisting of —H, —$C_2H_4OH$, —$C_2H_4$—O-TBDMS, halo, —$C_3$-$C_6$ cycloalkyl, $C_1$-$C_3$ alkoxy, —$CH_2CH_2Cl$ or $C_1$-$C_4$ alkyl, with the proviso that $R_5$ is not isobutyl;

or $R_4$ and $R_5$ are taken together to form a five or six-membered saturated or unsaturated ring which together with the pyrimidine ring form the group consisting of 7H-pyrrolo[2,3-d]pyrimidine, 5,6-dihydro-7H-pyrrolo[2,3-d]pyrimidine, furo[2,3-d]pyrimidine, 5,6-dihydro-furo[2,3-d]pyrimidine, thieno[2,3-d]pyrimidine, 5,6-dihydro-thieno[2,3-d]pyrimidine, 1H-pyrazolo [3,4-d]pyrimidine, 1H-purine, pyrimido [4,5-d]pyrimidine, pteridine, pyrido[2,3-d]pyrimidine, or quinazoline, where the unsaturated ring may be optionally substituted with 1, 2 or 3, $C_1$-$C_6$ alkyl, $C_1$-$C_6$ alkoxy, —OH, —$CH_2OH$, or —$(CH_2)_n$—N $(R_{31})(R_{32})$, —$C_3$-$C_8$ cycloalkyl, —$CF_3$, -halo, —$CO_2$ $(R_{31})$, —$CON(R_{31})(R_{32})$, —$CO(R_{31})$, —$(CH_2)_nN(R_{31})$ $(CO(R_{33}))$, $(CH_2)_nN(R_{31})$ $(SO_2(R_{33}))$, and the saturated ring may be optionally substituted with 1, 2 or 3, —$C_1$-$C_6$ alkyl, —$C_1$-$C_6$ alkoxy, —OH, —$CH_2OH$ or —$(CH_2)_n$—$N(R_{31})(R_{32})$ or one oxo (=O); and $R_6$ is —S—$C_{1-6}$ alkyl (preferably —S—$CH_3$);

pharmaceutically acceptable salts, hydrates, N-oxides and solvates thereof.

An embodiment of the present invention are compounds of Formula I where $R_{12}$ and $R_{13}$ are not both —H.

An embodiment of the present invention are 6-thioalkyl pyrimidine-2-thioalkyl and alklyether anti-AIDS compounds of Formula I where $R_4$ is selected from the group consisting of —H or —$NR_{15}R_{16}$ where $R_{15}$ is —H and $R_{16}$ is —H, $C_1$-$C_6$ alkyl, —$NH_2$ or $R_{15}$ and $R_{16}$ taken together with the —N form 1-pyrrolidino, 4-morpholino or 1-piperidino; and $R_6$ is —S—$C_1$-$C_6$ alkyl (preferably —S—$CH_3$).

The compounds of Formula I can be prepared in accordance with the procedures disclosed in WO 96/35678 as well as U.S. patent application Ser. No. 08/436,708; filed May 8, 1995, both of which are incorporated herein by reference.

An embodiment of the present invention are compounds of Formula I where Y is —O—.

A preferred embodiment of the present invention are compounds of Formula I where s is 0 and Y is selected from the group consisting of —S—, —S(O)— or —S(O)$_2$; more preferably Y is —S—.

A preferred embodiment of the present invention are compounds of Formula I where s is 0 and Y is selected from the group consisting of —S—, —S(O)— or —S(O)$_2$ (more preferably Y is —S—); and with the proviso that $R_{12}$ and $R_{13}$ are not both —H.

$R_4$ is preferably —$NH_2$.

m is preferably 0.

$R_6$ is preferably —S—$CH_3$.

$R_{41}$ and $R_{42}$ are preferably —H.

$R_{12}$ is preferably —$CH_3$.

$R_{13}$ is preferably —H.

$R^1$ is preferably selected from

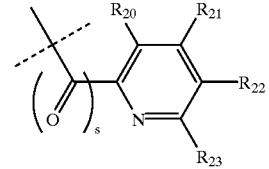

more preferably a member selected from the group consisting of:

3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyrindinyl, 1-(5,6-dihydro)-2H-2-pyrindinyl, 2-(5,6-dihydro)-1H-1-pyrindinyl, 3-(5,6-dihydro)-1H-1-pyrindinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl, 5-1H-pyrrolo[2,3-c]pyridinyl, 6-1H-pyrrolo[3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2,3-dihydro)-1H-pyrrolo[3,2-c]pyridinyl, 7-(2,3-dihydro)-1H-pyrrolo[2,3-c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3,4-b]pyridinyl, 6-1,7-naphthyridinyl, 6-2,7-naphthyridinyl, 7-2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)-benzofuranyl, 7-(2,3-dihydro)-benzofuranyl, 4-(1,3-dihydro)-isobenzofuran, 5-(1,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3-dihydro)-1H-indolyl, 6-(2,3-dihydro)-1H-indolyl, 7-(2,3-dihydro)-1H-indolyl, 4-(1,3-dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1-benzopyranyl, 7-(3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl, 5-thieno[2,3-c]pyridinyl, 6-thieno[3,2-c]pyridinyl, 4-thieno[3,2-c]pyridinyl, 7-thieno[2,3-c]pyridinyl, 6-thieno[2,3-b]pyridinyl, 5-thieno[3,2-b]pyridinyl, 5-(2,3-dihydro)-thieno[2,3-c]pyridinyl, 6-(2,3-dihydro)-thieno[3,2-c]pyridinyl, 4-(2,3-dihydro)-thieno[3,2-c]pyridinyl, 7-(2,3-dihydro)-thieno[2,3-c]pyridinyl, 6-(2,3-dihydro)-thieno[2,3-b]pyridinyl, 5-(2,3-dihydro)-thieno[3,2-b]pyridinyl, 6-(1,3-dihydro)-thieno[3,4-c]pyridinyl, 4-(1,3-dihydro)-thieno[3,4-c]pyridinyl, 2-(5,7-dihydro)-thieno[3,4-b]pyridinyl, 6-(3,4-dihydro)-2H-thiopyrano[2,3-c]pyridinyl, 6-(3,4-dihydro)-1H-thiopyrano[3,4-c]pyridinyl, 7-(3,4-dihydro)-1H-thiopyrano[4,3-c]pyridinyl, 7-(3,4-dihydro)-2H-thiopyrano[3,2-c]pyridinyl, 5-(3,4-dihydro)-2H-thiopyrano[3,2-c]pyridinyl, 5-(3,4-dihydro)-1H-thiopyrano[4,3-c]pyridinyl, 8-(3,4-dihydro)-1H-thiopyrano[3,4-c]pyridinyl, 8-(3,4-dihydro)-2H-thiopyrano[2,3-c]pyridinyl, 7-(3,4-dihydro)-2H-thiopyrano[2,3-b]pyridinyl, 2-(5,6-dihydro)-1H-thiopyrano[3,4-b]pyridinyl, 2-(5,6-dihydro)-2H-thiopyrano[4,3-b]pyridinyl, 6-(3,4-dihydro)-2H-thiopyrano[3,2-b]pyridinyl, 5-benzo[b]thiophenyl, 4-benzo[b]thiophenyl, 6-benzo[b]thiophenyl, 7-benzo[b]thiophenyl, 5-(2,3-dihydro)-benzo[b]thiophenyl, 4-(2,3-dihydro)-benzo[b]thiophenyl, 6-(2,3-dihydro)-benzo[b]thiophenyl, 7-(2,3-dihydro)-benzo[b]thiophenyl, 4-(1,3-dihydro)-benzo[c]thiophenyl, 5-(1,3-dihydro)-benzo[c]thiophenyl, 5-(3,4-dihydro)-1H-2-benzothiopyranyl, 6-(3,4-dihydro)-1H-2-benzothiopyranyl, 7-(3,4-dihydro)-1H-2-benzothiopyranyl, 8-(3,4-dihydro)-1H-2-benzothiopyranyl, 5-(3,4-dihydro)-2H-1-benzothiopyranyl, 6-(3,4-dihydro)-2H-1-benzothiopyranyl, 7-(3,4-dihydro)-2H-1-benzothiopyranyl, or 8-(3,4-dihydro)-2H-1-benzothiopyranyl; wherein such member is optionally substituted as described above;

most preferably a member selected from the group consisting of:

3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyrindinyl, 1-(5,6-dihydro)-2H-2-pyrindinyl, 2-(5,6-dihydro)-1H-1-pyrindinyl, 3-(5,6-dihydro)-1H-1-pyrindinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, or 6-(3,4-dihydro)-2H-pyrano[3,2-b]pyridinyl; wherein such member is optionally substituted as described above.

Illustrative $R_1$ members include:

phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro; 2- or 3-pyridinyl optionally substituted with $C_1$–$C_6$ alkyl, $C_1$–$C_6$ alkenyl, $C_1$–$C_6$ alkoxy, $C_1$–$C_6$ alkylthio, —$C_3$–$C_8$ cycloalkyl, —$CF_3$, —$NO_2$, -halo, —OH, —CN, phenyl, phenylthio, -styryl, —$CO_2(R_{31})$, —CON($R_{31}$)($R_{32}$), —CO($R_{31}$), —($CH_2$)$_n$—N($R_{31}$)($R_{32}$), —C(OH)($R_{31}$)($R_{33}$), ($CH_2$)$_n$N($R_{31}$)(CO($R_{33}$)), ($CH_2$)$_n$N($R_{31}$)($SO_2$($R_{33}$)); naphthyl optionally substituted with one or 2 $C_1$–$C_4$ alkyl, $C_1$–$C_3$ alkoxy, halo, trifluoromethyl, $C_2$–$C_6$ dialkylamino, $C_1$–$C_3$ alkylthio or nitro; —C≡CH; as well as 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyrindinyl, 1-(5,6-dihydro)-2H-2-pyrindinyl, 2-(5,6-dihydro)-1H-1-pyrindinyl, 3-(5,6-dihydro)-1H-1-pyrindinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-2H-pyrano[4,3-c]pyridinyl, 7-(3,4-dihydro)-2H-pyrano[3,2-c]pyridinyl, 5-(3,4-dihydro)-1H-pyrano[3,2-c]pyridinyl, 5-(3,4-dihydro)-2H-pyrano[3,2-c]pyridinyl, 5-(3,4-dihydro)-2H-pyrano[3,4-c]pyridinyl, 5-(3,4-dihydro)-2H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl, 5-1H-pyrrolo[2,3-c]pyridinyl, 6-1H-pyrrolo[3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2,3-dihydro)-1H-pyrrolo[3,2-c]pyridinyl, 7-(2,3-dihydro)-1H-pyrrolo[2,3-c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3,4-b]pyridinyl, 6-1,7-naphthyridinyl, 6-2,7-naphthyridinyl, 7-2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)-benzofuranyl, 7-(2,3-dihydro)-benzofuranyl, 4-(1,3-dihydro)-isobenzofuran, 5-(1,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3-dihydro)-1H-indolyl, 6-(2,3-dihydro)-1H-indolyl, 7-(2,3-dihydro)-1H-indolyl, 4-(1,3-dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1-benzopyranyl, 7-(3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl, 5-thieno[2,3-c]pyridinyl, 6-thieno[3,2-c]pyridinyl, 4-thieno[3,2-c]pyridinyl, 7-thieno[2,3-c]pyridinyl, 6-thieno[2,3-b]pyridinyl, 5-thieno[3,2-b]pyridinyl, 5-(2,3-dihydro)-thieno[2,3-c]pyridinyl, 6-(2,3-dihydro)-thieno[3,2-c]pyridinyl, 4-(2,3-dihydro)-thieno[3,2-c]pyridinyl, 7-(2,3-dihydro)-thieno[2,3-c]pyridinyl, 6-(2,3-dihydro)-thieno[2,3-b]pyridinyl, 5-(2,3-dihydro)-thieno[3,2-b]pyridinyl, 6-(1,3-dihydro)-thieno[3,4-c]pyridinyl, 4-(1,3-dihydro)-thieno[3,4-c]pyridinyl, 2-(5,7-dihydro)-thieno[3,4-b]pyridinyl, 6-(3,4-dihydro)-2H-thiopyrano[2,3-c]pyridinyl, 6-(3,4-dihydro)-1H-thiopyrano[3,4-c]pyridinyl, 7-(3,4-dihydro)-1H-thiopyrano[4,3-c]pyridinyl, 7-(3,4-dihydro)-2H-thiopyrano[3,2-c]pyridinyl, 5-(3,4-dihydro)-2H-thiopyrano[3,2-c]pyridinyl, 5-(3,4-dihydro)-1H-thiopyrano[4,3-c]pyridinyl, 8-(3,4-dihydro)-1H-thiopyrano[3,4-c]pyridinyl, 8-(3,4-dihydro)-2H-thiopyrano[2,3-c]pyridinyl, 7-(3,4-dihydro)-2H-thiopyrano[2,3-b]pyridinyl, 2-(5,6-dihydro)-1H-thiopyrano[3,4-b]pyridinyl, 2-(5,6-dihydro)-2H-thiopyrano[4,3-b]pyridinyl, 6-(3,4-dihydro)-2H-thiopyrano[3,2-b]pyridinyl, 5-benzo[b]thiophenyl, 4-benzo[b]thiophenyl, 6-benzo[b]thiophenyl, 7-benzo[b]thiophenyl, 5-(2,3-dihydro)-benzo[b]thiophenyl, 4-(2,3-dihydro)-benzo[b]thiophenyl, 6-(2,3-dihydro)-benzo[b]thiophenyl, 7-(2,3-dihydro)-benzo[b]thiophenyl, 4-(1,3-dihydro)-benzo[c]thiophenyl, 5-(1,3-dihydro)-benzo[c]thiophenyl, 5-(3,4-dihydro)-1H-2-benzothiopyranyl, 6-(3,4-dihydro)-1H-2-benzothiopyranyl, 7-(3,4-dihydro)-1H-2-benzothiopyranyl, 8-(3,4-dihydro)-1H-2-benzothiopyranyl, 5-(3,4-dihydro)-2H-1-benzothiopyranyl, 6-(3,4-dihydro)-2H-1-benzothiopyranyl, 7-(3,4-dihydro)-2H-1-benzothiopyranyl, 8-(3,4-dihydro)-2H-1-benzothiopyranyl, or a member selected from the group consisting of:

4-quinolinyl, 5-quinolinyl, 6-quinolinyl, 7-quinolinyl, 8-quinolinyl, 1-cyclohexenyl, 2-pyrimidinyl, 4-pyrimidinyl, 5-pyrimidinyl, 2-imidazolyl, 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3- dihydrobenzopyran-5-yl, 2,3-dihydrobenzofuran-2-yl, 1-methylimidazol-2-yl, quinoxalin-2-yl, isoquinolin-3-yl, piperon-5-yl, 4,7-dichlorobenzoxazol-2-yl, 4,6-dimethylpyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S-4-isopropenyl-cyclohexen-1-yl and 4-dihydronaphth-2-yl.

Preferred thioalkyl-substituted pyrimidine-2-thioalkyl and alkylether anti-AIDS compounds of Formula I include compounds where Y is S, and m is 0.

Additional preferred thioalkyl substituted pyrimidine-2-thioalkyl and alkylether anti-AIDS compounds of Formula I include compounds where Y is S, m is 0, $R_{12}$ is $CH_3$ and $R_{13}$ is —H.

Additional preferred thio-substituted pyrimidine-2-thioalkyl and alkylether anti-AIDS compounds of Formula I include compounds where Y is S, m is 0, $R_{12}$ is $CH_3$, $R_{13}$ is —H, $R_4$ is $NH_2$, $R_5$ is —H and $R_6$ is —S—$CH_3$.

More preferred thioalkyl substituted pyrimidine-2-thioalkyl and alkylether anti-AIDS compounds of Formula I include compounds where Y is S, m is 0, s is 0, $R_{12}$ is $CH_3$, $R_{13}$ is —H, $R_4$ is NH, $R_5$ is —H, $R_6$ is —S—$CH_3$, and $R_1$ is selected from the group consisting of

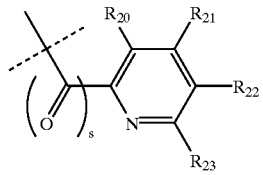

Most preferred thioalkyl substituted pyrimidine-2-thioalkyl and alkylether anti-AIDS compounds of Formula I include compounds where Y is S, m is 0, s is 0, $R_{12}$ is $CH_3$, $R_{13}$ is —H, $R_4$ is $NH_2$, $R_5$ is —H, $R_6$ is —S—$CH_3$, and $R_1$ is selected from the group consisting of 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyrindinyl, 1-(5,6-dihydro)-2H-2-pyrindinyl, 2-(5,6-dihydro)-1H-1-pyrindinyl, 3-(5,6-dihydro)-1H-1-pyrindinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-1H-pyrano[4,3-b]pyridinyl, 6-(3,4-dihydro)-2H-pyrano[3,2-b]pyridinyl, 5-1H-pyrrolo[2,3-c]pyridinyl, 6-1H-pyrrolo[3,2-c]pyridinyl, 4-2H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2, 3-dihydro)-1H-pyrrolo[3,2-c]pyridinyl, 7-(2,3-dihydro)-1H-pyrrolo[2,3-c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3,4-b]pyridinyl, 6-1,7-naphthyridinyl, 6-2,7-naphthyridinyl, 7-2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-2H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)-benzofuranyl, 7-(2,3-dihydro)-benzofuranyl, 4-(2,3-dihydro)-isobenzofuran, 5-(1,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3-dihydro)-1H-indolyl, 6-(2,3-dihydro)-1H-indolyl, 7-(2,3-dihydro)-1H-indolyl, 4-(1,3-dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1-benzopyranyl, 7-(3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl, 5-thieno[2,3-c]pyridinyl, 6-thieno[3,2-c]pyridinyl, 4-thieno[3,2-c]pyridinyl, 7-thieno[2,3-c]pyridinyl, 6-thieno[2,3-b]pyridinyl, 5-thieno[3,2-b]pyridinyl, 5-(2,3-dihydro)-thieno[2,3-c]pyridinyl, 6-(2,3-dihydro)-thieno[3,2-c]pyridinyl, 4-(2,3-dihydro)-thieno[3,2-c]pyridinyl, 7-(2,3-dihydro)-thieno[2,3-c]pyridinyl, 6-(2,3-dihydro)-thieno[2,3-b]pyridinyl, 5-(2,3-dihydro)-thieno[3,2-b]pyridinyl, 6-(1,3-dihydro)-thieno[3,4-c]pyridinyl, 4-(1,3-dihydro)-thieno[3,4-c]pyridinyl, 2-(5,7-dihydro)-thieno[3,4-b]pyridinyl, 6-(3,4-dihydro)-2H-thiopyrano[2,3-c]pyridinyl, 6-(3,4-dihydro)-1H-thiopyrano[3,4-c]pyridinyl, 7-(3,4-dihydro)-1H-thiopyrano[4,3-c]pyridinyl, 7-(3,4-dihydro)-2H-thiopyrano[3,2-c]pyridinyl, 5-(3,4-dihydro)-2H-thiopyrano[3,2-c]pyridinyl, 5-(3,4-dihydro)-1H-thiopyrano[4,3-c]pyridinyl, 8-(3,4-dihydro)-1H-thiopyrano[3,4-c]pyridinyl, 8-(3,4-dihydro)-2H-thiopyrano[2,3-c]pyridinyl, 7-(3,4-dihydro)-2H-thiopyrano[2,3-b]pyridinyl, 2-(5,6-dihydro)-1H-thiopyrano[3,4-b]pyridinyl, 2-(5,6-dihydro)-2H-thiopyrano[4,3-b]pyridinyl, 6-(3,4-dihydro)-2H-thiopyrano[3,2-b]pyridinyl, 5-benzo[b]thiophenyl, 4-benzo[b]thiophenyl, 6-benzo[b]thiophenyl, 7-benzo[b]thiophenyl, 5-(2,3-dihydro)-benzo[b]thiophenyl, 4-(2,3-dihydro)-benzo[b]thiophenyl, 6-(2,3-dihydro)-benzo[b]thiophenyl, 7-(2,3-dihydro)-benzo[b]thiophenyl, 4-(1,3-dihydro)-benzo[c]thiophenyl, 5-(1,3-dihydro)-benzo[c]thiophenyl, 5-(3,4-dihydro)-1H-2-benzothiopyranyl, 6-(3,4- dihydro)-1H-2-benzothiopyranyl, 7-(3,4-dihydro)-1H-2-benzothiopyranyl, 8-(3,4-dihydro)-1H-2-benzothiopyranyl, 5-(3,4-dihydro)-2H-1-benzothiopyranyl, 6-(3,4-dihydro)-2H-1-benzothiopyranyl, 7-(3,4-dihydro)-2H-1-benzothiopyranyl, 8-(3,4-dihydro)-2H-1-benzothiopyranyl; most preferably a member selected from the group consisting of:

3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyrindinyl, 1-(5,6-dihydro)-2H-2-pyrindinyl, 2-(5,6-dihydro)-1H-1-pyrindinyl, 3-(5,6-dihydro)-1H-1-pyrindinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl.

The 6-thioalkyl pyrimidine-2-thioalkyl compounds of Formula I are generally and most often prepared by contacting a 6-chloro pyrimidine-2-thioalkyl compound of Formula I with an appropriate alkyl thiolate, e.g. sodium thiomethoxide, sodium thioethoxide, etc. (Chart A).

Alternatively, the 6-thioalkyl pyrimidine 2-thioalkyl compounds of Formula I are prepared by contacting a 6-thioalkyl-2-thiopyrimidine with an appropriate alkylating agent, e.g. mesylate or halide. The corresponding 6-thioalkyl-2-thiopyrimidine is prepared by, for example, by reacting 4-amino-6-chloro-2-(4-methoxybenzyl)thiopyrimidine with an appropriate alkyl thiolate followed by deprotection with an appropriate reagent such as methane sulfonic acid. (Chart B).

When $R_{12}$ and $R_{13}$ are different, the compounds of Formula I are drawn as the racemic mixture and include the R and S isomers, which can be resolved from the racemic mixture by HPLC using a chiral column, such as Chiralcel OD-H, eluting with an appropriate solvent mixture, such as isopropanol/hexane. The R and S isomers of Formula I (when $R_{12}$ and $R_{13}$ are different) can be prepared from an appropriate chiral halide (or mesylate) II (see Chart B). The appropriate chiral halide (or mesylate) II is prepared from a chiral alcohol IV. The appropriate chiral alcohol IV can be prepared from the appropriate ketone V using a chiral reducing agent, such as (+) or (−)-diisopinocampheylchloroborane or other chiral reducing agents known in the art. The appropriate chiral alcohol IV is also obtained from the resolution of the racemic alcohol VII via the enzymatic hydrolysis of the appropriate racemic acetate VI with the appropriate enzyme, such as PS-30 amano lipase or L1754 Type VII from *candidae cylindracea* or other enzymes known in the art. The appropriate chiral alcohol IV is also obtained from the resolution of the racemic alcohol VII via the enzymatic esterification (such as acetylation or butyration) of the racemic alcohol VII (to give chiral VIII) using the appropriate enzyme, such as porcine pancreatic lipase type II, or other enzymes known in the art.

The 6-thioalkyl substituted pyrimidine-2-thioalkyl and alkylether compounds of Formula I include the compounds of EXAMPLES 1–304. Preferred are the anti-AIDS compounds of EXAMPLES 230, 231, 233, 234, 237, 238, 239, 240, 241, 242, 243, 246, 247, 248, 249, 250, 251, 252, 256, 269, 270, 271, 272, 273, 277, 194, 199, 203, 207, 282, 283, 284, 285, 286, 287, 289, 290, 297, 1 and preferably 237, 238, 239, 246, 289, 290, 297, 1 and more preferably 290, 297, 1 and salts thereof (e.g. 302, 306 and 301).

The pyrimidine-thioalkyl and alkylether compounds of Formula I form acid addition salts; such as mesylate, hydrochloride, hydrobromide, hydroiodide, sulfate, phosphate, acetate, propionate, lactate, maleate, malate, succinate, tartrate, and the like. Some of the variable substituents are acids and as such form base addition salts when reacted with bases of sufficient strength. The pharmaceutically acceptable salts include both inorganic and organic bases. The preferred pharmaceutically acceptable salts include salts of the following bases, for example, hydroxide, ammonia, tromethamine (THAM), 2-amino-2-(hydroxymethyl)-1,3-propanediol. Suitable cations include, for example, sodium, potassium, calcium and magnesium.

The pyrimidine-thioalkyl and alkylether anti-AIDS compounds of Formula I are useful as inhibitors of viral reverse transcriptase, an enzyme necessary for human immunodeficiency virus replication and therefore would be useful in the treatment of such diseases as AIDS.

The term human retrovirus (HRV) indicates human immunodeficiency virus type I, or strains thereof apparent to one skilled in the art, which belong to the same viral families and which create similar physiological effects in humans as various human retroviruses.

Patients to be treated would include those individuals (1) infected with one or more than one strain of a human retrovirus as determined by the presence of either measurable viral antibody or antigen in the serum and (2) having either a symptomatic AIDS defining infection such as (a) disseminated histoplasmosis, (b) isopsoriasis, (c) bronchial and pulmonary candidiasis including pneumocystic pneumonia (d) non—Hodgkin's lymphoma or (e) Kaposi's sarcoma and being less than sixty years old; or having an absolute CD4 lymphocyte count of less than 200/mm$^3$ in the peripheral blood.

The compounds of Formula I can be given orally. Suitable dosage forms include tablets, capsules, suspensions, solutions and elixirs. An effective amount is from about 0.1 to about 500 mg/kg/day. A typical unit dose for a 70 kg human would be from about 10 mg to about 2000 mg, preferably about 100 mg to about 1000 mg taken one to six times per day.

The exact dosage and frequency of administration depends on the particular compound of Formula I used, the particular condition being treated, the severity of the condition being treated, the age, weight, general physical condition of the particular patient, other medication the individual may be taking as is well known to those skilled in the art and can be more accurately determined by measuring the blood level or concentration of the compounds of Formula I in the patient's blood and/or the patient's response to the particular condition being treated.

Patients who are HIV positive but asymptomatic would typically be treated with lower oral doses (about 0.2 to about 100 mg/kg/day. ARC (AIDS-related complex) and AIDS patients would typically be treated with higher oral doses (about 1 to about 500 mg/kg/day).

The pyrimidine-thioalkyl and alkylether anti-AIDS compounds of Formula I of this invention can be used in conjunction with (or sequentially with) other antiviral agents such as AZT, ddl, ddC, 3TC, d4T, with non-nucleoside anti-AIDS agents such as those disclosed in Ser. No. 08/400, 095 Case 4788.1 CP, filed Mar. 7, 1995, International Publication No. WO91/09849, published Jul. 11, 1991, and International Publication No. WO93/01181, published Jan. 21, 1993, and with protease inhibitors.

The utility of the pyrimidine-thioalkyl and alkylether anti-AIDS compounds of Formula I of this invention can be determined by their ability to inhibit viral reverse transcriptase, an enzyme essential for human immunodeficiency virus replication. This enzyme has characteristics which differentiate it from other known cellular polymerases and it is a unique enzyme which is not found in uninfected cells. Viral reverse transcriptase (Wild Type) is found in extracts from bacterial clones prepared according to the procedure described in AIDS Virus Reverse Transcriptase defined by high level expression in *Escherichia coli*, EMBO J. 6:3133–3137 (1987). P236L viral reverse transcriptase is obtained by PNAS 90: 4713–4717 (1993). Inhibition of this enzyme is determined in a cell free assay which measures the level of radioactive precursors incorporated into DNA.

Assessment of the antiviral activities of the Compounds 1 and 290 versus the panel of viruses used in these studies was carried out in MT4 cells. Cells were batch infected with the appropriate virus stock at a multiplicity of infection of 0.001–0.005 $TCID_{50}$ per cell for 2 hours at 37° C. The cells were washed, resuspended in RPMI/FBS and plated in 24 well dishes at a final concentration of $1.5 \times 10^5$ cells/ml to which were added 2x drug treatments prepared in RPMI/FBS. All treatment concentrations were tested in duplicate. The final DMSO concentration for all treatments or vehicle control cultures was 0.1%. At four days post-infection culture fluid samples were collected for HIV-1 p24 core antigen quantitation to determine antiviral effects. Linear regression analysis was used to calculate the drug concentration necessary to inhibit 90% (inhibitory concentration 90, $IC_{90}$) of non-drug treated p24 antigen production.

| RTI | MF-delavirdine (P236L) $IC_{90}$ ($\mu M$) | IIIB-WT $IC_{90}$ ($\mu M$) |
|---|---|---|
| Compound #1 | 0.02 | 0.008 |
| Compound #290 | 0.02 | 0.004 |

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—C(=$Z_1$)H. Groups $R_i$ and $R_j$ would represent monovalent variable substituents if attached to the formula $CH_3$—$CH_2$—C($R_i$)($R_j$)H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom.

Chemical formulas or portions thereof drawn in a linear fashion represent atoms in a linear chain. The symbol "-" in general represents a bond between two atoms in the chain. Thus $CH_2$—O—$CH_2$—CH($R_i$)—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡—C—CH($R_i$)—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$)—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—($CH_2$)$_2$—N($C_2H_5$)—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol "- - -" or ". . .". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —C(=$R_i$)$_i$ might be bivalent and be defined as oxo or keto (thus forming a carbonyl group (—CO—) or as two separately attached monovalent variable substituents $\alpha$-$R_{i\text{-}j}$ and $\beta$-$R_{i\text{-}k}$. When a bivalent variable, $R_i$, is defined to consist of two monovalent variable substituents, the convention used to define the bivalent variable is of the form "$\alpha$-$R_{i\text{-}j}$:$\beta$-$R_{i\text{-}k}$" or some variant thereof. In such a case both $\alpha$-$R_{i\text{-}j}$ and $\beta$-$R_{i\text{-}k}$ are attached to the carbon atom to give —C($\alpha$-$R_{i\text{-}j}$)($\beta$-$R_{i\text{-}k}$)—.

For example, when the bivalent variable $R_6$, —C(=$R_6$)— is defined to consist of two monovalent variable substituents, the two monovalent variable substituents are $\alpha$-$R_{6-1}$:$\beta$-$R_{6-2}$, ... $\alpha$-$R_{6-9}$:$\beta$-$R_{6-10}$, etc., giving —C($\alpha$-$R_{6-1}$)($\beta$-$R_{6-2}$)—, ... —C($\alpha$-$R_{6-9}$)($\beta$-$R_{6-10}$)—, etc. Likewise, for the bivalent variable $R_{11}$, —C(=$R_{11}$)—, two monovalent variable substituents are $\alpha$-$R_{11-1}$:$\beta$-$R_{11-2}$. For a ring substituent for which separate $\alpha$ and $\beta$ orientations do not exist (e.g., due to the presence of a carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —$C_1$($R_i$)H—$C_2$($R_j$)H— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation "... $R_i$ and $R_h$ are taken together to form —$CH_2$—$CH_2$—O—CO—..." means a lactone in which the carbonyl is bonded to $C_2$. However, when designated "... $R_j$ and $R_i$ are taken together to form —CO—O—$CH_2$—" the convention means a lactone in which the carbonyl is bonded to $C_1$.

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxy-carbonyl because the "$C_1$–$C_3$" refers only to the carbon atom content of the alkoxy group. Similarly while both $C_2$–$C_6$ alkoxyalkyl and ($C_1$–$C_3$)alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.

TLC refers to thin-layer chromatography.

Chromatography refers to medium pressure chromatography on silica gel.

THF refers to tetrahydrofuran.

TBDMS refers to tert-butyldimethylsilyl.

Saline refers to an aqueous saturated sodium chloride solution.

NMR refers to nuclear (proton) magnetic resonance spectroscopy, chemical shifts are reported in ppm ($\delta$) downfield from tetramethylsilane.

IR refers to infrared spectroscopy.

—$\phi$ refers to phenyl ($C_6H_5$).

MS refers to mass spectrometry expressed as m/e or mass/charge unit. [M+H]$^+$ refers to the positive ion of a parent plus a hydrogen atom. EI refers to electron impact. CI refers to chemical ionization. FAB refers to fast atom bombardment.

Ether refers to diethyl ether.

Halo refers to a halogen atom (—Cl, —Br, —F or —I).

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pyridinyl refers to the pyridyl radical as defined by IUPAC nomenclature. For example, 2-pyridyl (pyridine ring substituted in the 2-position).

When solvent pairs are used, the ratios of solvents used are volume/volume (v/v).

HIV refers to HIV-1 (wild type and/or drug resistant mutants thereof e.g. M41L, K65N, K67L, K70R, L74V, V75T, A98G, L100I, K103E, K103N, K103Q, V106A, V108I, E138K, V179D, V179E, Y181C, Y188H, Y188L, G190A, T215Y, T215F, K219Q, K219E, P236L and K238T).

Treatment refers to inhibition of the HIV virus and will differ depending on the infected individual. For individuals who are HIV positive (infected) but who are asymptomatic, the pyrimidine-thioalkyl derivatives of Formula I will delay, or prevent, the onset of symptoms. For individuals who are HIV positive, symptomatic and are pre-AIDS or ARC patients, the pyrimidine-thioalkyl derivatives of Formula I will delay, or prevent, the onset of "full blown AIDS". For individuals who have "full blown AIDS", the pyrimidine-thioalkyl and alkylether derivatives of Formula I will extend survival time of these individuals.

Pyrimidine-thioalkyl and alkylether compounds of Formula I include alpha-substituted pyrimidine-thioalkyl and alkylether compounds. All references to "pyrimidine-thioalkyl and alkylether compounds" and "pyrimidine-thioalkyl and alkylether anti-AIDS compounds" include "alpha-substituted pyrimidine-thioalkyl and alkylether compounds" and "alpha-substituted pyrimidine-thioalkyl and alkylether anti-AIDS compounds" unless specifically indicated otherwise.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

Preparation of (S)-(−)-4-Amino-2-(1-(furo[2,3c]pyridin-5-yl)ethyl)thio)-6-methylthio-pyrimidine; Compound #1

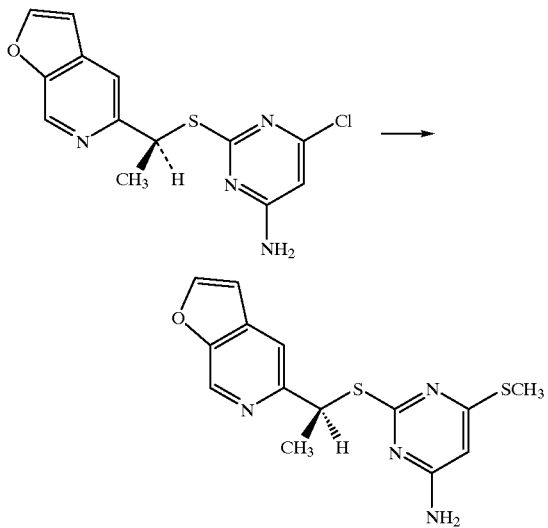

(S)-(−)-4-Amino-6-chloro-2-(1-(furo[2,3c]pyridin-5-yl)ethyl)thio)-pyrimidine (920 mg, 3.0 mmole) is combined with sodium thiomethoxide (263 mg, 3.75 mmole) in 5 ml dimethylformamide in a 25 ml one neck round bottom flask under nitrogen. The reaction is warmed to 65° C. for 45 min, cooled, and is diluted with 25 ml ethyl acetate. The organics are washed with 4×25 ml of 50% saturated 1:1 sodium chloride/sodium bicarbonate, are dried over anhydrous potassium carbonate, and are concentrated in vacuo to a pale oil. The crude material is chromatographed over 60 g of silica gel (230–400 mesh), eluting with 45% ethyl acetate/hexane while collecting 9 ml fractions. Fractions 51–92 are combined and concentrated to a pale oil which is crystallized from diethyl ether to afford the title compound as a pale yellow solid.

$^1$H NMR (d$_6$DMSO): δ1.69 (d, J=7 Hz, 3), 2.40 (s, 3), 5.16 (q, J=7, Hz, 1), 5.97 (s, 1), 6.83 (s, 2), 7.00 (m, 1), 7.77 (m, 1), 8.20 (m, 1), 8.87 (s, 1) ppm.

$^{13}$C NMR (d$_6$DMSO): δ12.5, 22.5, 45.1, 95.5, 106.8, 114.5, 133.3, 134.8, 150.3, 151.2, 154.9, 162.9, 167.5, 169.3 ppm.

Melting Point: 147–149° C.

IR (mull): 3427, 3306, 3176, 2375, 2252, 2144, 1996, 1969, 1633, 1556, 1521, 1282, 1270, 1126, 1118 cm$^{-1}$.

MS (EI) m/z (rel. intensity): 318 (M+, 12), 318 (12), 286 (18), 285 (99), 178 (15), 147 (11), 146 (58), 145 (9), 144 (10), 118 (11), 91 (7).

Specific Rotation (25° C., D) =−269° (c 0.98).

UV λ max: 227(49500, 95% ETHANOL).

Following the general procedure of Example 1 and making noncritical changes, but using the appropriate chloropyrimidine, the following compounds are prepared Ex./Cpd #2 4-amino-2-(benzylthio)-6-methylthiopyrimidine Ex./Cpd #3 4-amino-2-(2-methylphenylmethylthio)-6-methylthiopyrimidine Ex./Cpd #4 4-amino-2-(3-methylphenylmethylthio)-6-methylthiopyrimidine Ex./Cpd #5 4-amino-2-(4-methylphenylmethylthio)-6-methylthiopyrimidine Ex./Cpd #6 4-amino-2-(3-trifluoromethylphenylmethylthio)-6-methylthiopyrimidine Ex./Cpd #7 4-amino-2-(3-methoxyphenylmethylthio)-6-methylthiopyrimidine Ex./Cpd #8 4-amino-2-(4-methoxyphenylmethylthio)-6-methylthiopyrimidine Ex./Cpd #9 4-amino-2-(3-fluorophenylmethylthio)-6-methylthiopyrimidine Ex./Cpd #10 4-amino-2-(3-chlorophenylmethylthio)-6-methylthiopyrimidine Ex./Cpd #11 4-amino-2-(3-bromophenylmethylthio)-6-methylthiopyrimidine Ex./Cpd #12 4-amino-2-(3-iodophenylmethylthio)-6-methylthiopyrimidine Ex./Cpd #13 4-amino-2-(3-nitrophenylmethylthio)-6-methylthiopyrimidine Ex./Cpd #14 4-amino-2-(3-carbomethoxyphenylmethylthio)-6-methylthiopyrimidine Ex./Cpd #15 4-amino-2-(4-t-butylphenylmethylthio)-6-methylthiopyrimidine Ex./Cpd #16 4-amino-2-(3,4-difluorophenylmethylthio)-6-methylthiopyrimidine Ex./Cpd #17 4-amino-2-(3,4-dichlorophenylmethylthio)-6-methylthiopyrimidine Ex./Cpd #18 4-amino-2-(3,5-dichlorophenylmethylthio)-6-methylthiopyrimidine Ex./Cpd #19 4-amino-2-(2,4-dichlorophenylmethylthio)-6-methylthiopyrimidine Ex./Cpd #20 4-amino-2-(3,5-dibromophenylmethylthio)-6-methylthiopyrimidine Ex./Cpd #21 4-amino-5-cyclohexyl-2-(benzylthio)-6-methylthiopyrimidine Ex./Cpd #22 4-amino-5-isopropyl-2-(benzylthio)-6-methylthiopyrimidine Ex./Cpd #23 4-amino-2-(2-pyridylmethylthio)-6-methylthiopyrimidine Ex./Cpd #24 4-amino-2-[2-(3ethoxy)pyridylmethylthio]-6-methylthiopyrimidine Ex./Cpd #25 4-amino-2-(3-pyridylmethylthio)-6-methylthiopyrimidine Ex./Cpd #26 4-amino-2-(1-naphthylmethylthio)-6-methylthiopyrimidine Ex./Cpd #27 4-amino-2-(2-naphthylmethylthio)-6-methylthiopyrimidine Ex./Cpd #28 4-amino-2-(6,7-difluoro-2-naphthylmethylthio)-6-methylthiopyrimidine Ex./Cpd #29 4-amino-2-(2-quinolinylmethylthio)-6-methylthiopyrimidine Ex./Cpd #30 4-amino-2-(6-chloro-5-piperonylmethylthio)-6-methylthiopyrimidine Ex./Cpd #32 4-amino-2-(E-styrylmethylthio)-6-methylthiopyrimidine Ex./Cpd #33 4-amino-2-(propargylthio)-6-methylthiopyrimidine Ex./Cpd #34 4-amino-6-methylthio-2-(2,6-difluorophenylmethylthio)-pyrimidine Ex./Cpd #35 4-amino-6-methylthio-2-(3-bromophenylmethylsulfinyl)-pyrimidine Ex./Cpd #36 4-amino-6-methylthio-2-(2-naphthylmethylsulfinyl)-pyrimidine Ex./Cpd #37 4-amino-6-methylthio-2-(3-bromophenylmethylsulfonyl)-pyrimidine
Ex./Cpd #38 4-amino-5-bromo-6-methylthio-2-(2-naphthylmethylthio)-pyrimidine
Ex./Cpd #39 4-amino-5-bromo-6-methylthio-2-(2-pyridylmethylthio)-pyrimidine
Ex./Cpd #78 4-chloro-6-methylthio-2-(benzylthio)-pyrimidine
Ex./Cpd #79 4-chloro-6-methylthio-5-methoxy-2-(2-naphthylmethylthio)-pyrimidine
Ex./Cpd #80 4-chloro-5-fluoro-6-methylthio-2-(2-naphthylmethylthio)-pyrimidine
Ex./Cpd #81 4-chloro-5-methyl-6-methylthio-2-(2-naphthylmethylthio)-pyrimidine
Ex./Cpd #82 4-chloro-5-fluoro-6-methylthio-2-(2-pyridylmethylthio)-pyrimidine
Ex./Cpd #83 4-chloro-6-methylthio-2-(4-methoxyphenylmethylthio)-pyrimidine
Ex./Cpd #84 4-piperido-6-methylthio-2-(benzylthio)-pyrimidine
Ex./Cpd #85 4-pyrrolidino-6-methylthio-2-(benzylthio)-pyrimidine
Ex./Cpd #86 4-morpholino-6-methylthio-2-(benzylthio)-pyrimidine
Ex./Cpd #87 4-propylamino-6-methylthio-2-(benzylthio)-pyrimidine
Ex./Cpd #88 4-hydrazino-6-methylthio-2-(benzylthio)-pyrimidine
Ex./Cpd #89 4-amino-5-methoxy-6-methylthio-2-(2-naphthylmethylthio)-pyrimidine
Ex./Cpd #90 4-amino-5-methyl-6-methylthio-2-(2-naphthylmethylthio)-pyrimidine
Ex./Cpd #91 4-amino-5-fluoro-6-methylthio-2-(2-naphthylmethylthio)-pyrimidine
Ex./Cpd #92 4-amino-5-fluoro-6-methylthio-2-(2-pyridylmethylthio)-pyrimidine
Ex./Cpd #93 4-amino-6-methylthio-2-(4-methoxyphenylmethylthio)-pyrimidine
Ex./Cpd #99 4-amino-6-methylthio-2-(2-benzothiazolomethylthio)-pyrimidine
Ex./Cpd #100 4-amino-6-methylthio-2-[2-(1-phenyl-1-ethanon)thio]-pyrimidine
Ex./Cpd #101 4-amino-6-methylthio-2-(cyclohex-1-enylmethylthio)-pyrimidine
Ex./Cpd #102 4-amino-6-methylthio-2-(Z-styrylthio)-pyrimidine
Ex./Cpd #103 4-amino-6-methylthio-2-(1-naphthylmethyloxy)-pyrimidine;
Ex./Cpd #104 4-amino-6-methylthio-2-(benzyloxy)-pyrimidine
Ex./Cpd #105 4-amino-6-methylthio-2-(2-naphthylmethyloxy)-pyrimidine
Ex./Cpd #106 4-amino-6-methylthio-2-(3-methylphenylmethyloxy)-pyrimidine
Ex./Cpd #107 4-amino-6-methylthio-2-(3-bromophenylmethyloxy)-pyrimidine
Ex./Cpd #108 4-amino-6-methylthio-2-(3-hydroxyphenylmethylthio)-pyrimidine
Ex./Cpd #109 4-amino-6-methylthio-2-(3-isopropoxyphenylmethylthio)-pyrimidine
Ex./Cpd #110 4-amino-6-methylthio-2-thio-pyrimidine
Ex./Cpd #111 4-amino-6-methylthio-2-[2-(4-chloro)-pyridylmethylthio]-pyrimidine
Ex./Cpd #112 4-amino-6-methylthio-2-[2-(6-chloro)pyridylmethylthio]-pyrimidine
Ex./Cpd #113 4-amino-6-methylthio-2-[2-(6-methyl)pyridylmethylthio]-pyrimidine
Ex./Cpd #114 4-amino-6-methylthio-2-[2-(4-methyl)pyridylmethylthio]-pyrimidine
Ex./Cpd #115 4-amino-6-methylthio-2-[2-(4-ethoxy)pyridylmethylthio]-pyrimidine
Ex./Cpd #116 4-amino-6-methylthio-2-[2-(4-thiophenyl)pyridylmethylthio]-pyrimidine
Ex./Cpd #117 4-amino-6-methylthio-2-[2-(3-methyl)pyridylmethylthio]-pyrimidine
Ex./Cpd #118 4-amino-6-methylthio-2-[2-(5-methyl)pyridylmethylthio]-pyrimidine
Ex./Cpd #119 4-amino-6-methylthio-2-[2-(4-bromo)pyridylmethylthio]-pyrimidine
Ex./Cpd #120 4-amino-6-methylthio-2-[2-(4-methoxy-6-methyl)-pyridylmethylthio]-pyrimidine
Ex./Cpd #121 4-amino-6-methylthio-2-[2-(4,6-dimethyl)pyridylmethylthio]-pyrimidine
Ex./Cpd #122 4-amino-6-methylthio-2-[2-(4-ethyl)pyridylmethylthio]-pyrimidine
Ex./Cpd #123 4-amino-6-methylthio-2-[2-(4-methoxy)pyridylmethylthio]-pyrimidine
Ex./Cpd #124 4-amino-6-methylthio-2-[2-(4-(2-methylpropyl))pyridylmethylthio]-pyrimidine
Ex./Cpd #125 4-amino-6-methylthio-2-[2-(6-chloro-4-methyl)pyridylmethylthio]-pyrimidine
Ex./Cpd #126 4-amino-6-methylthio-2-[2-(4-isopropoxy)pyridylmethylthio]-pyrimidine
Ex./Cpd #127 4-amino-6-methylthio-2-[2-(4,6-dimethyl)pyrimidinylmethylthio]-pyrimidine
Ex./Cpd #128 4-amino-6-methylthio-2-[2-(4-cyano)pyridylmethylthio]-pyrimidine
Ex./Cpd #130 4-amino-6-methylthio-2-[4-(6-methyl)pyrimidinylmethylthio]-pyrimidine
Ex./Cpd #131 4-amino-6-methylthio-2-[2-(4-propyl)pyridylmethylthio]-pyrimidine
Ex./Cpd #132 4-amino-6-methylthio-2-[2-(4-isopropyl)pyridylmethylthio]-pyrimidine
Ex./Cpd #133 4-amino-6-methylthio-2-[2-(5-phenyl)pyridylmethylthio]-pyrimidine
Ex./Cpd #134 4-amino-6-methylthio-2-[2-(4-ethyl)pyridylmethylthio]-pyrimidine
Ex./Cpd #135 4-amino-6-methylthio-2-[2-(4-(α-hydroxy, α-methyl)ethyl)pyridyl-methylthio]-pyrimidine
Ex./Cpd #137 4-amino-6-methylthio-2-[2-(4-cyclopropyl)pyridylmethylthio]-pyrimidine
Ex./Cpd #138 4-amino-6-methylthio-2-[2-(4-cyclopentyl)pyridylmethylthio]-pyrimidine
Ex./Cpd #140 4-amino-6-methylthio-2-[2-(4,5-dimethyl)pyridylmethylthio]-pyrimidine
Ex./Cpd #142 4-amino-6-methylthio-2-[4-(2,6-dimethyl)pyrimidinylmethylthio]-pyrimidine
Ex./Cpd #143 4-amino-6-methylthio-2-[2-(4-pyrrolidino)pyridylmethylthio]-pyrimidine
Ex./Cpd #144 4-Amino-6-methylthio-2-[(5-chlorothiophen-2-ylmethyl)thio]pyrimidine
Ex./Cpd #145 4-amino-6-methylthio-2-[2-(4-(2-butyl))pyridylmethylthio]-pyrimidine
Ex./Cpd #146 4-amino-6-methylthio-2-[2-(4-dimethylamino)pyridylmethylthio]-pyrimidine
Ex./Cpd #147 2-[2-(4-amino-6-methylthio)pyrimidinylthiomethyl]-pyridine-1-oxide
Ex./Cpd #148 4-Amino-6-methylthio-2-[(furan-3-ylmethyl)thio]pyrimidine
Ex./Cpd #149 4-amino-6-methylthio-5-fluoro-2-[2-(4-chloro)pyridylmethylthio]pyrimidine
Ex./Cpd #151 4-amino-6-methylthio-2-[2-(4-(3-pentyl))pyridylmethylthio]-pyrimidine
Ex./Cpd #152 4-amino-6-methylthio-2-[2-(4-acetyl)pyridylmethylthio]-pyrimidine Ex./Cpd #153 4-Amino-6-methylthio-2-[(benzofuran-2-ylmethyl)thio]pyrimidine
Ex./Cpd #154 4-amino-6-methylthio-2-[2-(6-dimethylamino-4-methyl)pyridylmethyl-thio]-pyrimidine
Ex./Cpd #155 4-amino-6-methylthio-2-[(1H-inden-3-ylmethyl)thio]pyrimidine
Ex./Cpd #156 4-amino-6-methylthio-2 [2-(4-carbomethoxy)pyridylmethylthio]-pyrimidine
Ex./Cpd #157 4-Amino-6-methylthio-2-[((S)-(–)perillyl)thio]pyrimidine
Ex./Cpd #158 4-Amino-6-methylthio-2-[(benzothiophen-2-ylmethyl)thio]pyrimidine
Ex./Cpd #159 4-Amino-6-methylthio-2-[(2H-1-benzopyran-3-ylmethyl)thio]pyrimidine
Ex./Cpd #163 4-amino-6-methylthio-2-[2-(4-carboxamido)-pyridylmethylthio]-pyrimidine
Ex./Cpd #164 4-amino-6-methylthio-2-[2-(4-hydroxymethyl)-pyridylmethylthio]-pyrimidine
Ex./Cpd #165 4-amino-5-bromo-6-methylthio-2-[2-(4-methyl)pyridylmethylthio]-pyrimidine
Ex./Cpd #166 4-amino-5-bromo-6-methylthio-2-[2-(4-isopropyl)-pyridylmethylthio]-pyrimidine
Ex./Cpd #167 4-amino-6-methylthio-2-(2,6-dichlorophenyl)methylthio-pyrimidine
Ex./Cpd #168 4-Amino-6-methylthio-2-[(2,3-dihydrobenzofuran-5-ylmethyl)thio]pyrimidine
Ex./Cpd #167 4-amino-6-methylthio-2-(2,6-dichlorophenyl)methylthio-pyrimidine
Ex./Cpd #168 4-Amino-6-methylthio-2-[(2,3-dihydrobenzofuran-5-ylmethyl)thio]pyrimidine
Ex./Cpd #169 4-Amino-6-methylthio-2-[(5-phenylisoxazol-3-ylmethyl)thio]-pyrimidine
Ex./Cpd #170 4-Amino-6-methylthio-2-[(2,3-dihydrobenzofuran-2-ylmethyl)thio]pyrimidine
Ex./Cpd #171 4-Amino-6-methylthio-2-[[(3,4-dihydro-1-naphthalen-2-yl)methyl]thio]-pyrimidine
Ex./Cpd #172 4-Amino-6-methylthio-2-[[(5-chloroimidazo[1,2-a]pyridin-2-yl)methyl]thio]-pyrimidine
Ex./Cpd #173 4-Amino-6-methylthio-2-[(6-methylpyrazin-2-ylmethyl)thio]pyrimidine
Ex./Cpd #174 4-Amino-6-methylthio-2-[(5-methylisoxazol-3-ylmethyl)thio]pyrimidine
Ex./Cpd #175 4-Amino-6-methylthio-2-[(5-methylpyrazin-2-ylmethyl)thio]pyrimidine
Ex./Cpd #176 4-Amino-6-methylthio-2-[(1-methylimidazol-2-ylmethyl)thio]pyrimidine
Ex./Cpd #177 4-Amino-6-methylthio-2-[(3-methylpyrazin-2-ylmethyl)thio]pyrimidine
Ex./Cpd #178 4-Amino-6-methylthio-2-[(quinolin-6-ylmethyl)thio]pyrimidine
Ex./Cpd #179 4-Amino-6-methylthio-2-[(quinoxalin-2-ylmethyl)thio]pyrimidine
Ex./Cpd #180 4-Amino-6-methylthio-2-[(quinolin-8-ylmethyl)thio]pyrimidine
Ex./Cpd #181 4-Amino-6-methylthio-2-[(quinolin-4-ylmethyl)thio]pyrimidine
Ex./Cpd #182 4-Amino-6-methylthio-2-[(isoquinolin-3-ylmethyl)thio]pyrimidine
Ex./Cpd #183 4-Amino-6-methylthio-2-[(quinolin-5-ylmethyl)thio]pyrimidine
Ex./Cpd #184 4-Amino-6-methylthio-2-[(quinolin-7-ylmethyl)thio]pyrimidine
Ex./Cpd #186 4-Amino-6-methylthio-2-[(piperon-5-ylmethyl)thio]pyrimidine
Ex./Cpd #187 4-Amino-6-methylthio-2-[[(3,4-dihydro-1-naphthalenyl)methyl]thio]pyrimidine
Ex./Cpd #188 4-amino-6-methylthio-2-[2-(5-carbomethyoxy)pyridylmethylthio]pyrimidine
Ex./Cpd #189 4-amino-6-methylthio-2 [2-(4-cyclohexyl)pyridylmethylthio]pyrimidine
Ex./Cpd #191 4-chloro-5-fluoro-6-methylthio-2-[2-(4-chloro)pyridyl-methylthio]pyrimidine
Ex./Cpd #192 4-amino-5-fluoro-6-methylthio-2-[2-(4-chloro)pyridyl-methylthio]pyrimidine
Ex./Cpd #193 (E)-4-[(4-Amino-6-methylthio-2-pyrimidinyl)thio]-2-butenoic acid methyl ester
Ex./Cpd #194 (E)-N,N-Diethyl-4-[(4-amino-6-methylthio-2-pyrimidinyl)thio]-2-butenamide
Ex./Cpd #195 (E)-4-methyl-1-[4-[(4-amino-6-methylthio-2-pyrimidinyl)thio]-1-oxo-2-butenyl]piperazine
Ex./Cpd #196 (E)-N-ethyl-4-[(4-amino-6-methylthio-2-pyrimidinyl)thio]-2-butenamide
Ex./Cpd #197 (E)-1-[4-[(4-amino-6-methylthio-2-pyrimidinyl)thio]-1-oxo-2-butenyl]piperidine
Ex./Cpd #198 (E)-4-[(4-amino-6-methylthio-2-pyrimidinyl)thio]-1-oxo-2-butenyl]morpholine
Ex./Cpd #199 (E)-1-[4-[(4-amino-6-methylthio-2-pyrimidinyl)thio]-1-oxo-2-butenyl]pyrrolidine
Ex./Cpd #200 (E)-N-methyl-N-phenyl-4-[(4-amino-6-methylthio-2-pyrimidinyl)thio]-2-butenamide
Ex./Cpd #201 (E)-N-allyl-N-methyl-4-[(4-amino-6-methylthio-2-pyrimidinyl)thio]-2-butenamide
Ex./Cpd #202 (E)-N,N-Dipropyl-4-[(4-amino-6-methylthio-2-pyrimidinyl)thio]-2-butenamide
Ex./Cpd #203 (E)-N-ethyl-N-methyl-4-[(4-amino-6-methylthio-2-pyrimidinyl)thio]-2-butenamide
Ex./Cpd #204 (E)-N,N-Dimethyl-4-[(4-amino-6-methylthio-2-pyrimidinyl)thio]-2-butenamide
Ex./Cpd #207 (E)-N,N-Diethyl-4-[(4-amino-6-methylthio-2-pyrimidinyl)thio]-2-pentenamide
Ex./Cpd #208 (E)-4-[(4-Amino-6-methylthio-2-pyrimidinyl)thio]-3-methyl-2-butenoic acid methyl ester
Ex./Cpd #209 (E)-4-[(4-Amino-6-methylthio-2-pyrimidinyl)thio]-3-methyl-2-pentenoic acid methyl ester
Ex./Cpd #210 4-Amino-6-methylthio-2-(1-(4-(1,1-dimethyl)ethyl-2-pyridyl)ethyl)thio-pyrimidine
Ex./Cpd #211 4-Amino-6-methylthio-2-(1-(2-pyridyl)ethyl)thio-pyrimidine
Ex./Cpd #212 4-Amino-6-methylthio-2-(1-(2-pyridyl)-1-methylethyl)thio-pyrimidine
Ex./Cpd #213 4-Amino-6-methylthio-2-(1-(2-(4-methyl)pyridyl)-1-methylethyl)thio-pyridine
Ex./Cpd #214 4-Amino-6-methylthio-2-(1-(4-cyano-2-pyridyl)ethyl)thio-pyrimidine
Ex./Cpd #215 4-Amino-6-methylthio-2-(1-(4-methyl-2-pyridyl)ethyl)thio-pyrimidine hydrochloride
Ex./Cpd #216 4-Amino-6-methylthio-2-(1-(4-ethyl-2-pyridyl)ethyl)thio-pyrimidine
Ex./Cpd #217 4-Amino-6-methylthio-2-(1-(4-methyl-2-pyridyl)-1-cyanomethyl)thio-pyrimidine
Ex./Cpd #218 4-Amino-6-methylthio-2-(1-(4-methyl-2-pyridyl)propyl)thio-pyrimidine
Ex./Cpd #219 4-Amino-6-methylthio-2-(1-(4-acetyl-2-pyridyl)ethyl)thio-pyrimidine
Ex./Cpd #220 4-Amino-6-methylthio-2-(1-(4-methyl-2-pyridyl)-1-carbomethoxy-methyl)thio-pyrimidine
Ex./Cpd #221 4-Amino-6-methylthio-2-(1-(4-(1-methylethenyl)-2-pyridyl)ethyl)thio-pyrimidine
Ex./Cpd #223 4-Amino-6-methylthio-2-(1-(4-(1-methylethyl)-2-pyridyl)ethyl)thio-pyrimidine
Ex./Cpd #224 4-Amino-6-methylthio-2-(1-(4-methyl-2-pyridyl)pentyl)thio-pyrimidine
Ex./Cpd #225 4-Amino-5-bromo-6-methylthio-2-(1-(4-methylethyl)-2-pyridyl)ethyl)thio-pyrimidine
Ex./Cpd #226 4-Amino-6-methylthio-2-(1-(4-methyl-2-pyridyl)-1-cyclopropyl-methyl)thio-pyrimidine mesylate Ex./Cpd #227 4-Amino-6-methylthio-2-(1-(4-(4-morpholinyl)methyl-2-pyridyl)ethyl)thio-pyrimidine Ex./Cpd #228 4-Amino-6-methylthio-2-(1-(4-dimethylaminomethyl-2-pyridyl)ethyl)thio-pyrimidine Ex./Cpd #229 4-Amino-6-methylthio-2-(1-(2-naphthalenyl)ethyl)thio-pyrimidine Ex./Cpd #230 4-Amino-6-methylthio-2-(1-(3-isoquinolyl)ethyl)thio-pyrimidine Ex./Cpd #231 4-Amino-5-bromo-6-methylthio-2-(1-(3-isoquinolyl)ethyl)thio-pyrimidine Ex./Cpd #232 4-Amino-6-methylthio-2-(1-(1-isoquinolyl)ethyl)thio-pyrimidine Ex./Cpd #233 4-Amino-6-methylthio-2-(1-(3-(5,6,7,8-tetrahydro-isoquinolyl))ethyl)thio-pyrimidine Ex./Cpd #235 4-Amino-6-methylthio-2-(1-(1-(5,6,7,8-tetrahydroisoquinolyl))-ethyl)thio-pyrimidine Ex./Cpd #236 4-Amino-5-bromo-6-methylthio-2-(1-(1-(5,6,7,8-tetrahydro-isoquinolyl))ethyl)thio-pyrimidine Ex./Cpd #237 4-Amino-6-methylthio-2-(1-(7-chlorofuro[2,3-c]pyridine-5-yl)ethyl)thio-pyrimidine Ex./Cpd #238 4-Amino-6-methylthio-2-(1-(furo[2,3-c]pyridin-5-yl)ethyl)thio-pyrimidine Ex./Cpd #240 4-Amino-6-methylthio-2-(1-(7-chloro-2-methylfuro[2,3-c]pyridine-5-yl)ethyl)thio-pyrimidine Ex./Cpd #242 4-Amino-6-methylthio-2-(1-(2-methylfuro[2,3-c]pyridine-5-yl)ethyl)thio-pyrimidine Ex./Cpd #244 4-Amino-6-methylthio-2-(1-(6-chloro-5-methoxy-4-vinyl-2-pyridyl)ethyl)thio-pyrimidine Ex./Cpd #245 4-Amino-6-methylthio-2-(1-(4-ethyl-5-methoxy-2-pyridyl)ethyl)thio-pyrimidine Ex./Cpd #246 4-Amino-6-methylthio-2-(1-(3-methylfuro[2,3-c]pyridine-5-yl)ethyl)thio-pyrimidine Ex./Cpd #247 4-Amino-6-methylthio-2-(1-(2,3-dihydrofuro[2,3-c]pyridine-5-yl)ethyl)thio-pyrimidine Ex./Cpd #248 4-Amino-6-methylthio-2-(1-(3,3-dimethyl-2,3-dihydrofuro[2,3-c]pyridine-5-yl)ethyl)thio-pyrimidine Ex./Cpd #249 4-Amino-6-methylthio-2-(1-(3-ethylfuro[2,3-c]pyridine-5-yl)ethyl)thio-pyrimidine Ex./Cpd #250 4-Amino-6-methylthio-2-(1-(7-chloro-3,3-dimethyl-2,3-dihydrofuro[2,3-c]pyridine-5-yl)ethyl)thio-pyrimidine Ex./Cpd #251 4-Amino-6-methylthio-2-(1-(7-chloro-3-ethylfuro-[2,3-c]pyridine-5-yl)ethyl)thio-pyrimidine Ex./Cpd #252 4-Amino-6-methylthio-2-(1-(3-(l1-methylethyl)furo[2,3-c]-pyridin-5-yl)ethyl)thio-pyrimidine Ex./Cpd #253 4-amino-6-methylthio-2-(1-(4-cylcopentyl)-2-pyridyl)-ethyl)thio-pyrimidine Ex./Cpd #255 4-amino-6-methylthio-2-(1-(4-cyclopropyl)-2-pyridyl)-ethyl)thio-pyrimidine Ex./Cpd #256 4-amino-6-methylthio-2-(1-(4-(1-methylpropyl)-2-pyridyl)-ethyl)thio-pyrimidine Ex./Cpd #257 4-amino-6-methylthio-2-(1-(4-cyclohexyl)-2-pyridyl)-ethyl)thio-pyrimidine Ex./Cpd #258 4-amino-6-methylthio-2-(1-(4-(1-pyrryl))-2-pyridyl)-ethyl)thio-pyrimidine Ex./Cpd #259 4-amino-6-methylthio-2-(1-(4-dimethylamino)-2-pyridyl)-ethyl)thio-pyrimidine Ex./Cpd #260 4-amino-6-methylthio-2-(l1-(5-(l1-methylethyl)-3-pyridyl)-ethyl)thio-pyrimidine Ex./Cpd #261 4-amino-6-methylthio-2-(1-(4-(1-ethylpropyl)-2-pyridyl)-ethyl)thio-pyrimidine Ex./Cpd #262 4-amino-6-methylthio-2-(1-(4-methyl-6-(1-pyrryl))-2-pyridyl)-ethyl)thio-pyrimidine Ex./Cpd #263 4-amino-6-methylthio-2-(1-(4-(2-propyloxy))-2-pyridyl)-ethyl)thio-pyrimidine Ex./Cpd #282 4-amino-6-methylthio-2-(1-(3-chloro-[2,3-c]pyridine-5-yl)ethyl)thio-pyrimidine Ex./Cpd #283 4-Amino-6-methylthio-2-(1-(3,7-dichlorofuro[2,3-c]pyridine-5-yl)ethyl)thio-pyrimidine Ex./Cpd #284 4-Amino-6-methylthio-2-(1-(3-bromofuro[2,3-c]pyridine-5-yl)ethyl)thio-pyrimidine Ex./Cpd #285 4-Amino-6-methylthio-2-(1-(3-bromo-7-chlorofuro[2,3-c]pyridine-5-yl)ethyl)thio-pyrimidine Ex./Cpd #286 4-Amino-6-methylthio-2-(1-(7-chloro-3-methylfuro[2,3-c]pyridine-5-yl)ethyl)thio-pyrimidine Ex./Cpd #289 (R)-(+)-4-Amino-6-methylthio-2-(1-(3-methylfuro[2,3-c]pyridine-5-yl)ethyl)thio-pyrimidine Ex./Cpd #290 (S)-(−)-4-Amino-6-methylthio-2-(1-(3-methylfuro[2,3-c]pyridine-5-yl)ethyl)thio-pyrimidine, mp 80–82° C.

Ex./Cpd #291 R-(+)-4-Amino-6-methylthio-2-(1-(4-ethyl-2-pyridyl)ethyl)thio-pyrimidine Ex./Cpd #292 (−)-4-Amino-6-methylthio-2-(1-(4-ethyl-2-pyridyl)ethyl)thio-pyrimidine Ex./Cpd #293 4-amino-6-methylthio-2-(1-(7-chloro-3-trifluoromethyl)-furo[2,3-c]pyridin-5-yl)ethylthio)-pyrimidine Ex./Cpd #294 4-Amino-6-methylthio-2-(1-(3-trifluoromethyl)-furo[2,3-c]pyridin-5-yl)ethylthio)-pyrimidine Ex./Cpd #300 (R)-(+)-4-Amino-6-methylthio-2-(1-(furo[2,3-c]pyridin-5-yl)ethylthio)-pyrimidine Ex./Cpd #301 (S)-(−)-4-Amino-6-methylthio-2-(1-(furo[2,3-c]pyridin-5-yl)ethylthio)-pyrimidine mesylate salt Ex./Cpd #302 (S)-(−)-4-Amino-6-methylthio-2-(1-(3-methylfuro[2,3-c]pyridin-5-yl)ethylthio)-pyrimidine, esylate salt Ex./Cpd #303 4-amino-6-methylthio-2-(((5-benzyloxy-6-chloro)-2-pyridyl)-ethyl)thio-pyrimidine Ex./Cpd #304 4-amino-6-methylthio-2-(furo[2,3-b]pyridin-5-yl-methylthio)-pyrimidine Following the above procedures and making non-critical variations, the following compounds are prepared:

4-Amino-6-methylthio-2-(1-(3-trifluoromethylfuro[2,3-c]pyridin-5-yl)ethyl)thio-pyrimidine, 4-Amino-6-methylthio-2-(1-(7-chloro-3-trifluoromethylfuro[2,3-c]pyridin-5-yl)ethyl)thio-pyrimidine, 4-Amino-6-methylthio-2-(1-(3-fluorofuro[2,3-c]pyridin-5-yl)ethyl)thio-pyrimidine, 4-Amino-6-methylthio-2-(1-(3-((2,2,2-trifluoro)ethyl)furo[2,3-c]pyridin-5-yl)ethyl)thio-pyrimidine, 4-Amino-6-methylthio-2-(1-(3-((1-trifluoromethyl-2,2,2-trifluoro)ethyl)furo[2,3-c]pyridin-5-yl)ethyl)thio-pyrimidine, 4-Amino-6-methylthio-2-(1-(3-cyanofuro[2,3-c]pyridin-5-yl)ethyl)thio-pyrimidine, 4-Amino-6-methylthio-2-(1-(3-carbomethoxyfuro[2,3-c]pyridin-5-yl)ethyl)thio-pyrimidine, 4-Amino-6-methylthio-2-(1-(3-aminocarbinylfuro[2,3-c]pyridin-5-yl)ethyl)thio-pyrimidine, 4-Amino-6-methylthio-2-(1-(3-(N,N-dimethylaminocarbinyl)furo[2,3-c]pyridin-5-yl)ethyl)thio-pyrimidine, 4-Amino-6-methylthio-2-(1-(3-(methylsulfonylamino)furo[2,3-c]pyridin-5-yl)ethyl)thio-pyrimidine, 4-Amino-6-methylthio-2-(1-(3-(methylcarboxyamino)furo[2,3-c]pyridin-5-yl)ethyl)thio-pyrimidine, 4-Amino-6-methylthio-2-(1-(3-phenylfuro[2,3-c]pyridin-5-yl)ethyl)thio-pyrimidine, 4-Amino-6-methylthio-2-(1-(3-(tert-butyl)furo[2,3-c]pyridin-5-yl)ethyl)thio-pyrimidine, 4-Amino-6-methylthio-2-(1-(3-cyclopropylfuro[2,3-c]pyridin-5-yl)ethyl)thio-pyrimidine, 4-Amino-6-methylthio-2-(1-(3-fluorothieno[2,3-c]pyridin-5-yl)ethyl)thio-pyrimidine,
4-Amino-6-methylthio-2-(1-(3-((2,2,2-trifluoro)ethyl)thieno[2,3-c]pyridin-5-yl)ethyl)thio-pyrimidine,
4-Amino-6-methylthio-2-(1-(3-((1-trifluoromethyl-2,2,2-trifluoro)ethyl)thieno[2,3-c]pyridin-5-yl)ethyl)thio-pyrimidine,
4-Amino-6-methylthio-2-(1-(3-cyanothieno[2,3-c]pyridin-5-yl)ethyl)thio-pyrimidine,
4-Amino-6-methylthio-2-(1-(3-carbomethoxythieno[2,3-c]pyridin-5-yl)ethyl)thio-pyrimidine,
4-Amino-6-methylthio-2-(1-(3-aminocarbinylthieno[2,3-c]pyridin-5-yl)ethyl)thio-pyrimidine,
4-Amino-6-methylthio-2-(1-(3-(N,N-dimethylaminocarbinyl)thieno[2,3-c]pyridin-5-yl)ethyl)thio-pyrimidine,
4-Amino-6-methylthio-2-(1-(3-(methylsulfonylamino)thieno[2,3-c]pyridin-5-yl)ethyl)thio-pyrimidine,
4-Amino-6-methylthio-2-(1-(3-(methylcarboxyamino)thieno[2,3-c]pyridin-5-yl)ethyl)thio-pyrimidine,
4-Amino-6-methylthio-2-(1-(3-phenylthieno[2,3-c]pyridin-5-yl)ethyl)thio-pyrimidine,
4-Amino-6-methylthio-2-(1-(3-(tert-butyl)thieno[2,3-c]pyridin-5-yl)ethyl)thio-pyrimidine,
4-Amino-6-methylthio-2-(1-(3-cyclopropylthieno[2,3-c]pyridin-5-yl)ethyl)thio-pyrimidine,
4-Amino-6-methylthio-2-(1-(3-fluoro-1H-pyrrolo[2,3-c]pyridin-5-yl)ethyl)thio-pyrimidine,
4-Amino-6-methylthio-2-(1-(3-((2,2,2-trifluoro)ethyl)-1H-pyrrolo[2,3-c]pyridin-5-yl)ethyl)thio-pyrimidine,
4-Amino-6-methylthio-2-(1-(3-((1-trifluoromethyl-2,2,2-trifluoro)ethyl)-1H-pyrrolo[2,3-c]pyridin-5-yl)ethyl)thio-pyrimidine,
4-Amino-6-methylthio-2-(1-(3-cyano-1H-pyrrolo[2,3-c]pyridin-5-yl)ethyl)thio-pyrimidine,
4-Amino-6-methylthio-2-(1-(3-carbomethoxy-1H-pyrrolo[2,3-c]pyridin-5-yl)ethyl)thio-pyrimidine,
4-Amino-6-methylthio-2-(1-(3-aminocarbinyl-1H-pyrrolo[2,3-c]pyridin-5-yl)ethyl)thio-pyrimidine,
4-Amino-6-methylthio-2-(1-(3-(N,N-dimethylaminocarbinyl)-1H-pyrrolo[2,3-c]pyridin-5-yl)ethyl)thio-pyrimidine,
4-Amino-6-methylthio-2-(1-(3-(methylsulfonylamino)-1H-pyrrolo[2,3-c]pyridin-5-yl)ethyl)thio-pyrimidine,
4-Amino-6-methylthio-2-(1-(3-(methylcarboxyamino)-1H-pyrrolo[2,3-c]pyridin-5-yl)ethyl)thio-pyrimidine,
4-Amino-6-methylthio-2-(1-(3-phenyl-1H-pyrrolo[2,3-c]pyridin-5-yl)ethyl)thio-pyrimidine,
4-Amino-6-methylthio-2-(1-(3-(tert-butyl)-1H-pyrrolo[2,3-c]pyridin-5-yl)ethyl)thio-pyrimidine,
4-Amino-6-methylthio-2-(1-(3-cyclopropyl-1H-pyrrolo[2,3-c]pyridin-5-yl)ethyl)thio-pyrimidine,
4-Amino-6-methylthio-2-(1-(3-fluoro-1-methyl-1H-pyrrolo[2,3-c]pyridin-5-yl)ethyl)thio-pyrimidine,
4-Amino-6-methylthio-2-(1-(3-((2,2,2-trifluoro)ethyl)-1-methyl-1H-pyrrolo[2,3-c]pyridin-5-yl)ethyl)thio-pyrimidine,
4-Amino-6-methylthio-2-(1-(3-((1-trifluoromethyl-2,2,2-trifluoro)ethyl)-1-methyl-1H-pyrrolo[2,3-c]pyridin-5-yl)ethyl)thio-pyrimidine,
4-Amino-6-methylthio-2-(1-(3-cyano-1-methyl-1H-pyrrolo[2,3-c]pyridin-5-yl)ethyl)thio-pyrimidine,
4-Amino-6-methylthio-2-(1-(3-carbomethoxy-1-methyl-1H-pyrrolo[2,3-c]pyridin-5-yl)ethyl)thio-pyrimidine,
4-Amino-6-methylthio-2-(1-(3-aminocarbinyl-1-methyl-1H-pyrrolo[2,3-c]pyridin-5-yl)ethyl)thio-pyrimidine,
4-Amino-6-methylthio-2-(1-(3-(N,N-dimethylaminocarbinyl)-1-methyl-1H-pyrrolo[2,3-c]pyridin-5-yl)ethyl)thio-pyrimidine,
4-Amino-6-methylthio-2-(1-(3-(methylsulfonylamino)-1-methyl-1H-pyrrolo[2,3-c]pyridin-5-yl)ethyl)thio-pyrimidine,
4-Amino-6-methylthio-2-(1-(3-(methylcarboxyamino)-1-methyl-1H-pyrrolo[2,3-c]pyridin-5-yl)ethyl)thio-pyrimidine,
4-Amino-6-methylthio-2-(1-(3-phenyl-1-methyl-1H-pyrrolo[2,3-c]pyridin-5-yl)ethyl)thio-pyrimidine,
4-Amino-6-methylthio-2-(1-(3-(tert-butyl)-1-methyl-1H-pyrrolo[2,3-c]pyridin-5-yl)ethyl)thio-pyrimidine,
4-Amino-6-methylthio-2-(1-(3-cyclopropyl-1-methyl-1H-pyrrolo[2,3-c]pyridin-5-yl)ethyl)thio-pyrimidine,
4-Amino-6-methylthio-2-(1-(7-chlorothieno[2,3-c]pyridin-5-yl)ethyl)thio-pyrimidine,
4-Amino-6-methylthio-2-(1-(thieno[2,3-c]pyridin-5-yl)ethyl)thio-pyrimidine,
4-Amino-6-methylthio-2-(1-(7-chloro-2-methylthieno[2,3-c]pyridin-5-yl)ethyl)thio-pyrimidine,
4-Amino-6-methylthio-2-(1-(2-methylthieno[2,3-c]pyridin-5-yl)ethyl)thio-pyrimidine,
4-Amino-6-methylthio-2-(1-(3-methylthieno[2,3-c]pyridin-5-yl)ethyl)thio-pyrimidine
4-Amino-6-methylthio-2-(1-(2,3-dihydrothieno[2,3-c]pyridin-5-yl)ethyl)thio-pyrimidine,
4-Amino-6-methylthio-2-(1-(3,3-dimethyl-2,3-dihydrothieno[2,3-c]pyridin-5-yl)ethyl)thio-pyrimidine,
b 4-Amino-6-methylthio-2-(1-(3-ethylthieno[2,3-c]pyridin-5-yl)ethyl)thio-pyrimidine,
4-Amino-6-methylthio-2-(1-(7-chloro-3,3-dimethyl-2,3-dihydrothieno[2,3-c]pyridin-5-yl)ethyl)thio-pyrimidine,
4-Amino-6-methylthio-2-(1-(7-chloro-3-ethylthieno[2,3-c]pyridin-5-yl)ethyl)thio-pyrimidine,
4-Amino-6-methylthio-2-(1-(3-(1-methylethyl)thieno[2,3-c]pyridin-5-yl)ethyl)thio-pyrimidine,
4-Amino-6-methylthio-2-(1-(7-chloro-1H-pyrrolo[2,3-c]pyridin-5-yl)ethyl)thio-pyrimidine,
4-Amino-6-methylthio-2-(1-(1H-pyrrolo[2,3-c]pyridin-5-yl)ethyl)thio-pyrimidine,
4-Amino-6-methylthio-2-(1-(7-chloro-2-methyl-1H-pyrrolo[2,3-c]pyridin-5-yl)ethyl)thio-pyrimidine,
4-Amino-6-methylthio-2-(1-(2-methyl-1H-pyrrolo[2,3-c]pyridin-5-yl)ethyl)thio-pyrimidine,
4-Amino-6-methylthio-2-(1-(3-methyl-1H-pyrrolo[2,3-c]pyridin-5-yl)ethyl)thio-pyrimidine,
4-Amino-6-methylthio-2-(1-(2,3-dihydro-1H-pyrrolo[2,3-c]pyridin-5-yl)ethyl)thio-pyrimidine,
4-Amino-6-methylthio-2-(1-(3,3-dimethyl-2,3-dihydro-1H-pyrrolo[2,3-c]pyridin-5-yl)ethyl)thio-pyrimidine,
4-Amino-6-methylthio-2-(1-(3-ethyl-1H-pyrrolo[2,3-c]pyridin-5-yl)ethyl)thio-pyrimidine,
4-Amino-6-methylthio-2-(1-(7-chloro-3,3-dimethyl-2,3-dihydro-1H-pyrrolo[2,3-c]pyridin-5-yl)ethyl)thio-pyrimidine,
4-Amino-6-methylthio-2-(1-(7-chloro-3-ethyl-1H-pyrrolo[2,3-c]pyridin-5-yl)ethyl)thio-pyrimidine,
4-Amino-6-methylthio-2-(1-(3-(1-methylethyl)-1H-pyrrolo[2,3-c]pyridin-5-yl)ethyl)thio-pyrimidine,
4-Amino-6-methylthio-2-(1-(7-chloro-1-methyl-1H-pyrrolo[2,3-c]pyridin-5-yl)ethyl)thio-pyrimidine,
4-Amino-6-methylthio-2-(1-(1-methyl-1H-pyrrolo[2,3-c]pyridin-5-yl)ethyl)thio-pyrimidine,
4-Amino-6-methylthio-2-(1-(7-chloro-2-methyl-1-methyl-1H-pyrrolo[2,3-c]pyridin-5-yl)ethyl)thio-pyrimidine,
4-Amino-6-methylthio-2-(1-(2-methyl-1-methyl-1H-pyrrolo[2,3-c]pyridin-5-yl)ethyl)thio-pyrimidine,
4-Amino-6-methylthio-2-(1-(3-methyl-1-methyl-1H-pyrrolo[2,3-c]pyridin-5-yl)ethyl)thio-pyrimidine, 4-Amino-6-methylthio-2-(1-(2,3-dihydro-1-methyl-1H-pyrrolo[2,3-c]pyridin-5-yl)ethyl)thio-pyrimidine,
4-Amino-6-methylthio-2-(1-(3,3-dimethyl-2,3-dihydro-1-methyl-1H-pyrrolo[2,3-c]pyridin-5-yl)ethyl)thio-pyrimidine,
4-Amino-6-methylthio-2-(1-(3-ethyl-1-methyl-1H-pyrrolo[2,3-c]pyridin-5-yl)ethyl)thio-pyrimidine,
4-Amino-6-methylthio-2-(1-(7-chloro-3,3-dimethyl-2,3-dihydro-1-methyl-1H-pyrrolo[$^2$,$^3$-c]pyridin-5-yl)ethyl)thio-pyrimidine,
4-Amino-6-methylthio-2-(1-(7-chloro-3-ethyl-1-methyl-1H-pyrrolo[2,3-c]pyridin-5-yl)ethyl)thio-pyrimidine,
4-Amino-6-methylthio-2-(1-(3-(1-methylethyl)-1-methyl-1H-pyrrolo[2,3-c]pyridin-5-yl)ethyl)thio-pyrimidine,
4-Amino-6-methylthio-2-(1-(3-chlorothieno[2,3-c]pyridin-5-yl)ethyl)thio-pyrimidine,
4-Amino-6-methylthio-2-(1-(3,7-dichlorothieno[2,3-c]pyridin-5-yl)ethyl)thio-pyrimidine,
4-Amino-6-methylthio-2-(1-(3-bromothieno[2,3-c]pyridin-5-yl)ethyl)thio-pyrimidine,
4-Amino-6-methylthio-2-(1-(3-bromo-7-chlorothieno[2,3-c]pyridin-5-yl)ethyl)thio-pyrimidine,
4-Amino-6-methylthio-2-(1-(7-chloro-3-methylthieno[2,3-c]pyridin-5-yl)ethyl)thio-pyrimidine,
4-Amino-6-methylthio-2-(1-(3-chloro-1H-pyrrolo[2,3-c]pyridin-5-yl)ethyl)thio-pyrimidine,
4-Amino-6-methylthio-2-(1-(3,7-dichloro-1H-pyrrolo[2,3-c]pyridin-5-yl)ethyl)thio-pyrimidine,
4-Amino-6-methylthio-2-(1-(3-bromo-1H-pyrrolo[2,3-c]pyridin-5-yl)ethyl)thio-pyrimidine,
4-Amino-6-methylthio-2-(1-(3-bromo-7-chloro-1H-pyrrolo[2,3-c]pyridin-5-yl)ethyl)thio-pyrimidine,
4-Amino-6-methylthio-2-(l1-(7-chloro-3-methyl-1H-pyrrolo[2,3 -c]pyridin-5-yl)ethyl)thio-pyrimidine,
4-Amino-6-methylthio-2-(l1-(3-chloro-1-methyl-l1H-pyrrolo[2,3-c]pyridin-5-yl)ethyl)thio-pyrimidine,
4-Amino-6-methylthio-2-(l1-(3,7-dichloro-1-methyl-1H-pyrrolo[2,3-c]pyridin-5-yl)ethyl)thio-pyrimidine,
4-Amino-6-methylthio-2-(l1-(3-bromo-1-methyl-1H-pyrrolo[2,3-c]pyridin-5-yl)ethyl)thio-pyrimidine,
4-Amino-6-methylthio-2-(1-(3-bromo-7-chloro-1-methyl-l H-pyrrolo[2,3-c]pyridin-5-yl)ethyl)thio-pyrimidine,
4-Amino-6-methylthio-2-(1-(7-chloro-3-methyl-1-methyl-1H-pyrrolo[2,3-c]pyridin-5-yl)ethyl)thio-pyrimidine,
4-Amino-6-methylthio-2-(1-(3-trifluoromethylthieno[2,3-c]pyridin-5-yl)ethyl)thio-pyrimidine,
4-Amino-6-methylthio-2-(1-(7-chloro-3-trifluoromethylthieno[2,3-c]pyridin-5-yl)ethyl)thio-pyrimidine,
4-Amino-6-methylthio-2-(1-(3-trifluoromethyl-1H-pyrrolo[2,3-c]pyridin-5-yl)ethyl)thio-pyrimidine,
4-Amino-6-methylthio-2-(1-(7-chloro-3-trifluoromethyl-1H-pyrrolo[2,3-c]pyridin-5-yl)ethyl)thio-pyrimidine,
4-Amino-6-methylthio-2-(1-(3-trifluoromethyl-1-methyl-1H-pyrrolo[2,3-c]pyridin-5-yl)ethyl)thio-pyrimidine,
4-Amino-6-methylthio-2-(1-(7-chloro-3-trifluoromethyl-1-methyl-1H-pyrrolo[2,3-c]pyridin-5-yl)ethyl)thio-pyrimidine.

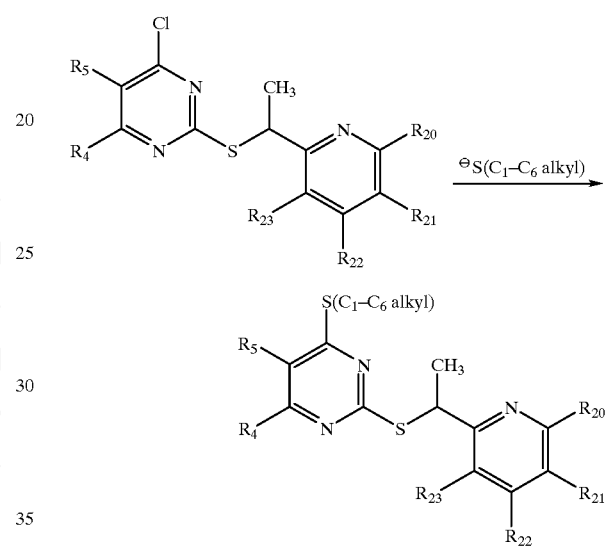

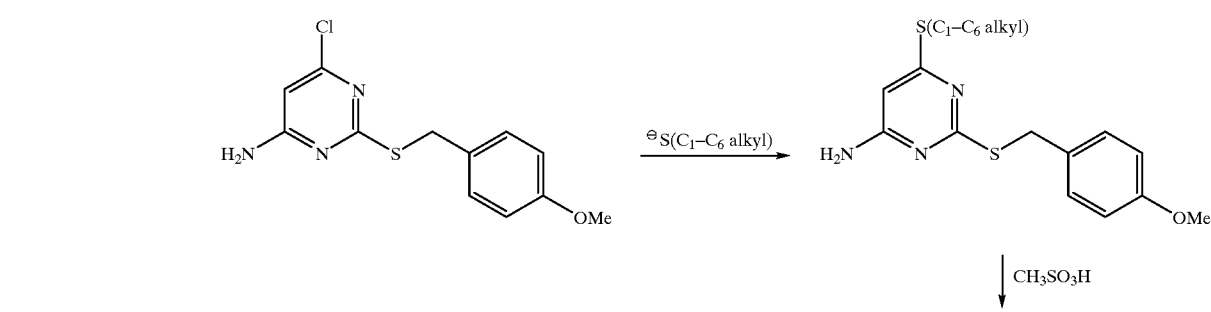

-continued
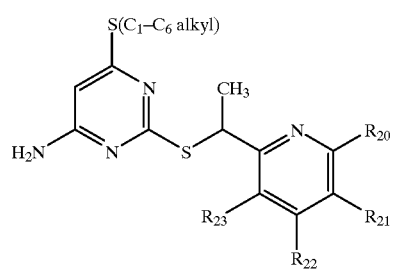
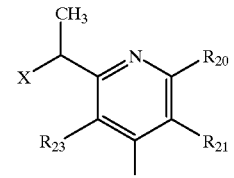
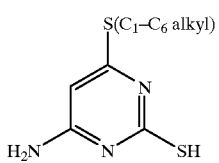
Cpd #1
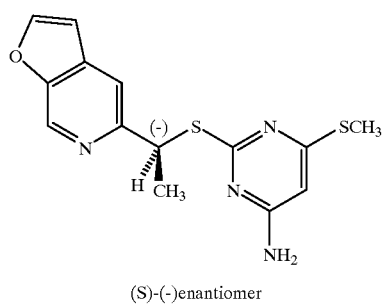
(S)-(-)enantiomer
Cpd #2
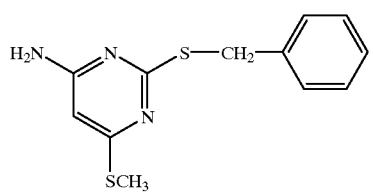
Cpd #3
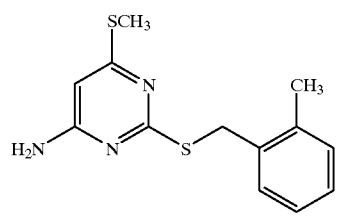
Cpd #4
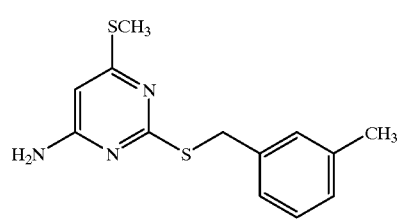
Cpd #5
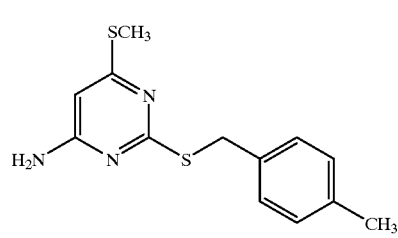
-continued
Cpd #6
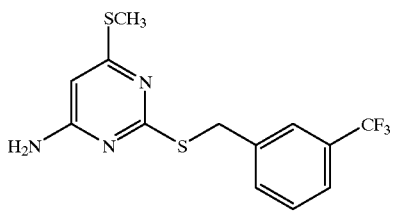
Cpd #7
Cpd #8
Cpd #9
Cpd #10
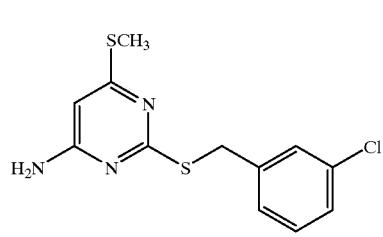

Cpd #11
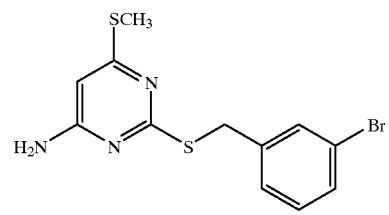
Cpd #12
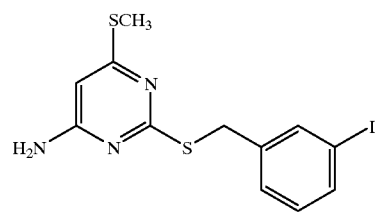
Cpd #13
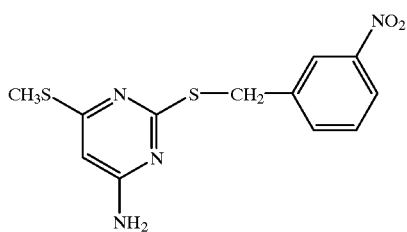
Cpd #14
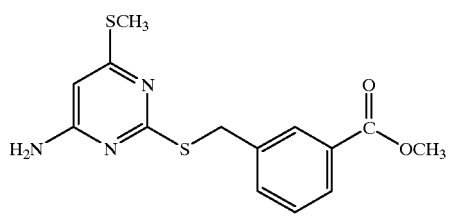
Cpd #15
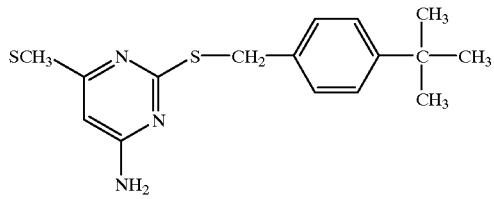
Cpd #16
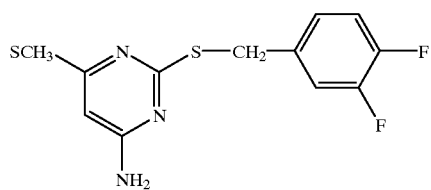
Cpd #17
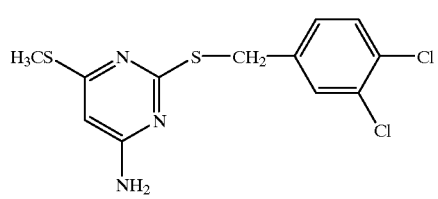
Cpd #18
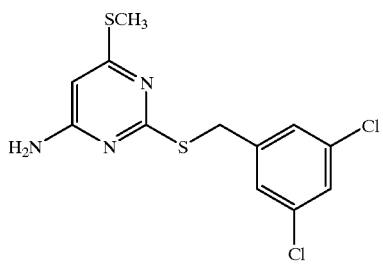
Cpd #19
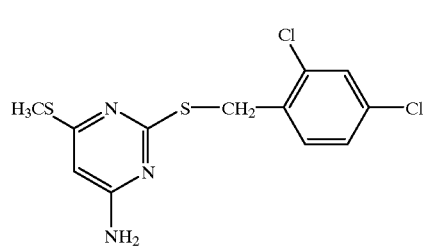
Cpd #20
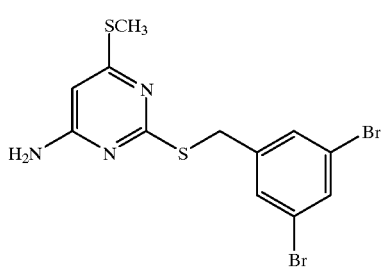
Cpd #21
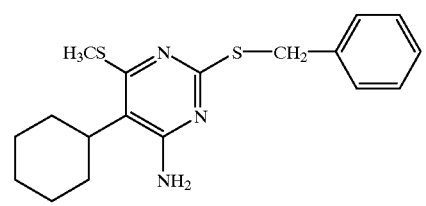
Cpd #22
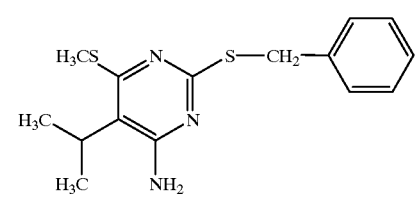
Cpd #23
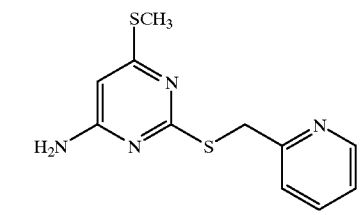

-continued
Cpd #24
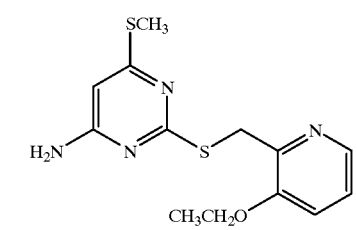
Cpd #25
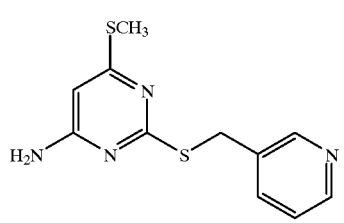
Cpd #26
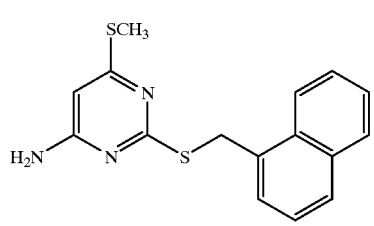
Cpd #27
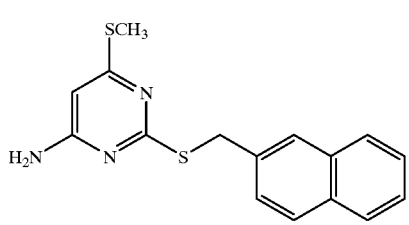
Cpd #28
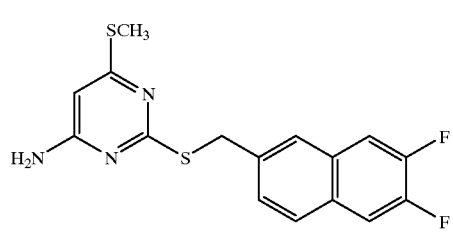
Cpd #29
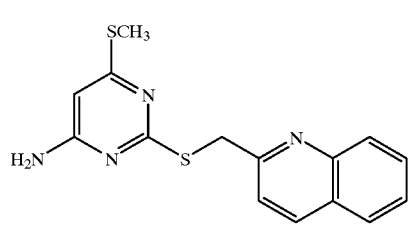
-continued
Cpd #30
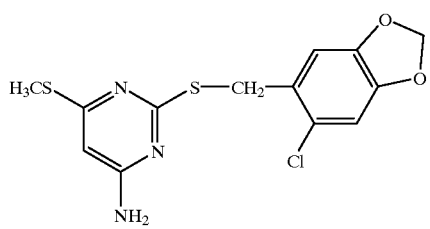
Cpd #32
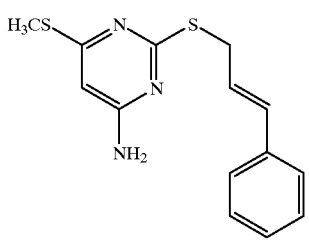
Cpd #33
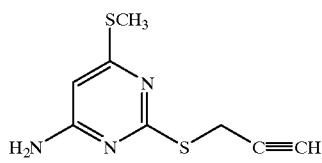
Cpd #34
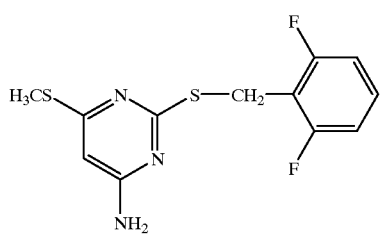
Cpd #35
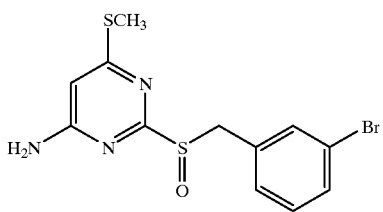
Cpd #36
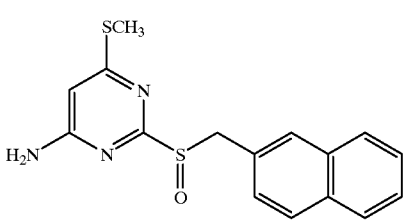
Cpd #37
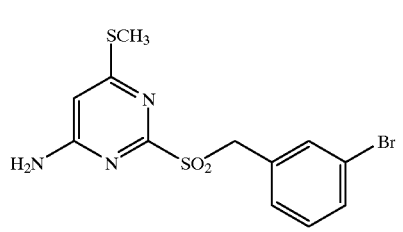

Cpd #38
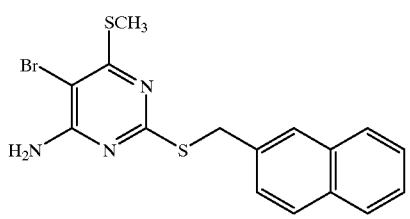
Cpd #39
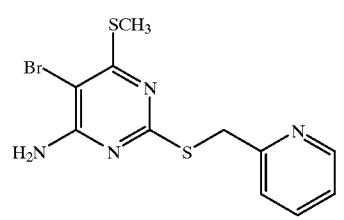
Cpd #78
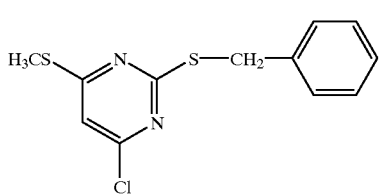
Cpd #79
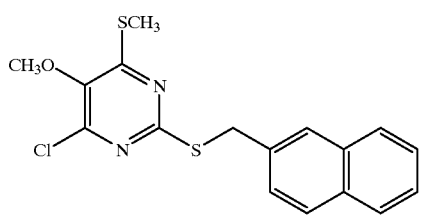
Cpd #80
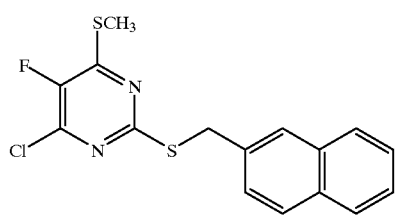
Cpd #81
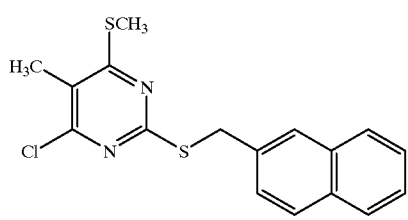
Cpd #82
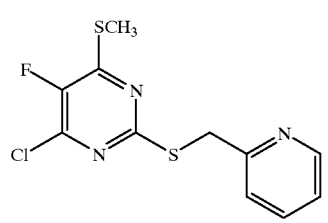
Cpd #83
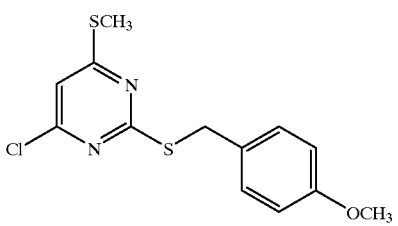
Cpd #84
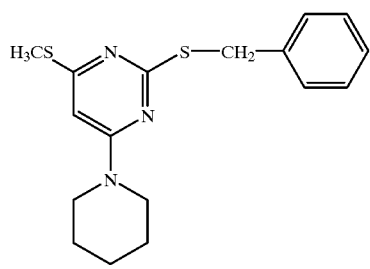
Cpd #85
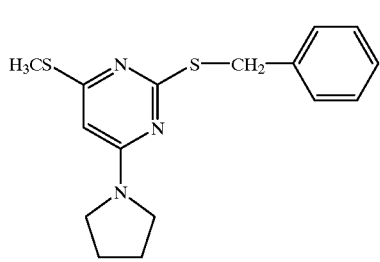
Cpd #86
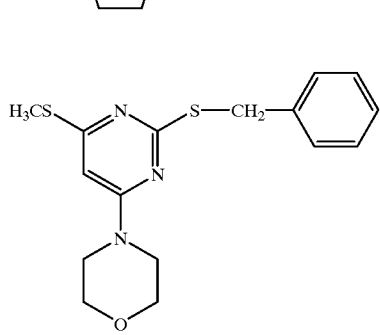
Cpd #87
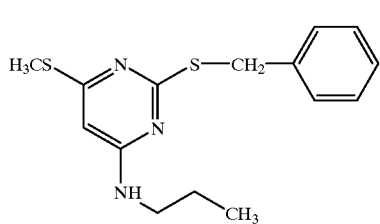
Cpd #88
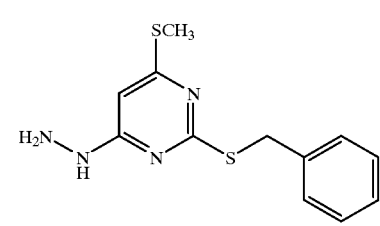

Cpd #89
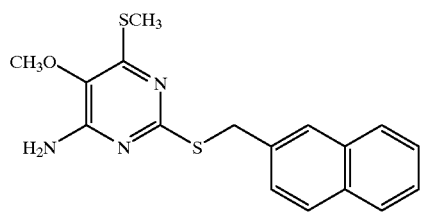
Cpd #90
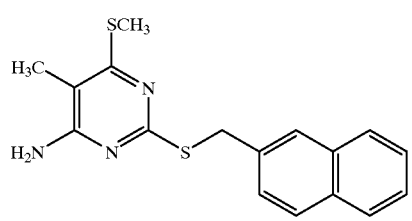
Cpd #91
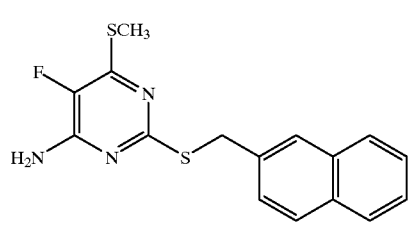
Cpd #92
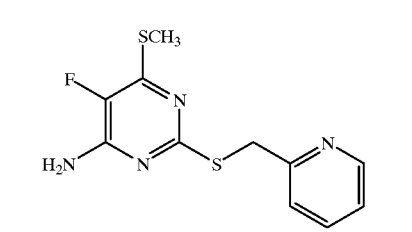
Cpd #93
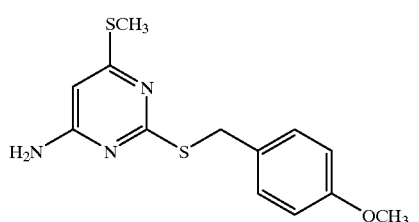
Cpd #99
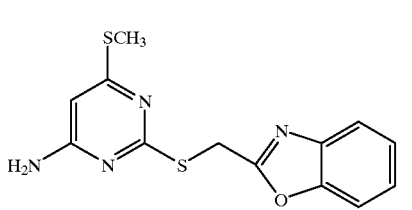
Cpd #100
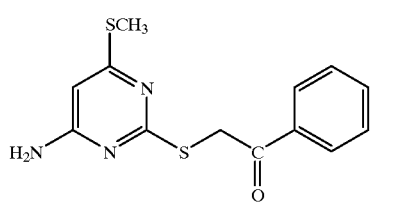
Cpd #101
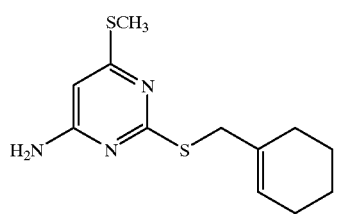
Cpd #102
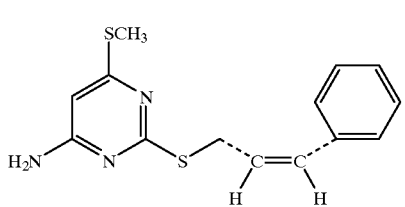
cis isomer
Cpd #103
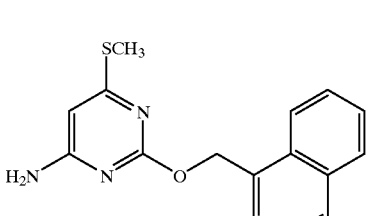
Cpd #104
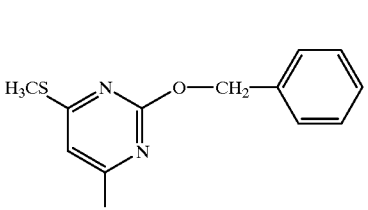
Cpd #105
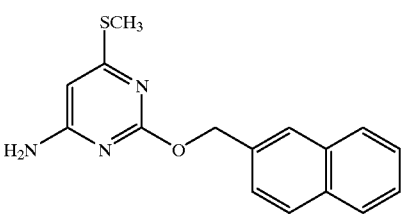
Cpd #106
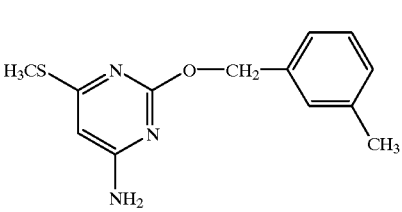
Cpd #107
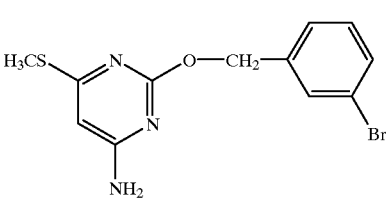

Cpd #108
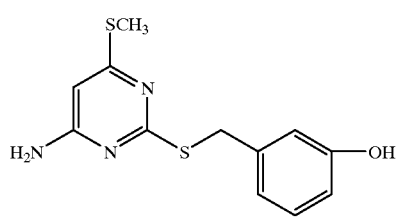
Cpd #109
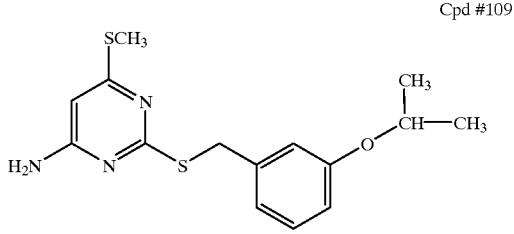
Cpd #110
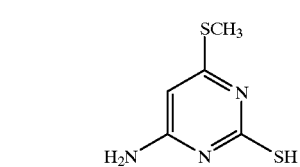
Cpd #111
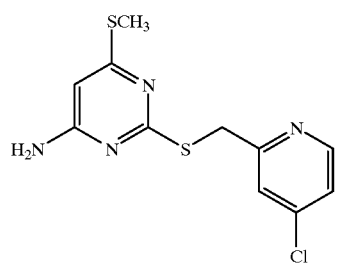
Cpd #112
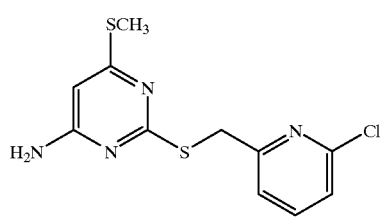
Cpd #113
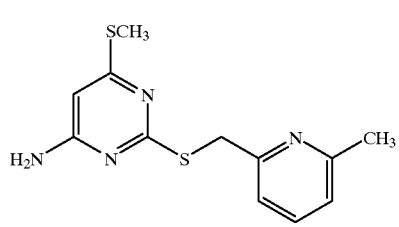
Cpd #114
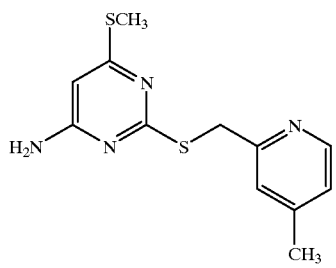
Cpd #115
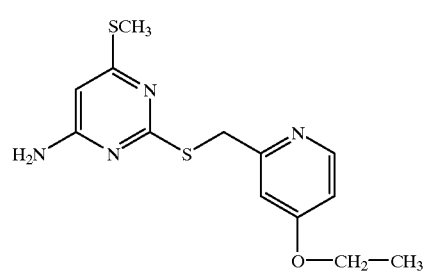
Cpd #116
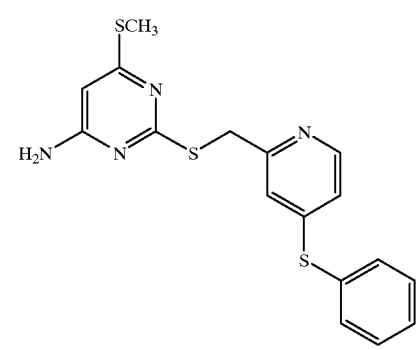
Cpd #117
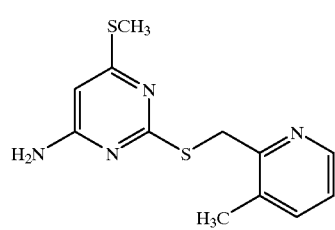
Cpd #118
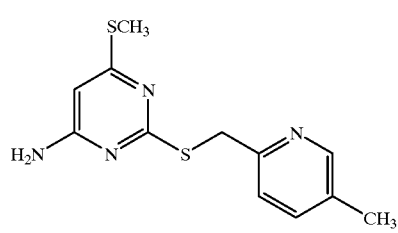

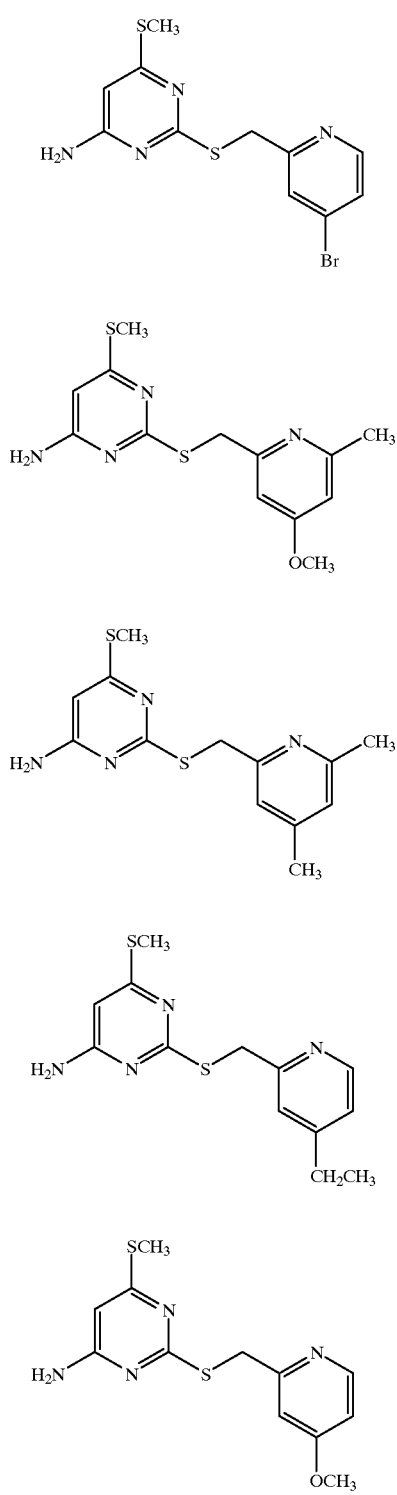
Cpd #119
Cpd #120
Cpd #121
Cpd #122
Cpd #123
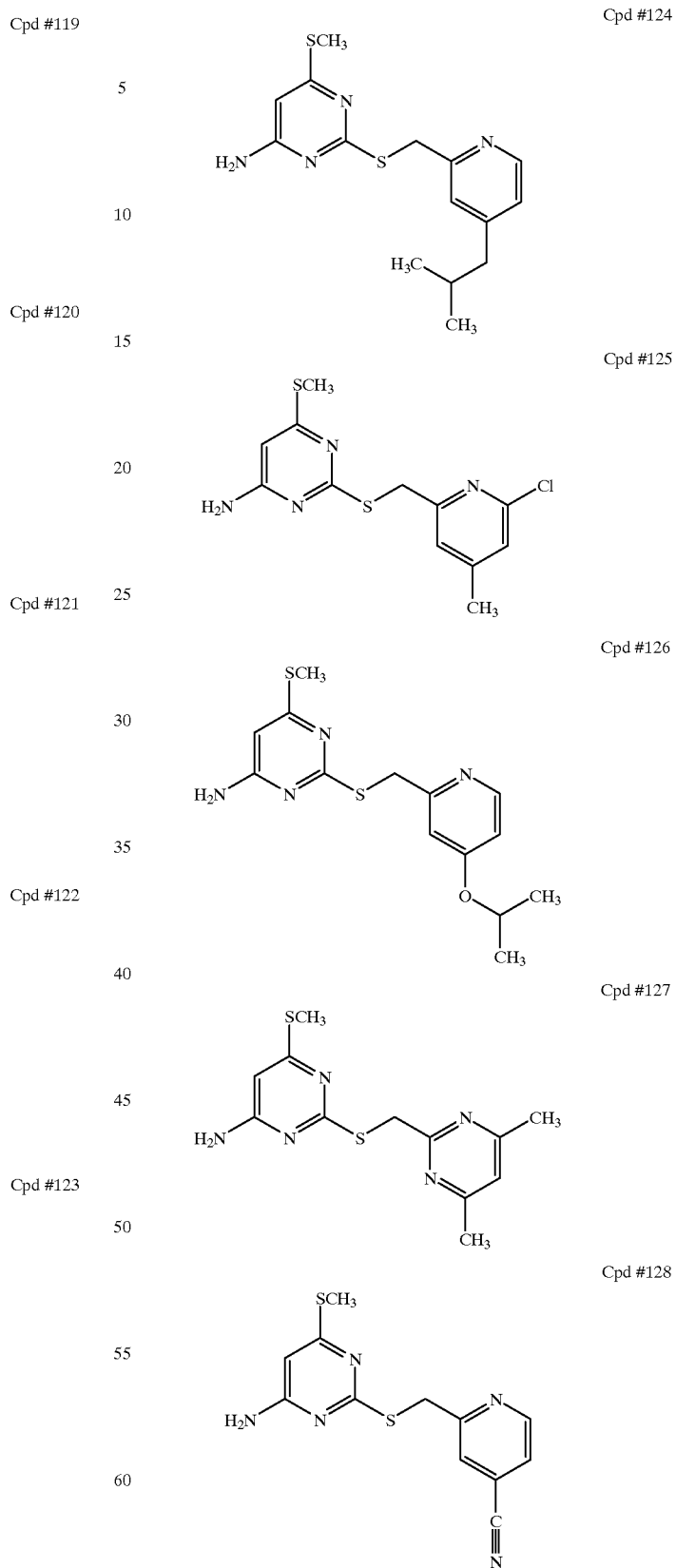
Cpd #124
Cpd #125
Cpd #126
Cpd #127
Cpd #128

Cpd #130
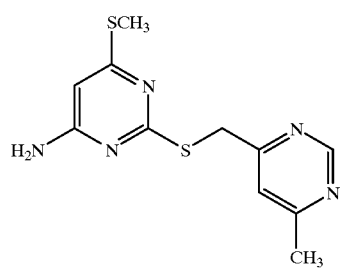
Cpd #131
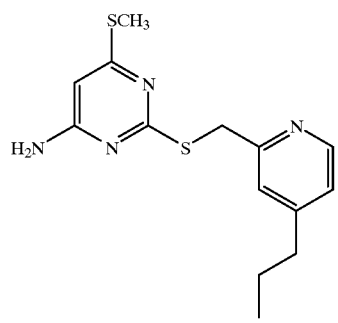
Cpd #132
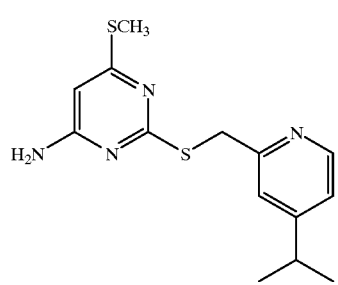
Cpd #133
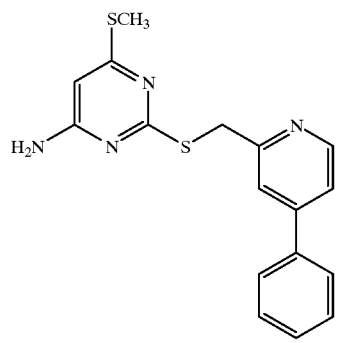
Cpd #134
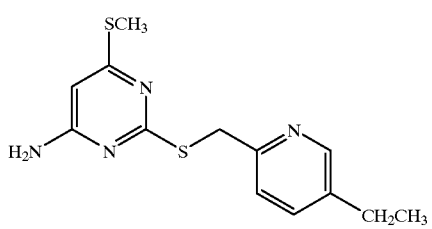
Cpd #135
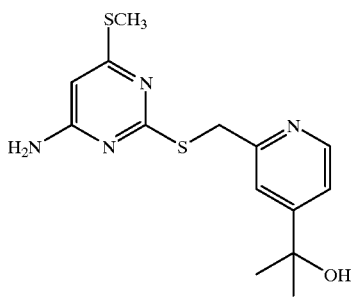
Cpd #137
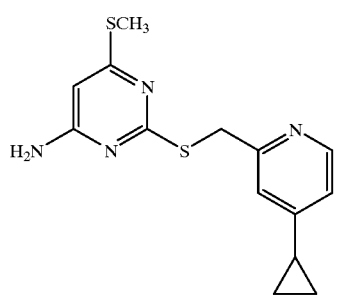
Cpd #138
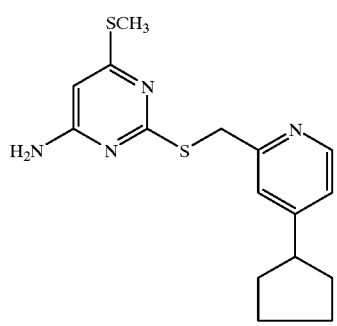
Cpd #140
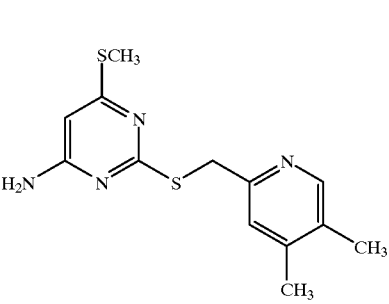
Cpd #142
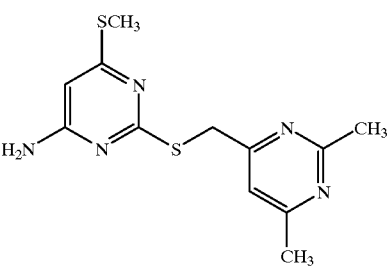

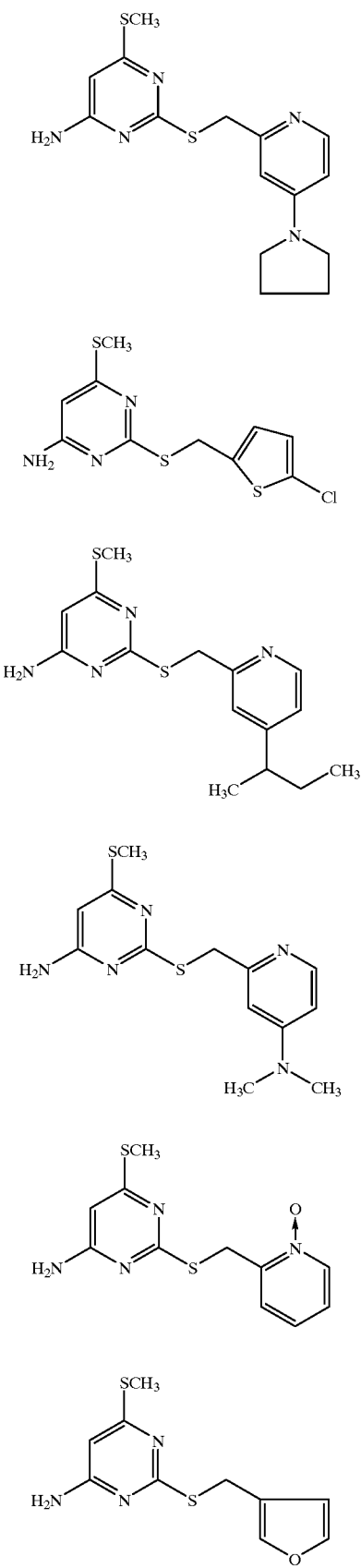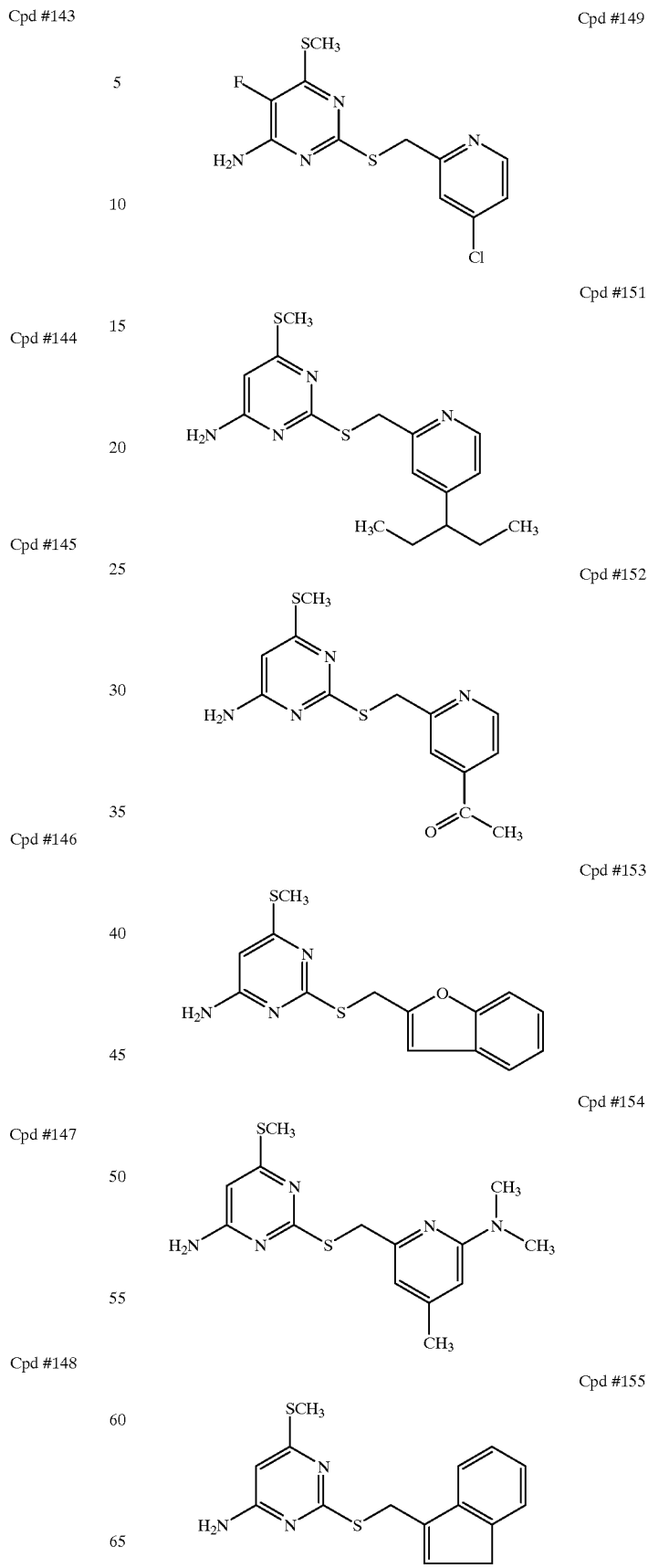

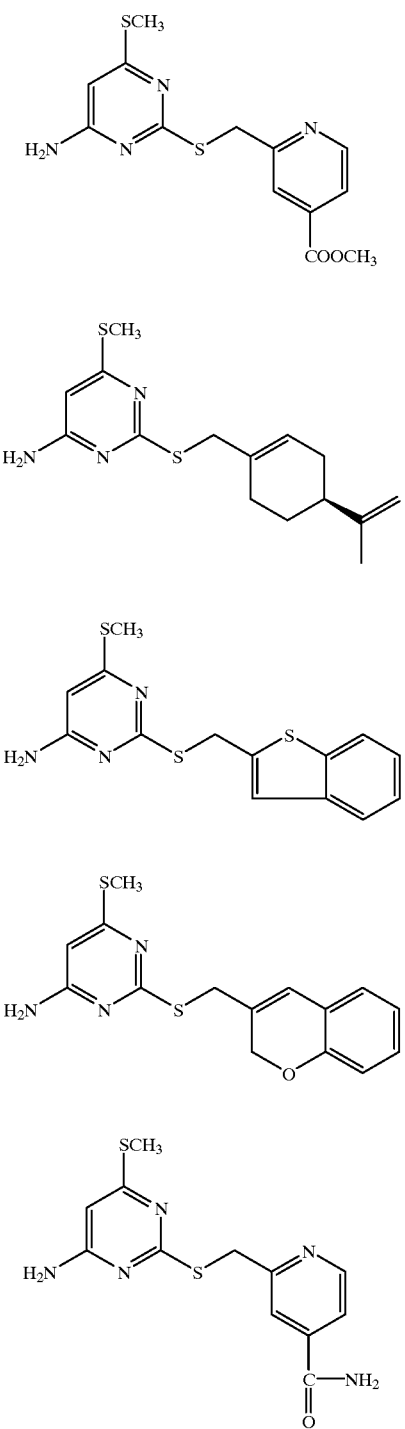
Cpd #156
Cpd #157
Cpd #158
Cpd #159
Cpd #163
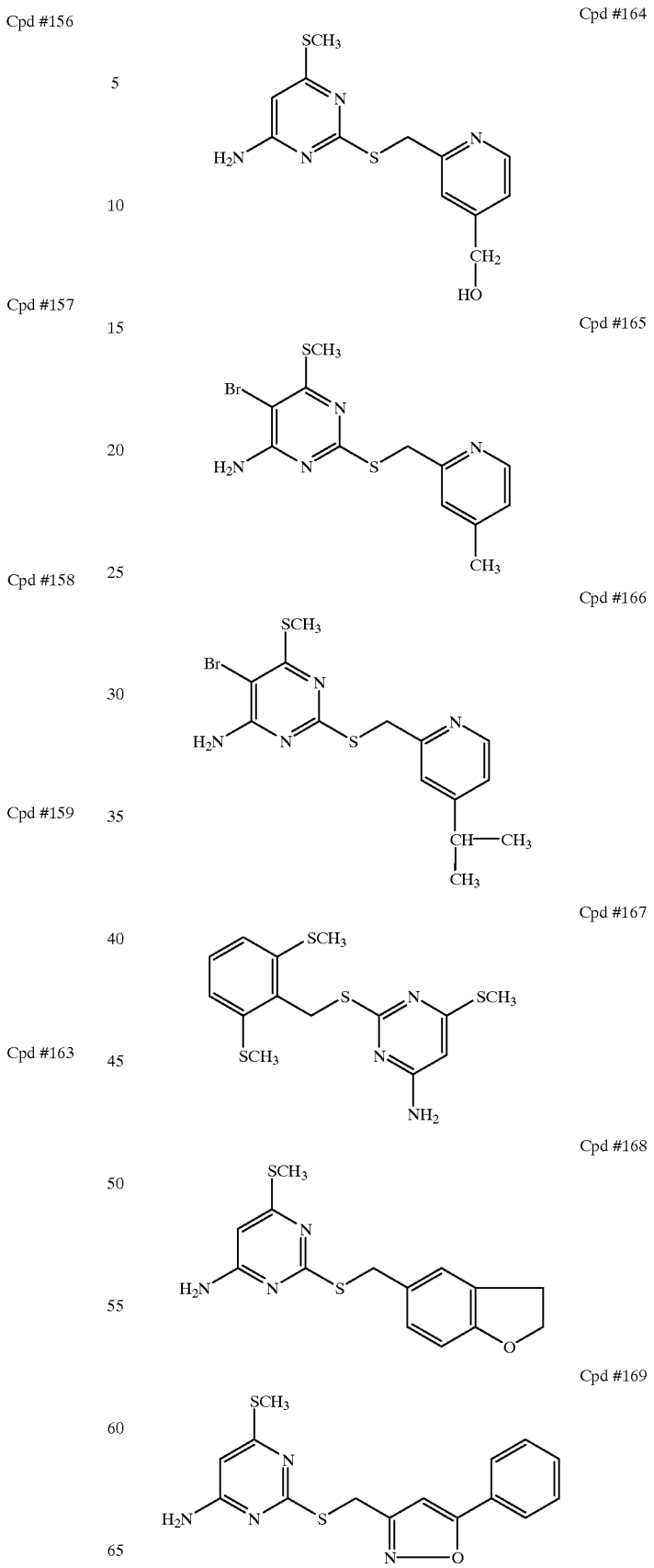
Cpd #164
Cpd #165
Cpd #166
Cpd #167
Cpd #168
Cpd #169

51
-continued
Cpd #170
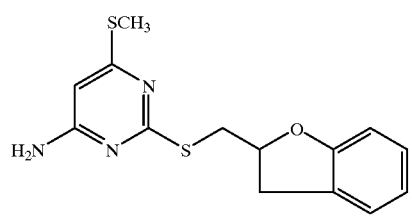
Cpd #171
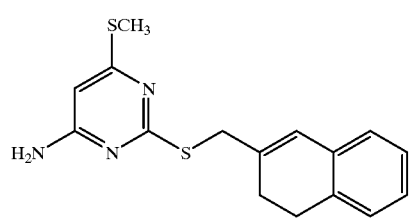
Cpd #172
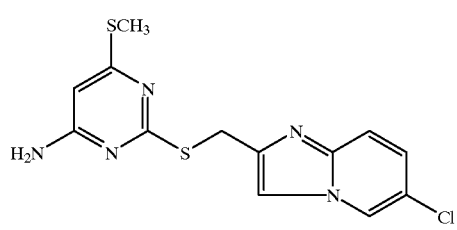
Cpd #173
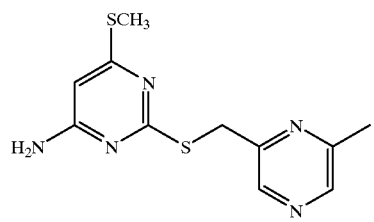
Cpd #174
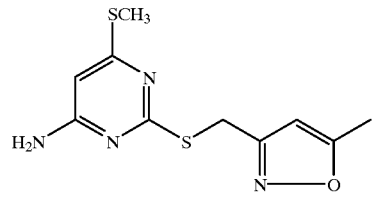
Cpd #175
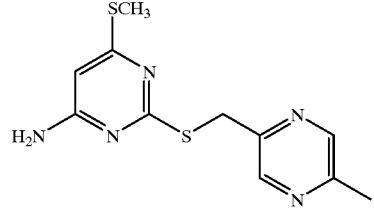
Cpd #176
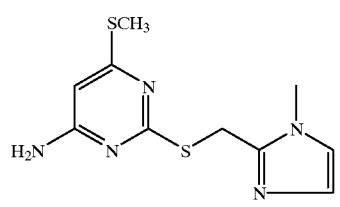
52
-continued
Cpd #177
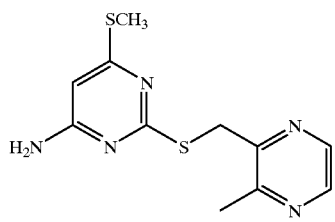
Cpd #178
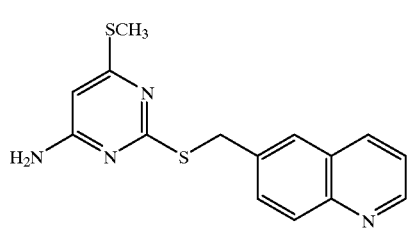
Cpd #179
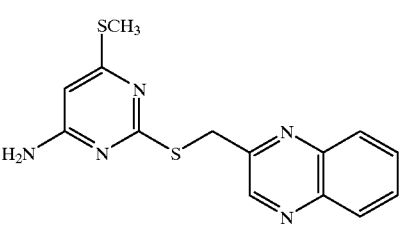
Cpd #180
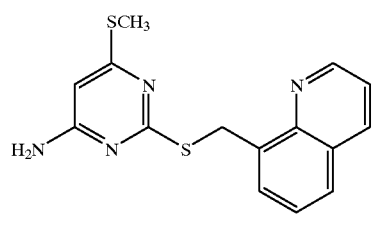
Cpd #181
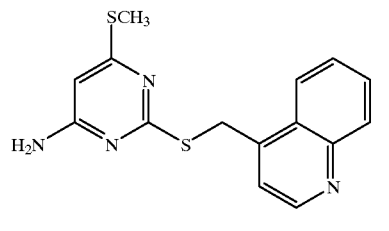
Cpd #182

Cpd #183
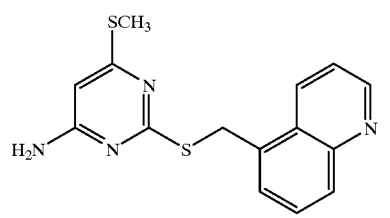
Cpd #184
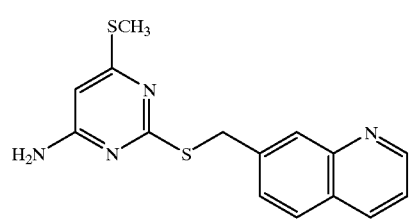
Cpd #186
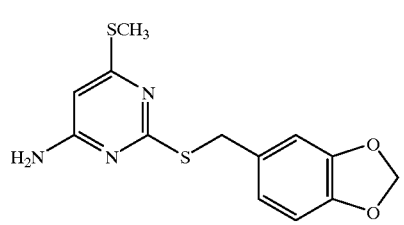
Cpd #187
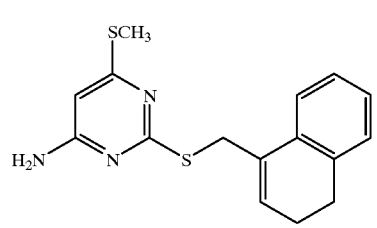
Cpd #188
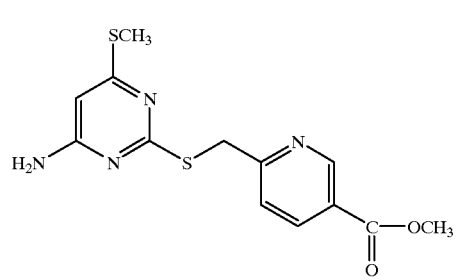
Cpd #189
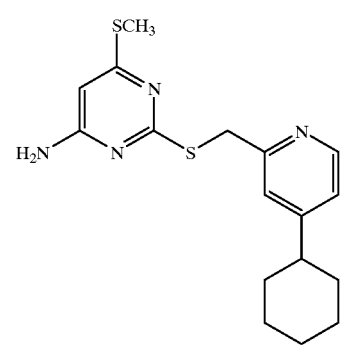
Cpd #191
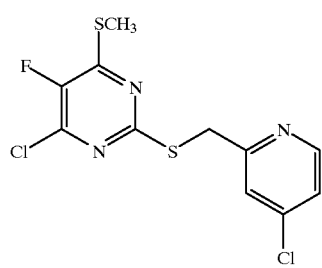
Cpd #192
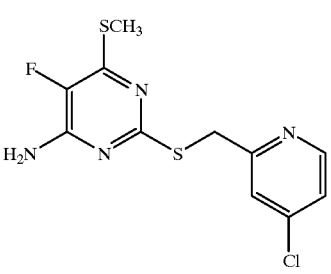
CPD #193
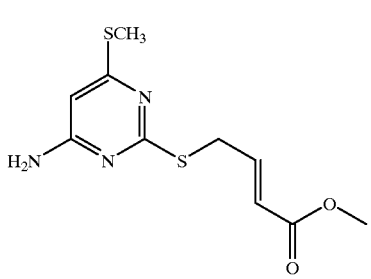
Cpd #194
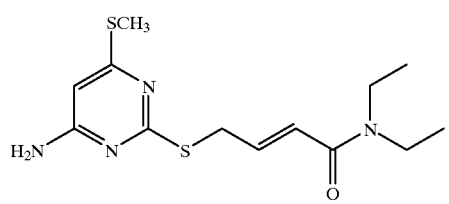
Cpd #195
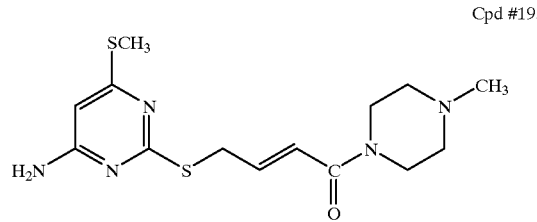
Cpd #196
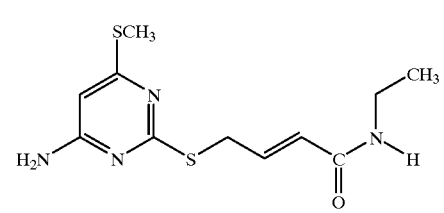

Cpd #197
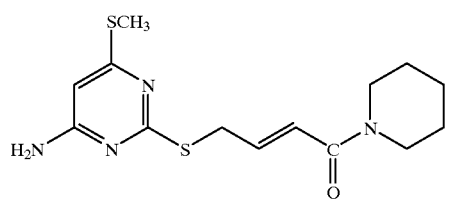
Cpd #198
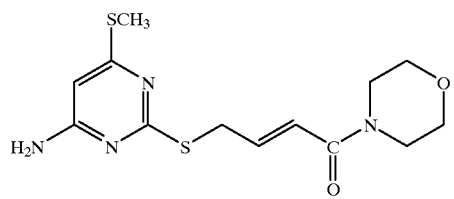
Cpd 199
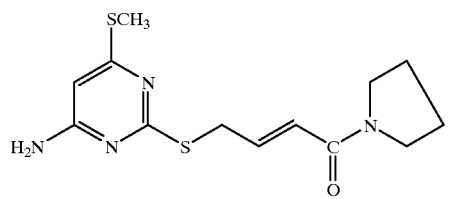
Cpd #200
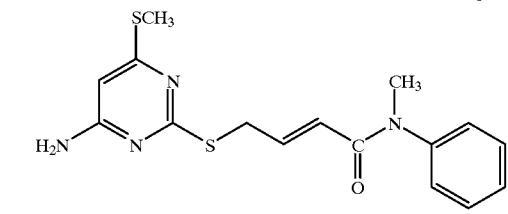
Cpd #201
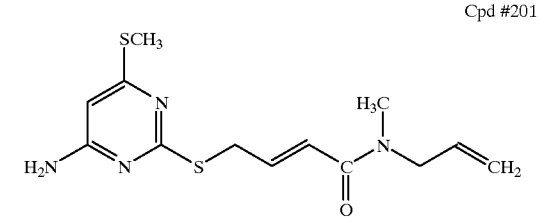
Cpd #202
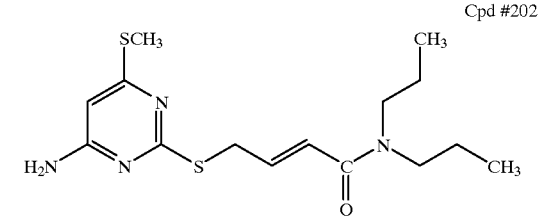
Cpd #203
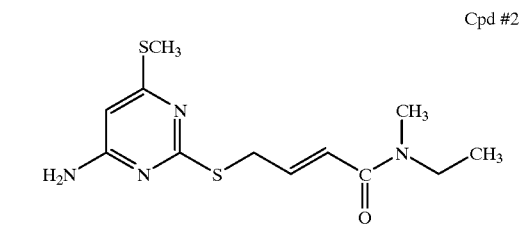
Cpd #204
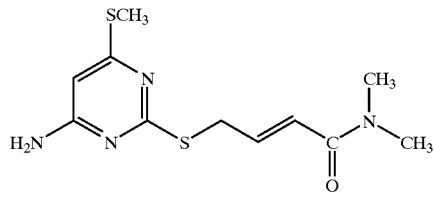
Cpd #207
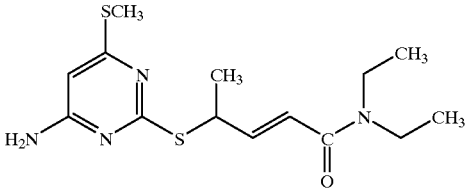
Cpd #208
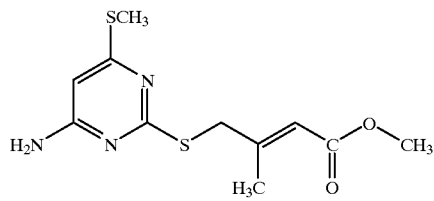
Cpd #209
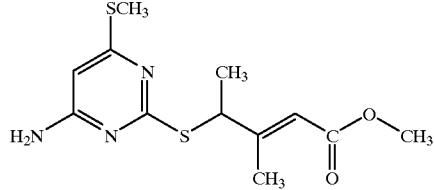
Cpd #210
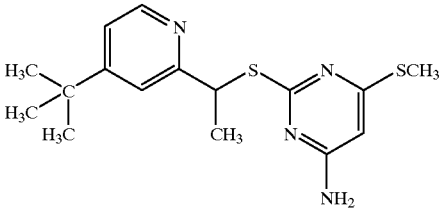
Cpd #211
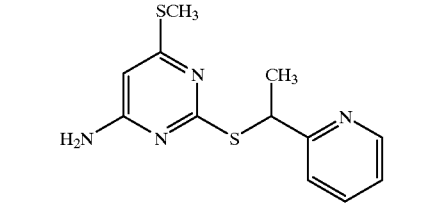
Cpd #212
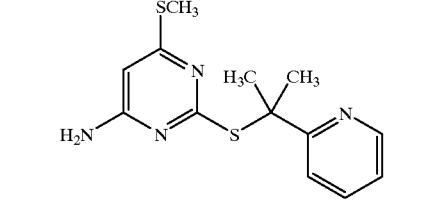

Cpd #213
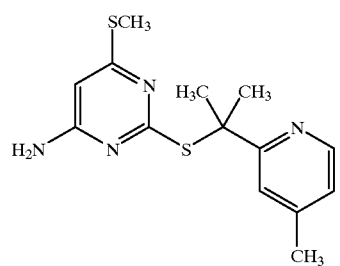
Cpd #214
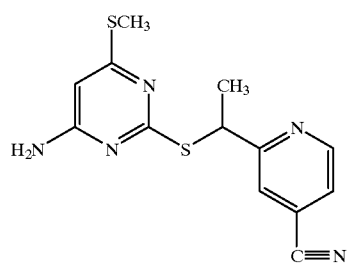
Cpd #215
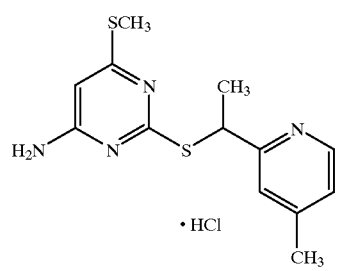
Cpd #216
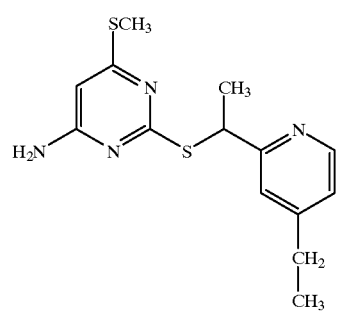
Cpd #217
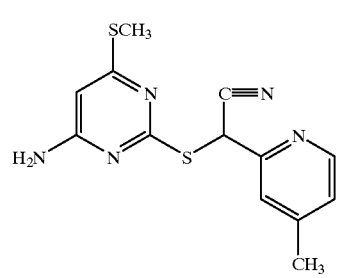
Cpd #218
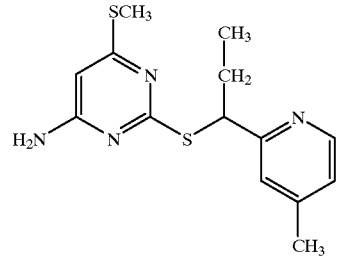
Cpd #219
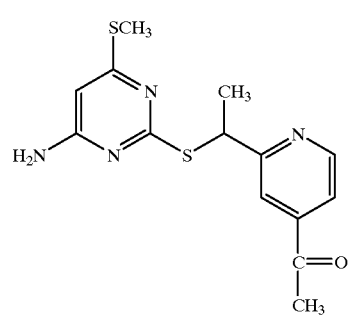
Cpd #220
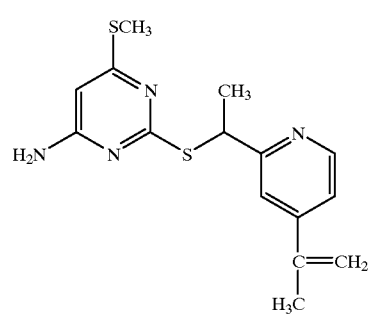
Cpd #221
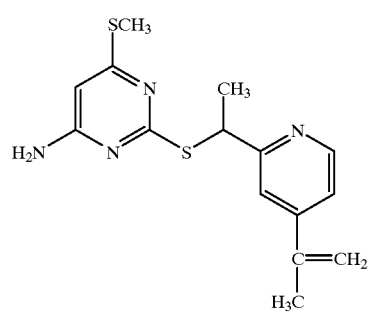
Cpd #223
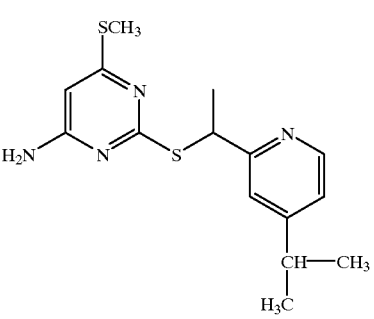

Cpd #224
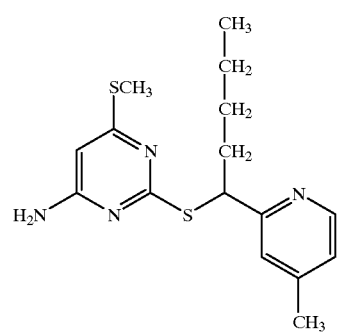
Cpd #225
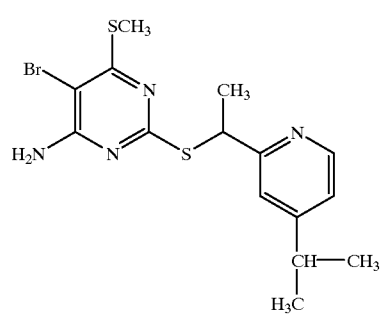
Cpd #226
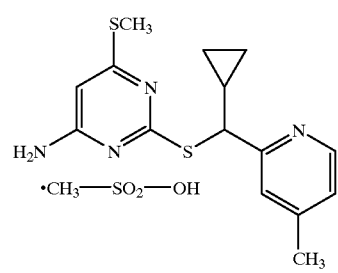
Cpd #227
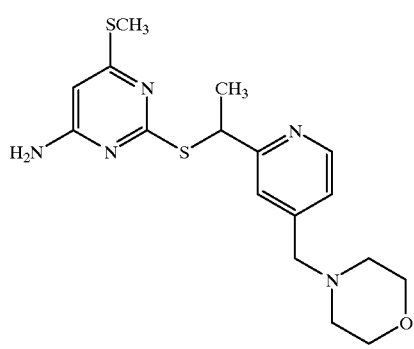
Cpd #228
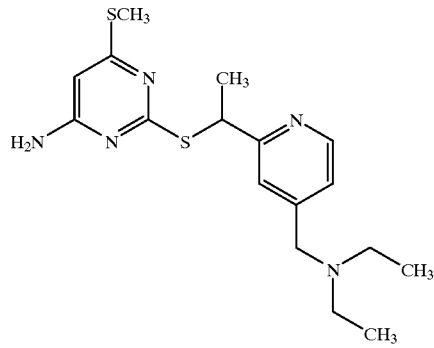
Cpd #229
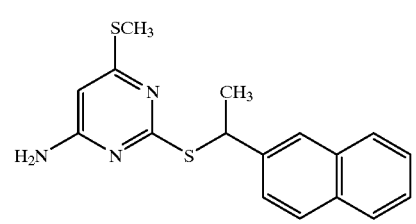
Cpd #230
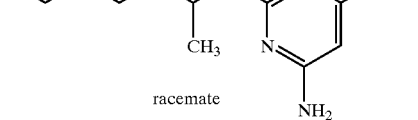
racemate
Cpd #231
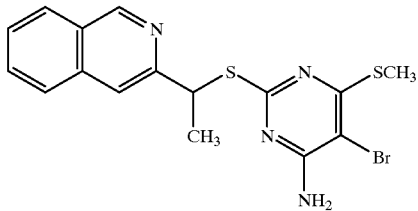
Cpd #232
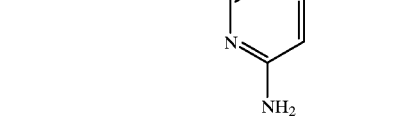
Cpd #233
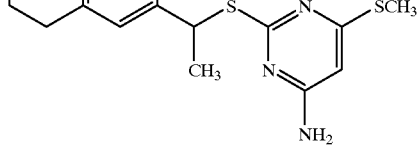

Cpd #235
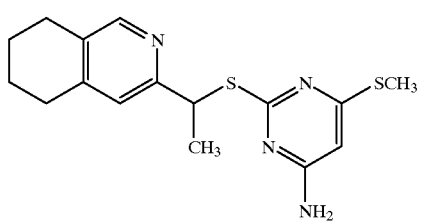
Cpd #237
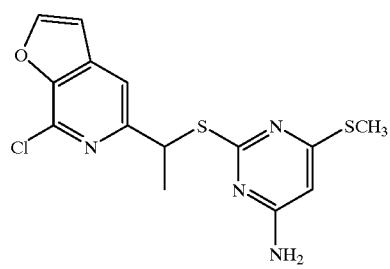
Cpd #238
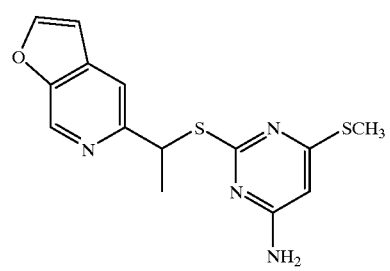
Cpd #240
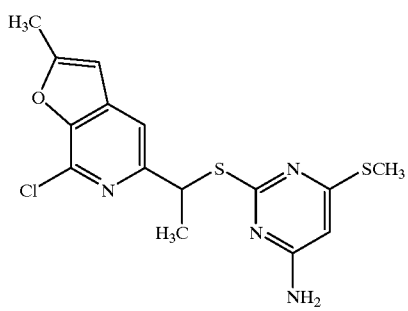
Cpd #242
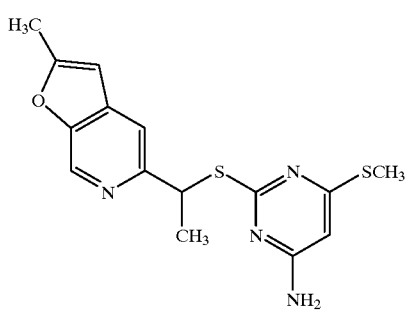
Cpd #244
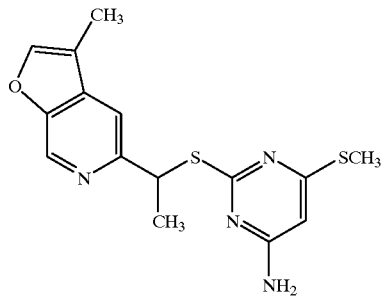
Cpd #245
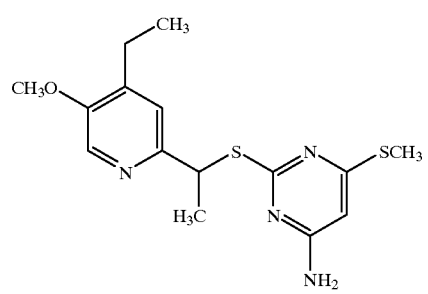
Cpd #246
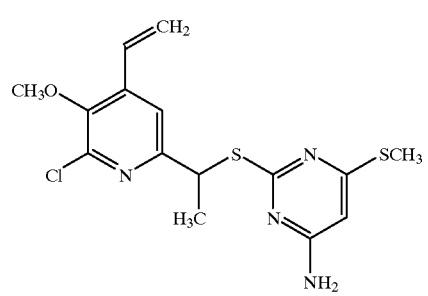
Cpd #247
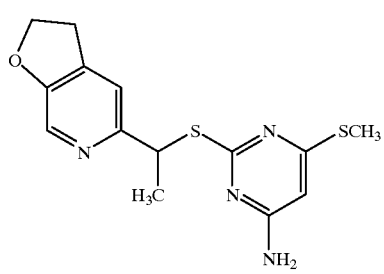
Cpd #248
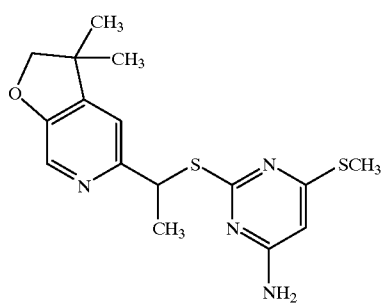

Cpd #249
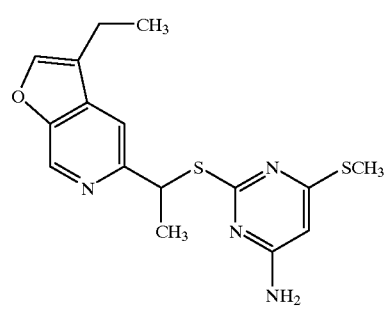
Cpd #250
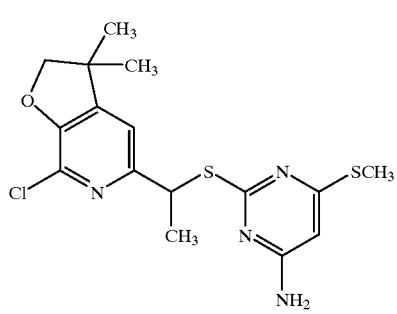
Cpd #251
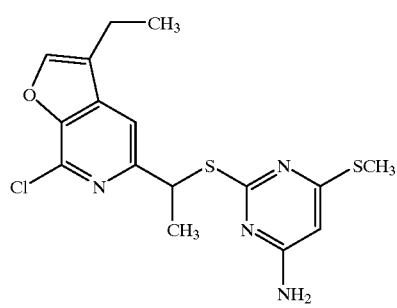
Cpd #252
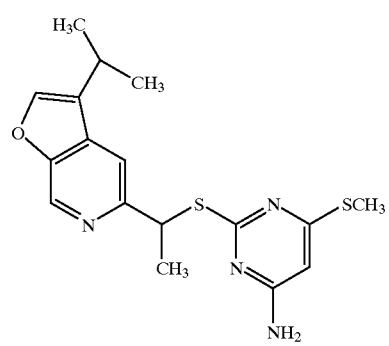
Cpd #253
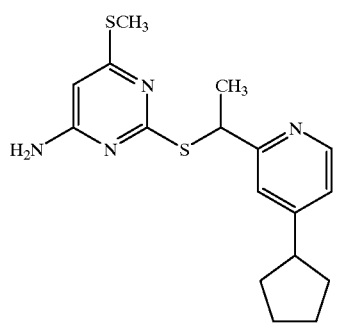
Cpd #255
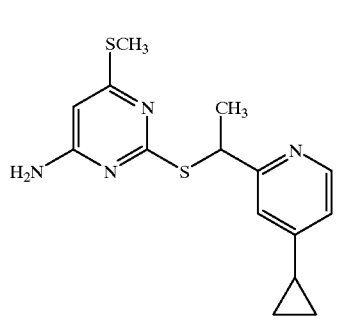
Cpd #256
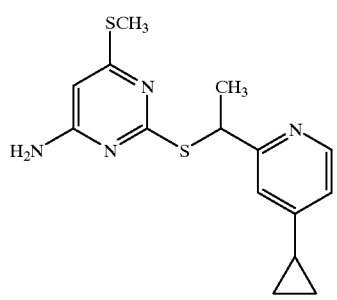
cpd #257
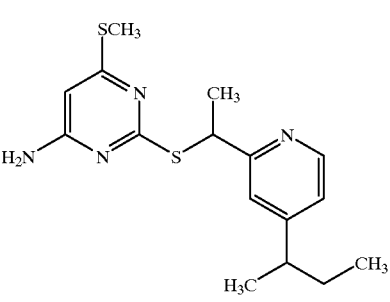

cpd #258
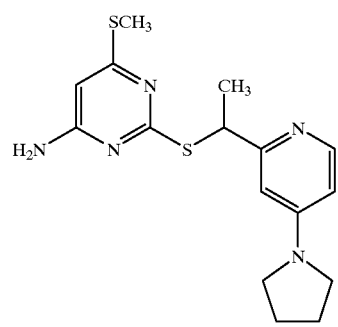
Cpd #259
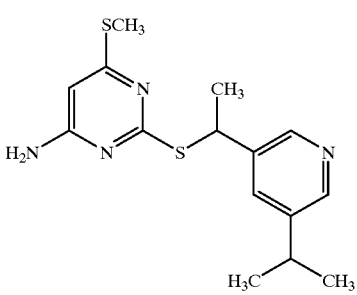
Cpd #260
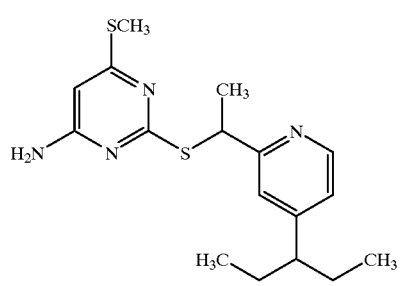
Cpd #261
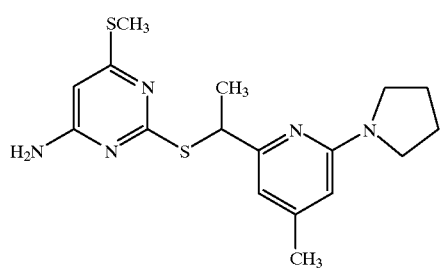
Cpd #262
Cpd #263
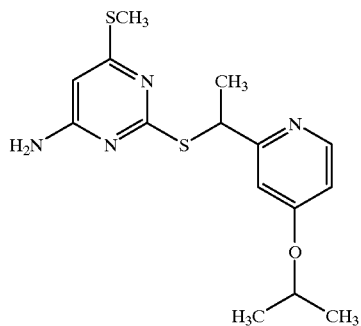
Cpd #282
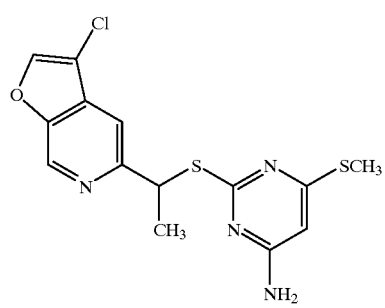
Cpd #283
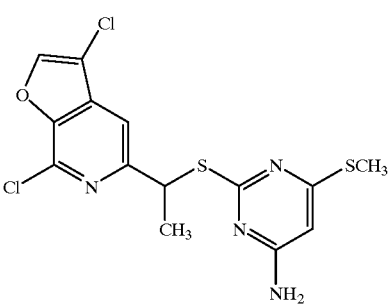
Cpd #284
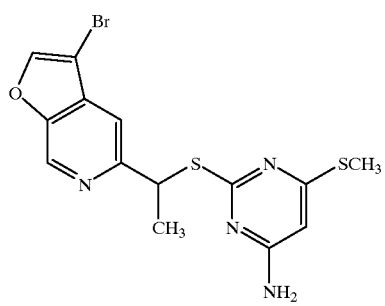
Cpd #285
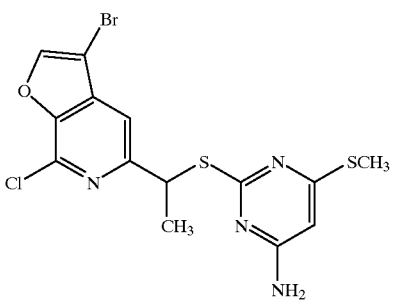

Cpd #286
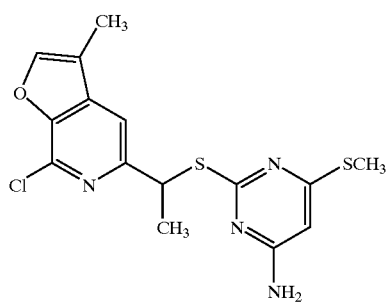
Cpd #289
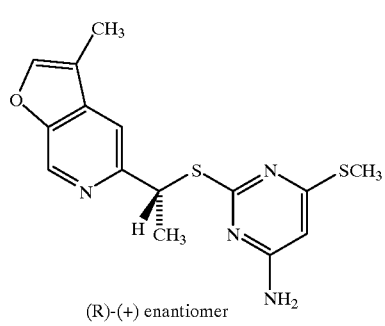
(R)-(+) enantiomer
Cpd #290
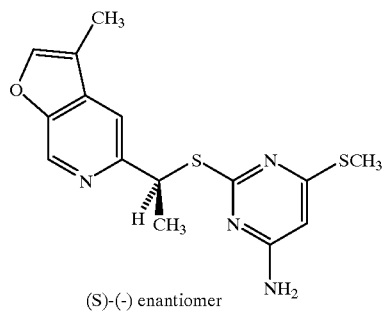
(S)-(-) enantiomer
Cpd #291
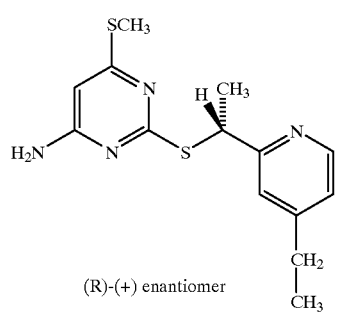
(R)-(+) enantiomer
Cpd #292
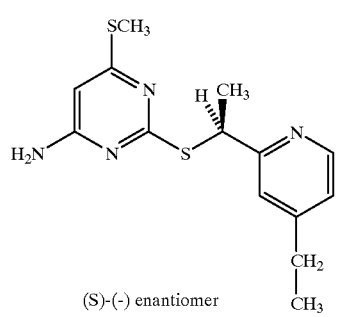
(S)-(-) enantiomer
Cpd #293
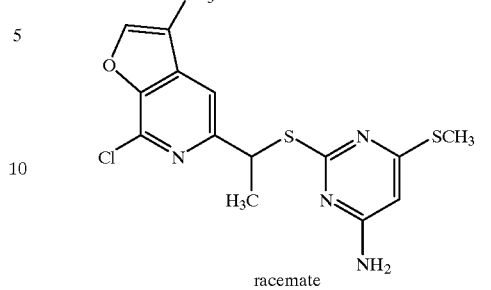
racemate
Cpd #294
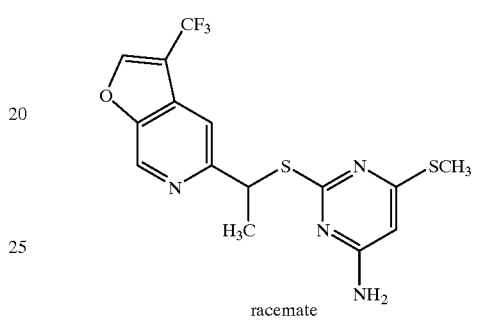
racemate
Cpd #300
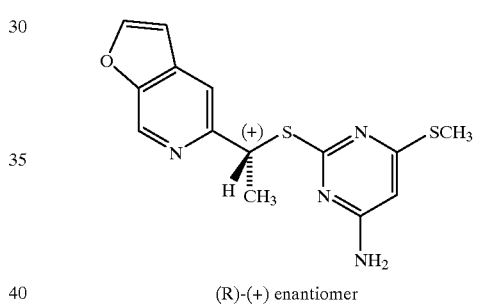
(R)-(+) enantiomer
Cpd #301
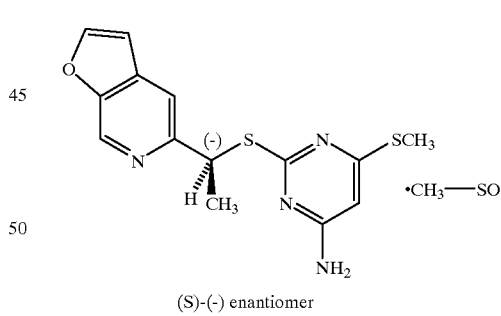
(S)-(-) enantiomer
Cpd #302
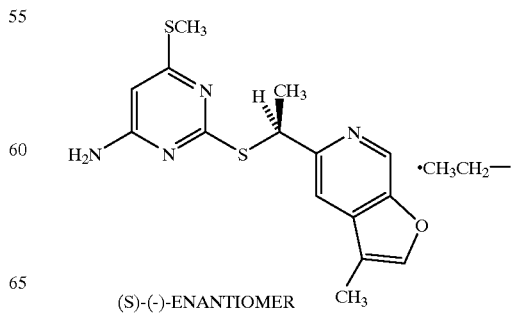
(S)-(-)-ENANTIOMER -continued Cpd #303

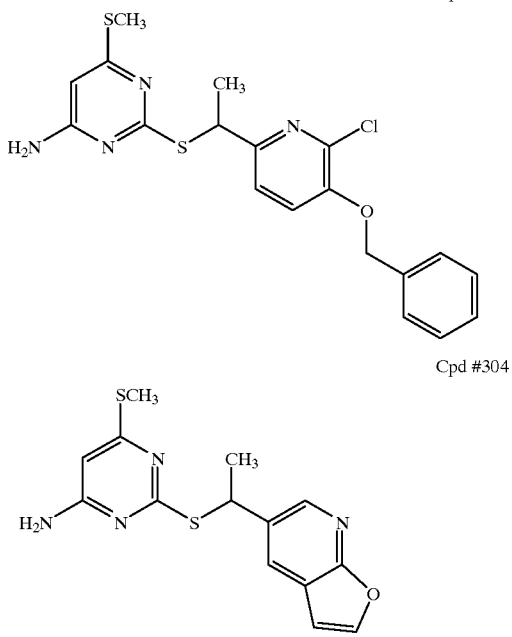

Cpd #304

What is claimed is:
1. A compound of Formula I

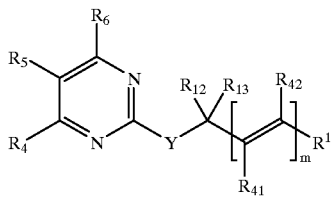

where m is 0 or 1;
$R^1$ is selected from the group consisting of —C≡CH, —$CO_2R_{53}$, —$CONR_{54}R_{55}$,

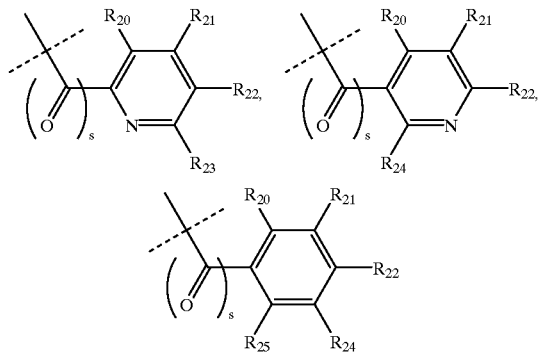

where s is 0 or 1 and $R_{20}$, $R_{21}$, $R_{22}$, $R_{23}$, $R_{24}$, and $R_{25}$ are the same or different and are selected from —H, $C_1$–$C_6$ alkyl, $C_1$–$C_6$ alkenyl, $C_1$–$C_6$ alkoxy, $C_1$–$C_6$ alkylthio, —$C_3$–$C_8$ cycloalkyl, —$CF_3$, —$NO_2$, -halo, —OH, —CN, phenyl, phenylthio, -styryl, —$CO_2(R_{31})$, —$CON(R_{31})(R_{32})$, —$CO(R_{31})$, —$(CH_2)_n$—$N(R_{31})$ $(R_{32})$, —$C(OH)(R_{31})(R_{33})$, —$(CH_2)_nN(R_{31})(CO(R_{33}))$, $(CH_2)_nN(R_{31})(SO_2(R_{33}))$, or where $R_{20}$ and $R_{21}$, or $R_{21}$ and $R_{22}$, or $R_{22}$ and $R_{23}$ are taken together to form a five or six-membered saturated or unsaturated ring containing 0 or 1 oxygen, nitrogen or sulfur, where the unsaturated ring may be optionally substituted with 1, 2 or 3, $C_1$–$C_6$ alkyl, $C_1$–$C_6$ alkoxy, —OH, —$CH_2OH$, —$(CH_2)_n$—$N(R_{31})(R_{32})$, —$C_3$–$C_8$ cycloalkyl, —$CF_3$, -halo, —$CO_2(R_{31})$, —$CON(R_{31})(R_{32})$, —$CO(R_{31})$, —$(CH_2)_nN(R_{31})(CO(R_{33}))$, —$(CH_2)_nN(R_{31})(SO_2(R_{33}))$, —CN, —$CH_2CF_3$ or —$CH(CF_3)_2$, or phenyl, and the saturated ring may be optionally substituted with 1, 2 or 3, -$C_1$–$C_6$ alkyl, —$C_1$–$C_6$ alkoxy, —OH, —$CH_2OH$ or —$(CH_2)_n$—N $(R_{31})(R_{32})$ or one oxo (=O);

where n is 0–3 and $R_{31}$, $R_{32}$, and $R_{33}$ are the same or different and are selected from
—H,
$C_1$–$C_6$ alkyl,
phenyl optionally substituted with 1, 2, or 3-halo, $C_1$–$C_6$ alkyl, $C_1$–$C_6$ alkoxy, —$CF_3$, —OH or —CN,
or where $R_{31}$ and $R_{32}$ taken together with the attached nitrogen to form a ring selected from -pyrrolidinyl, -piperidinyl, -4-morpholinyl, -4-thiomorpholinyl, -4-piperazinyl, -4-(1-$C_1$–$C_6$alkyl)piperazinyl,
or a member selected from the group consisting of:
1-cyclohexenyl, 2-pyrimidinyl, 4-pyrimidinyl, 5-pyrimidinyl, 2-imidazolyl, 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 1-methylimidazol-2-yl, quinoxalin-2-yl, piperon-5-yl, 4,7-dichlorobenzoxazol-2-yl, 4,6-dimethyl-pyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S-4-isopropenylcyclohexen-1-yl or 4-dihydronaphth-2-yl;
where $R_{53}$ is selected from the group consisting of —H, $C_1$–$C_6$ alkyl, $C_3$–$C_6$ cycloalkyl, phenyl (optionally substituted with 1, 2, or 3-halo, $C_1$–$C_6$ alkyl, $C_1$–$C_6$ alkoxy, —$CF_3$, —OH, —CN), or a five or six-membered unsaturated ring containing 0 or 1 oxygen, nitrogen or sulfur, where the unsaturated ring may be optionally substituted with —H, $C_1$–$C_6$ alkyl, $C_1$–$C_6$ alkoxy, —OH, —$CH_2OH$, or —$(CH_2)_n$—$N(R_{31})$ $(R_{32})$;
where $R_{54}$ and $R_{55}$ being the same or different are selected from —H, $C_1$–$C_6$ alkyl, allyl, or phenyl (optionally substituted with 1, 2, or 3-halo, $C_1$–$C_6$ alkyl, $C_1$–$C_6$ alkoxy or —$CF_3$), or taken together with the attached nitrogen to form a ring selected from -pyrrolidinyl, -piperidinyl, -4-morpholinyl, -4-thiomorpholinyl, -4-piperazinyl, -4-(1-$C_1$–$C_6$ alkyl)piperazinyl;
$R_{41}$ and $R_{42}$, being the same or different, are selected from the group consisting of —H and $C_1$–$C_4$ alkyl;
$R_{12}$ is selected from the group consisting of —H, $C_1$–$C_6$ alkyl, —$C_3$–$C_6$ cycloalkyl, —CN, —$C(O)NH_2$, —$C(O)N(C_1$–$C_6$alkyl)($C_1$–$C_6$alkyl), —$CO_2H$, —$CO_2$ ($C_1$–$C_6$alkyl), —$CH_2OH$, —$CH_2NH_2$ or —$CF_3$;
$R_{13}$ is selected from the group consisting of —H, $C_1$–$C_6$ alkyl or —$CF_3$;
Y is selected from —S—, —S(O)—, —$S(O)_2$, or —O—;

$R_4$ is selected from the group consisting of —H, —OH, halo or —$NR_{15}R_{16}$ where $R_{15}$ is —H and $R_{16}$ is —H, $C_1$–$C_6$ alkyl, —$NH_2$ or $R_{15}$ and $R_{16}$ taken together with the —N form 1-pyrrolidino, 4-morpholino or 1-piperidino;

$R_5$ is selected from the group consisting of —H, —$C_2H_4OH$, —$C_2H_4$—O-TBDMS, halo, —$C_3$–$C_6$ cycloalkyl, $C_1$–$C_4$ alkyl or $C_1$–$C_3$ alkoxy;

or $R_4$ and $R_5$ are taken together to form a five or six-membered saturated or unsaturated ring which together with the pyrimidine ring form the group consisting of 7H-pyrrolo[2,3-d]pyrimidine, 5,6-dihydro-7H-pyrrolo[2,3-d]pyrimidine, furo[2,3-d]pyrimidine, 5,6-dihydro-furo[2,3-d]pyrimidine, thieno[2,3-d]pyrimidine, 5,6-dihydro-thieno[2,3-d]pyrimidine, 1H-pyrazolo[3,4-d]pyrimidine, 1H-purine, pyrimido[4,5-d]pyrimidine, pteridine, pyrido[2,3-d]pyrimidine, or quinazoline, where the unsaturated ring may be optionally substituted with 1, 2 or 3, $C_1$–$C_6$ alkyl, $C_1$–$C_6$ alkoxy, —OH, —$CH_2OH$, or —$(CH_2)_n$—$N(R_{31})(R_{32})$, —$C_3$–$C_8$ cycloalkyl, —$CF_3$, -halo, —$CO_2(R_{31})$, —$CON(R_{31})(R_{32})$, —$CO(R_{31})$, —$(CH_2)_nN(R_{31})(CO R_{33})$), —$(CH_2)_nN(R_{31})(SO_2(R_{33}))$, and the saturated ring may be optionally substituted with 1, 2 or 3, —$C_1$–$C_6$ alkyl, —$C_1$–$C_6$ alkoxy, —OH, —$CH_2OH$, or —$(CH_2)_n$—$N(R_{31})(R_{32})$ or one oxo (=O); and $R_6$ is —S—$C_{1-6}$ alkyl; or pharmaceutically acceptable salts, hydrates, N-oxides thereof.

2. A compound according to claim 1 where m is 0, s is 0 and Y is —S.

3. A compound according to claim 2 where $R_{12}$ is $CH_3$ and $R_{13}$ is —H.

4. A compound according to claim 3 where $R_4$ is $NH_2$, $R_5$ is —H, and $R_6$ is $SCH_3$.

5. A compound according to claim 3 where $R_1$ is

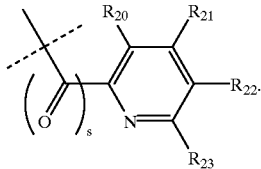

6. A compound according to claim 5 wherein $R_4$ is $NH_2$, $R_5$ is —H, and $R_6$ is —$SCH_3$.

7. A compound according to claim 3 wherein $R_1$ is a five or six membered saturated or unsaturated ring selected from the group consisting of 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyrindinyl, 1-(5,6-dihydro)-2H-2-pyrindinyl, 2-(5,6-dihydro)-1H-1-pyrindinyl, 3-(5,6-dihydro)-1H-1-pyrindinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl, 5-1H-pyrrolo[2,3-c]pyridinyl, 6-1H-pyrrolo[3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2,3-dihydro)-1H-pyrrolo[3,2-c]pyridinyl, 7-(2,3-dihydro)-1H-pyrrolo[2,3-c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3,4-b]pyridinyl, 6-1,7-naphthyridinyl, 6-2,7-naphthyridinyl, 7-2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)-benzofuranyl, 7-(2,3-dihydro)-benzofuranyl, 4-(1,3-dihydro)-isobenzofuran, 5-(1,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3-dihydro)-1H-indolyl, 6-(2,3-dihydro)-1H-indolyl, 7-(2,3-dihydro)-1H-indolyl, 4-(1,3-dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1-benzopyranyl, 7-(3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl, 5-thieno[2,3-c]pyridinyl, 6-thieno[3,2-c]pyridinyl, 4-thieno[3,2-c]pyridinyl, 7-thieno[2,3-c]pyridinyl, 6-thieno[2,3-b]pyridinyl, 5-thieno[3,2-b]pyridinyl, 5-(2,3-dihydro)-thieno[2,3-c]pyridinyl, 6-(2,3-dihydro)-thieno[3,2-c]pyridinyl, 4-(2,3-dihydro)-thieno[3,2-c]pyridinyl, 7-(2,3-dihydro)-thieno[2,3-c]pyridinyl, 6-(2,3-dihydro)-thieno[2,3-b]pyridinyl, 5-(2,3-dihydro)-thieno[3,2-b]pyridinyl, 6-(1,3-dihydro)-thieno[3,4-c]pyridinyl, 4-(1,3-dihydro)-thieno[3,4-c]pyridinyl, 2-(5,7-dihydro)-thieno[3,4-b]pyridinyl, 6-(3,4-dihydro)-2H-thiopyrano[2,3-c]pyridinyl, 6-(3,4-dihydro)-1H-thiopyrano[3,4-c]pyridinyl, 7-(3,4-dihydro)-1H-thiopyrano[4,3-c]pyridinyl, 7-(3,4-dihydro)-2H-thiopyrano[3,2-c]pyridinyl, 5-(3,4-dihydro)-2H-thiopyrano[3,2-c]pyridinyl, 5-(3,4-dihydro)-1H-thiopyrano[4,3-c]pyridinyl, 8-(3,4-dihydro)-1H-thiopyrano[3,4-c]pyridinyl, 8-(3,4-dihydro)-2H-thiopyrano[2,3-c]

pyridinyl, 7-(3,4-dihydro)-2H-thiopyrano[2,3-b]pyridinyl, 2-(5,6-dihydro)-1H-thiopyrano[3,4-b]pyridinyl, 2-(5,6-dihydro)-2H-thiopyrano[4,3-b]pyridinyl, 6-(3,4-dihydro)-2H-thiopyrano[3,2-b]pyridinyl, 5-benzo[b]thiophenyl, 4-benzo[b]thiophenyl, 6-benzo[b]thiophenyl, 7-benzo[b]thiophenyl, 5-(2,3-dihydro)-benzo[b]thiophenyl, 4-(2,3-dihydro)-benzo[b]thiophenyl, 6-(2,3-dihydro)-benzo[b]thiophenyl, 7-(2,3-dihydro)-benzo[b]thiophenyl, 4-(1,3-dihydro)-benzo[c]thiophenyl, 5-(1,3-dihydro)-benzo[c]thiophenyl, 5-(3,4-dihydro)-1H-2-benzothiopyranyl, 6-(3,4-dihydro)-1H-2-benzothiopyranyl, 7-(3,4-dihydro)-1H-2-benzothiopyranyl, 8-(3,4-dihydro)-1H-2-benzothiopyranyl, 5-(3,4-dihydro)-2H-1-benzothiopyranyl, 6-(3,4-dihydro)-2H-1-benzothiopyranyl, 7-(3,4-dihydro)-2H-1-benzothiopyranyl, or 8-(3,4-dihydro)-2H-1-benzothiopyranyl; or such five or six membered ring substituted with 1, 2 or 3, $C_1$–$C_6$ alkyl, $C_1$–$C_6$ alkoxy, —OH, —CH$_2$OH, (CH$_2$)$_n$—N(R$_{31}$)(R$_{32}$), —$C_3$–$C_8$ cycloalkyl, —CF$_3$, -halo, —CO$_2$(R$_{31}$), —CON(R$_{31}$)(R$_{32}$), —CO(R$_{31}$), —(CH$_2$)$_n$N(R$_{31}$)(CO(R$_{33}$)), —(CH$_2$)$_n$N(R$_{31}$)(SO$_2$(R$_{33}$)), —CN, —CH$_2$CF$_3$ or —CH(CF$_3$)$_2$, or phenyl, and the saturated ring may be optionally substituted with 1, 2 or 3, —$C_1$–$C_6$ alkyl, —$C_1$–$C_6$ alkoxy, —OH, —CH$_2$OH or (CH$_2$)$_n$—N(R$_{31}$)(R$_{32}$) or one oxo (=O).

8. A compound according to claim 7 wherein R$_4$ is NH$_2$, R$_5$ is —H, and R$_6$ is —SCH$_3$.

9. A compound according to claim 8 wherein R$_1$ is a five or six membered saturated or unsaturated ring selected from the group consisting of 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyrindinyl, 1-(5,6-dihydro)-2H-2-pyrindinyl, 2-(5,6-dihydro)-1H-1-pyrindinyl, 3-(5,6-dihydro)-1H-1-pyrindinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl and 6-(3,4-dihydro)-2H-pyrano[3,2-b]pyridinyl or such five or six membered ring substituted 1, 2 or 3, $C_1$–$C_6$ alkyl, $C_1$–$C_6$ alkoxy, —OH, —CH$_2$OH, —(CH$_2$)$_n$—N(R$_{31}$)(R$_{32}$), —$C_3$–$C_8$ cycloalkyl, —CF$_3$, -halo, —CO$_2$(R$_{31}$), —CON(R$_{31}$)(R$_{32}$), —CO(R$_{31}$), —(CH$_2$)$_n$N(R$_{31}$)(CO(R$_{33}$)), —(CH$_2$)$_n$N(R$_{31}$)(SO$_2$(R$_{33}$)), —CN, —CH$_2$CF$_3$ or CH(CF$_3$)$_2$, or phenyl, and the saturated ring may be optionally substituted with 1, 2 or 3, —$C_1$–$C_6$ alkyl, —$C_1$–$C_6$ alkoxy, —OH, —CH$_2$OH or —(CH$_2$)$_n$—N(R$_{31}$)(R$_{32}$) or one oxo (=O).

10. A compound according to claim 1 and selected from the group consisting of:

(E)-N,N-Diethyl-4-[(4-amino-6-methylthio-2-pyrimidinyl)thiol-2-butenamide (Cpd#194)

(E)-1-[4-[(4-amino-6-methylthio-2-pyrimidinyl)thio]-1-oxo-2-butenyl]pyrrolidine (Cpd#199)

(E)-N-ethyl-N-methyl-4-[(4-amino-6-methylthio-2-pyrimidinyl)thio]-2-butenamide (Cpd#203)

(E)-N,N-Diethyl-4-[(4-amino-6-methylthio-2-pyrimidinyl)thio]-2-pentenamide (Cpd#207)

4-Amino-6-methylthio-2-(1-(3-isoquinolyl)ethyl)thio-pyrimidine (Cpd#230)

4-Amino-5-bromo-6-methylthio-2-(1-(3-isoquinolyl)ethyl)thio-pyrimidine (Cpd #231)

4-Amino-6-methylthio-2-(1-(3-(5,6,7,8-tetrahydroisoquinolyl))ethyl)thio-pyrimidine (Cpd#233)

4-Amino-6-methylthio-2-(1-(7-chlorofuro[2,3c]pyridine-5-yl)ethyl)thio-pyrimidine (Cpd#237)

4-Amino-6-methylthio-2-(1-(furo[2,3-c]pyridin-5-yl)ethyl)thio-pyrimidine (Cpd#238)

4-Amino-6-methylthio-2-(1-(7-chloro-2-methylfuro[2,3c]pyridine-5-yl)ethyl)thio-pyrimidine (Cpd #240)

4-Amino-6-methylthio-2-(1-(2-methylfuro[2,3c]pyridine-5-yl)ethyl)thio-pyrimidine (Cpd #242)

4-Amino-6-methylthio-2-(1-(2-methylfuro[2,3c]pyridine-5-yl)ethyl)thio-pyrimidine (Cpd #243)

4-Amino-6-methylthio-2-(1-(3-methylfuro[2,3c]pyridine-5-yl)ethyl)thio-pyrimidine (Cpd #246)

4-Amino-6-methylthio-2-(1-(2,3-dihydrofuro[2,3c]pyridine-5-yl)ethyl)thio-pyrimidine (Cpd #247)

4-Amino-6-methylthio-2-(1-(3,3-dimethyl-2,3-dihydrofuro[2,3c]pyridine-5-yl)ethyl)thio-pyrimidine (Cpd #248)

4-Amino-6-methylthio-2-(1-(3-ethylfuro[2,3c]pyridine-5-yl)ethyl)thio-pyrimidine (Cpd #249)

4-Amino-6-methylthio-2-(1-(7-chloro-3,3-dimethyl-2,3-dihydrofuro[2,3c]pyridine-5-yl)ethyl)thio-pyrimidine (Cpd #250)

4-Amino-6-methylthio-$^2$-(1-(7-chloro-3-ethylfuro-[2,3c]pyridine-5-yl)ethyl)thio-pyrimidine (Cpd #251)

4-Amino-6-methylthio-$^2$-(1-(3-(1-methylethyl)furo[2,3c]-pyridin-5-yl)ethyl)thio-pyrimidine (Cpd #252)

4-Amino-6-methylthio-$^2$-(1-(3-chlorofuro[2,3c]pyridine-5-yl)ethyl)thio-pyrimidine (Cpd #282)

4-Amino-6-methylthio-2-(1-(3,7-dichlorofuro[2,3c]pyridine-5-yl)ethyl)thio-pyrimidine, (Cpd #283)

4-Amino-6-methylthio-$^2$-(1-(3-bromofuro[2,3c]pyridine-5-yl)ethyl)thio-pyrimidine, (Cpd #284)

4-Amino-6-methylthio-$^2$-(1-(3-bromo-7-chlorofuro[2,3c]pyridine-5-yl)ethyl)thio-pyrimidine, (Cpd #285)

4-Amino-6-methylthio-$^2$-(1-(7-chloro-3-methylfuro[2,3c]pyridine-5-yl)ethyl)thio-pyrimidine, (Cpd #286)

4-Amino-6-trifluoromethyl-2-(1-(7-chloro-3,3-dimethyl-2,3-dihydrofuro[2,3c]pyridine-5-yl)ethyl)thio-pyrimidine, (Cpd #287)

(R)-(+)-4-Amino-6-methylthio-2-(1-(3-methylfuro[2,3c]pyridine-5-yl)ethyl)thio-pyrimidine (Cd #289)

(S)-(−)-4-Amino-6-methylthio-2-(1-(3-methylfuro[2,3c]pyridine-5-yl)ethyl)thio-pyrimidine Cpd #290

(S)-(−)-4-Amino-6-trifluoromethyl-2-(1-(3methylfuro[2,3c]pyridin-5-yl)ethylthio)-pyrimidine (Cpd #297)

(S)-(−)-4-Amino-6-methylthio-2-(1-(furo[2,3c]pyridin-5-yl)ethylthio)-pyrimidine (Cpd #1);

and pharmaceutically acceptable salts, hydrates, and N-oxides thereof.

11. A method of treating an individual infected with the human immunodeficiency virus (HIV) which comprises administering an effective amount of an anti-AIDS compound of Formula I

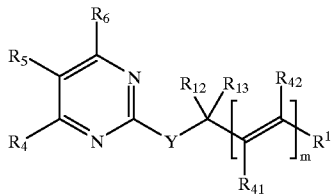

where m is 0 or 1,
R¹ is selected from the group consisting of —C≡CH, —CO₂R₅₃, —CONR₅₄R₅₅,

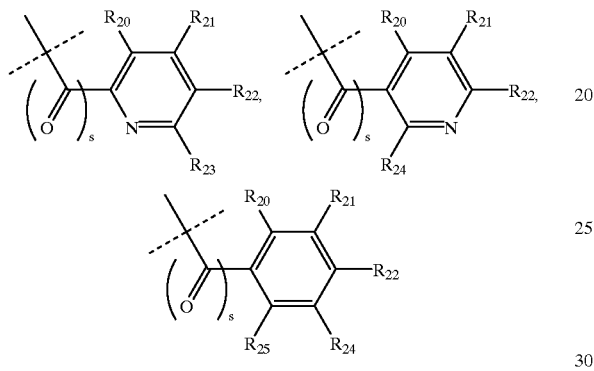

where s is 0 or 1 and $R_{20}$, $R_{21}$, $R_{22}$, $R_{23}$, $R_{24}$, and $R_{25}$ are the same or different and are selected from —H, $C_1$–$C_6$ alkyl, $C_1$–$C_6$ alkenyl, $C_1$–$C_6$ alkoxy, $C_1$–$C_6$ alkylthio, —$C_3$–$C_8$ cycloalkyl, —$CF_3$, —$NO_2$, -halo, —OH, —CN, phenyl, phenylthio, -styryl, —$CO_2(R_{31})$, —$CON(R_{31})(R_{32})$, —$CO(R_{31})$, —($CH_2$), —$N(R_{31})(R_{32})$, —$C(OH)(R_{31})(R_{33})$, —$(CH_2)_nN(R_{31})(CO(R_{33}))$, $(CH_2)_nN(R_{31})(SO_2 (R_{33}))$, or where $R_{20}$ and $R_{21}$, or $R_{21}$ and $R_{22}$, or $R_{22}$ and $R_{23}$ are taken together to form a five or six-membered saturated or unsaturated ring containing 0 or 1 oxygen, nitrogen or sulfur, where the unsaturated ring may be optionally substituted with 1, 2 or 3, $C_1$–$C_6$ alkyl, $C_1$–$C_6$ alkoxy, —OH, —$CH_2OH$, —$(CH_2)_nN(R_{31})(R_{32})$, —$C_3$–$C_8$ cycloalkyl, —$CF_3$, -halo, —$CO_2(R_{31})$, —$CON(R_{31})(R_{32})$, —$CO(R_{31})$, —$(CH_2)_nN(R_{31})(CO(R_{33}))$, —$(CH_2)_nN(R_{31})(SO_2(R_{33}))$, —CN, $CH_2CF_3$ or —$CH(CF_3)_2$, or phenyl, and the saturated ring may be optionally substituted with 1, 2 or 3, —$C_1$–$C_6$ alkyl, —$C_1$–$C_6$ alkoxy, —OH, —$CH_2OH$ or —$(CH_2)_n$—N $(R_{31})(R_{32})$ or one oxo (=O);
where n is 0–3 and $R_{31}$, $R_{32}$, and $R_{33}$ are the same or different and are selected from
—H,
$C_1$–$C_6$ alkyl,
phenyl optionally substituted with 1, 2, or 3-halo, $C_1$–$C_6$ alkyl, $C_1$–$C_6$ alkoxy, —$CF_3$, —OH or —CN,
or where $R_{31}$ and $R_{32}$ taken together with the attached nitrogen to form a ring selected from -pyrrolidinyl, -piperidinyl, -4-morpholinyl, -4-thiomorpholinyl, -4-piperazinyl, -4-(1-$C_1$–$C_6$alkyl)piperazinyl,
or a member selected from the group consisting of:
1-cyclohexenyl, 2-pyrimidinyl, 4-pyrimidinyl, 5-pyrimidinyl, 2-imidazolyl, 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 1-methylimidazol-2-yl, quinoxalin-2-yl, piperon-5-yl, 4,7-dichlorobenzoxazol-2-yl, 4,6-dimethyl-pyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S-4-isopropenylcyclohexen-1-yl or 4-dihydronaphth-2-yl; where $R_{53}$ is selected from the group consisting of —H, $C_1$–$C_6$alkyl, $C_3$–$C_6$cycloalkyl, phenyl (optionally substituted with 1, 2, or 3-halo, $C_1$–$C_6$ alkyl, $C_1$–$C_6$ alkoxy, —$CF_3$, —OH, —CN), or a five or six-membered unsaturated ring containing 0 or 1 oxygen, nitrogen or sulfur, where the unsaturated ring may be optionally substituted with —H, $C_1$–$C_6$ alkyl, $C_1$–$C_6$ alkoxy, —OH, —$CH_2OH$, or —$(CH_2)_n$—$N(R_{31})(R_{32})$;
where $R_{54}$ and $R_{55}$ being the same or different are selected from —H, $C_1$–$C_6$ alkyl, allyl, or phenyl (optionally substituted with 1, 2, or 3-halo, $C_1$–$C_6$ alkyl, $C_1$–$C_6$ alkoxy or —$CF_3$), or taken together with the attached nitrogen to form a ring selected from -pyrrolidinyl, -piperidinyl, -4-morpholinyl, -4-thiomorpholinyl, -4-piperazinyl, -4-(1-$C_1$–$C_6$alkyl)piperazinyl;
$R_{41}$ and $R_{42}$, being the same or different, are selected from the group consisting of —H and $C_1$–$C_4$ alkyl;
$R_{12}$ is selected from the group consisting of —H, $C_1$–$C_6$ alkyl, —$C_3$–$C_6$ cycloalkyl, —CN, —$C(O)NH_2$, —$C(O)N(C_1$–$C_6$alkyl)($C_1$–$C_6$alkyl), —$CO_2H$, —$CO_2$ ($C_1$–$C_6$alkyl), —$CH_2OH$, —$CH_2NH_2$ or —$CF_3$;
$R_{13}$ is selected from the group consisting of —H, $C_1$–$C_6$ alkyl or —$CF_3$;
Y is selected from —S—, —S(O)—, —S(O)₂, or —O—,
$R_4$ is selected from the group consisting of —H, —OH, halo or —$NR_{15}R_{16}$ where $R_{15}$ is —H and $R_{16}$ is —H, $C_1$–$C_6$ alkyl, —$NH_2$ or $R_{15}$ and $R_{16}$ taken together with the —N form 1-pyrrolidino, 4-morpholino or 1-piperidino;
$R_5$ is selected from the group consisting of —H, —$C_2H_4OH$, —$C_2H_4$—O-TBDMS, halo, —$C_3$–$C_6$ cycloalkyl, $C_1$–$C_4$ alkyl or $C_1$–$C_3$ alkoxy;
or $R_4$ and $R_5$ are taken together to form a five or six-membered saturated or unsaturated ring which together with the pyrimidine ring form the group consisting of 7H-pyrrolo[2,3-d]pyrimidine, 5,6-dihydro-7H-pyrrolo[2,3-d]pyrimidine, furo[2,3-d]pyrimidine, 5,6-dihydro-furo[2,3-d]pyrimidine, thieno[2,3-d]pyrimidine, 5,6-dihydro-thieno[2,3-d]pyrimidine, 1H-pyrazolo [3,4-d]pyrimidine, 1H-purine, pyrimido [4,5-d]pyrimidine, pteridine, pyrido[2,3-d]pyrimidine, or quinazoline, where the unsaturated ring may be optionally substituted with 1, 2 or 3, $C_1$–$C_6$ alkyl, $C_1$–$C_6$ alkoxy, —OH, —$CH_2OH$, or $(CH_2)_n$—$N(R_{31})(R_{32})$, —$C_3$–$C_8$ cycloalkyl, —$CF_3$, -halo, —$CO_2(R_{31})$, —$CON(R_{31})(R_{32})$, —$CO(R_{31})$, $(CH_2)_nN(R_{31})(CO(R_{33}))$, $(CH_2)_nN(R_{31})$ $(SO_2(R_{33}))$, and the saturated ring may be optionally substituted with 1, 2 or 3, —$C_1$–$C_6$ alkyl, —$C_1$–$C_6$ alkoxy, —OH, —$CH_2OH$, or —$(CH_2)_n$—$N(R_{31})(R_{32})$ or one oxo (=O); and
$R_6$ is —S—$C_1$–$C_6$ alkyl;
and pharmaceutically acceptable salts, hydrates, N-oxides thereof.

12. A method according to claim 11 where m is 0, s is 0 and Y—S.

13. A method according to claim 12 where $R_{12}$ is $CH_3$ and $R_{13}$ is —H.

14. A method according to claim 13 where $R_4$ is $NH_2$, $R_5$ is —H, and $R_6$ is —$SCH_3$.

15. A method according to claim 12 where $R_1$ is

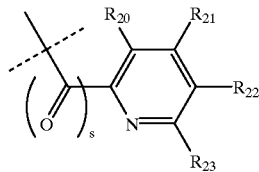

16. A method according to claim 15 wherein $R_4$ is $NH_2$, $R_5$ is —H, and $R_6$ is —$SCH_3$.

17. A method according to claim 14 wherein $R_1$ is a five or six membered saturated or unsaturated ring selected from the group consisting of 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyrindinyl, 1-(5,6-dihydro)-2H-2-pyrindinyl, 2-(5,6-dihydro)-1H-1-pyrindinyl, 3-(5,6-dihydro)-1H-1-pyrindinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl, 5-1H-pyrrolo[2,3-c]pyridinyl, 6-1H-pyrrolo[3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2,3-dihydro)-1H-pyrrolo[3,2-c]pyridinyl, 7-(2,3-dihydro)-1H-pyrrolo[2,3-c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3,4-b]pyridinyl, 6-1,7-naphthyridinyl, 6-2,7-naphthyridinyl, 7-2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)-benzofuranyl, 7-(2,3-dihydro)-benzofuranyl, 4-(1,3-dihydro)-isobenzofuran, 5-(1,3-dihydro)-isobenzofuran, 4-1H-indolyl, 5-1H-indolyl, 3-1H-indolyl, 7-1H-indolyl, 4-(2,3-dihydro)-1H-indolyl, 5-(2,3-dihydro)-1H-indolyl, 6-(2,3-dihydro)-1H-indolyl, 7-(2,3-dihydro)-1H-indolyl, 4-(1,3-dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1-benzopyranyl, 7-(3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl, 5-thieno[2,3-c]pyridinyl, 6-thieno[3,2-c]pyridinyl, 4-thieno[3,2-c]pyridinyl, 7-thieno[2,3-c]pyridinyl, 6-thieno[2,3-b]pyridinyl, 5-thieno[3,2-b]pyridinyl, 5-(2,3-dihydro)-thieno[2,3-c]pyridinyl, 6-(2,3-dihydro)-thieno[3,2-c]pyridinyl, 4-(2,3-dihydro)-thieno[3,2-c]pyridinyl, 7-(2,3-dihydro)-thieno[2,3-c]pyridinyl, 6-(2,3-dihydro)-thieno[2,3-b]pyridinyl, 5-(2,3-dihydro)-thieno[3,2-b]pyridinyl, 6-(1,3-dihydro)-thieno[3,4-c]pyridinyl, 4-(2,3-dihydro)-thieno[3,4-c]pyridinyl, 2-(5,7-dihydro)-thieno[3,4-b]pyridinyl, 6-(3,4-dihydro)-2H-thiopyrano[2,3-c]pyridinyl, 6-(3,4-dihydro)-1H-thiopyrano[3,4-c]pyridinyl, 7-(3,4-dihydro)-1H-thiopyrano[4,3-c]pyridinyl, 7-(3,4-dihydro)-2H-thiopyrano[3,2-c]pyridinyl, 5-(3,4-dihydro)-2H-thiopyrano[3,2-c]pyridinyl, 5-(3,4-dihydro)-1H-thiopyrano[4,3-c]pyridinyl, 8-(3,4-dihydro)-1H-thiopyrano[3,4-c]pyridinyl, 8-(3,4-dihydro)-2H-thiopyrano[2,3-c]pyridinyl, 7-(3,4-dihydro)-2H-thiopyrano[2,3-b]pyridinyl, 2-(5,6-dihydro)-1H-thiopyrano[3,4-b]pyridinyl, 2-(5,6-dihydro)-2H-thiopyrano[4,3-b]pyridinyl, 6-(3,4-dihydro)-2H-thiopyrano[3,2-b]pyridinyl, 5-benzo[b]thiophenyl, 4-benzo[b]thiophenyl, 6-benzo[b]thiophenyl, 7-benzo[b]thiophenyl, 5-(2,3-dihydro)-benzo[b]thiophenyl, 4-(2,3-dihydro)-benzo[b]thiophenyl, 6-(2,3-dihydro)-benzo[b]thiophenyl, 7-(2,3-dihydro)-benzo[b]thiophenyl, 4-(1,3-dihydro)-benzo[c]thiophenyl, 5-(1,3-dihydro)-benzo[c]thiophenyl, 5-(3,4-dihydro)-1H-2-benzothiopyranyl, 6-(3,4-dihydro)-1H-2-benzothiopyranyl, 7-(3,4-dihydro)-1H-2-benzothiopyranyl, 8-(3,4-dihydro)-1H-2-benzothiopyranyl, 5-(3,4-dihydro)-2H-1-benzothiopyranyl, 6-(3,4-dihydro)-2H-1-benzothiopyranyl, 7-(3,4-dihydro)-2H-1-benzothiopyranyl or 8-(3,4-dihydro)-2H-1-benzothiopyranyl; or such five or six membered ring substituted with 1, 2 or 3, $C_1$–$C_6$ alkyl, $C_1$–$C_6$ alkoxy, —OH, —$CH_2OH$, —$(CH_2)_n$—$N(R_{31})(R_{32})$, —$C_3$–$C_8$ cycloalkyl, —$CF_3$, -halo, —$CO_2(R_{31})$, —$CON(R_{31})(R_{32})$, —$CO(R_{31})$, —$(CH_2)_nN(R_{31})(CO(R_{33}))$, —$(CH_2)_nN(R_{31})(SO_2(R_{33}))$, —CN, —$CH_2CF_3$ or —$CH(CF_3)_2$, or phenyl, and the saturated ring may be optionally substituted with 1, 2 or 3, —$C_1$–$C_6$ alkyl, —$C_1$–$C_6$ alkoxy, —OH, —$CH_2OH$ or —$(CH_2)_n$—$N(R_{31})(R_{32})$ or one oxo (=O).

18. A method according to claim 17 wherein $R_4$ is $NH_2$, $R_5$ is —H, and $R_6$ is —$SCH_3$.

19. A method according to claim 18 wherein $R_1$ is a five or six membered saturated or unsaturated ring selected from the group consisting of 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyrindinyl, 1-(5,6-dihydro)-2H-2-pyrindinyl, 2-(5,6-dihydro)-1H-1-pyrindinyl, 3-(5,6-dihydro)-1H-1-pyrindinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl and 6-(3,4-dihydro)-2H-pyrano[3,2-b]pyridinyl or such five or six membered ring with 1, 2 or 3, $C_1$–$C_6$ alkyl, $C_1$–$C_6$ alkoxy, —OH, —$CH_2OH$, —$(CH_2)_n$—$N(R_{31})(R_{32})$, —$C_3$–$C_8$ cycloalkyl, —$CF_3$, -halo, —$CO_2(R_{31})$, —CON$(R_{31})(R_{32})$, CO($R_{31}$), —$(CH_2)_nN(R_{31})(CO(R_{33}))$, —$(CH_2)_nN(R_{31})(SO_2(R_{33}))$, —CN, —$CH_2CF_3$ or —$CH(CF_3)_2$, or phenyl, and the saturated ring may be optionally substituted with 1, 2 or 3, —$C_1$–$C_6$ alkyl, —$C_1$–$C_6$ alkoxy, —OH, —$CH_2OH$ or —$(CH_2)_n$—$N(R_{31})(R_{32})$ or one oxo (=O).

20. A method of treating an individual infected with the human immunodeficiency virus (HIV) according to claim 11 where the (1) infected individual is asymptomatic but tests positive for the HIV antigen, (2) infected individual is symptomatically sick but does not have "full blown AIDS", (3) individual infected with the human immunodeficiency virus (HIV) has "full blown AIDS".

21. A method of treating an individual infected with the human immunodeficiency virus (HIV) according to claim 11 where the administration is oral and the effective dose is from about 0.10 mg/kg/day to about 500 mg/kg/day.

22. A method of treating an individual infected with the human immunodeficiency virus (HIV) according to claim 11 where the compound is selected from the group consisting of (E)-N,N-Diethyl-4-[(4-amino-6-methylthio-2-pyrimidinyl)thio]-2-butenamide (Cpd#194)
(E)-1-[4-[(4-amino-6-methylthio-2-pyrimidinyl)thio]-1-oxo-2-butenyl]pyrrolidine (Cpd#199)
(E)-N-ethyl-N-methyl-4-[(4-amino-6-methylthio-2-pyrimidinyl)thio]-2-butenamide (Cpd#203)
(E)-N,N-Diethyl-4-[(4-amino-6-methylthio-2-pyrimidinyl)thio]-2-pentenamide (Cpd#207)
4-Amino-6-methylthio-2-(1-(3-isoquinolyl)ethyl)thio-pyrimidine (Cpd#230)
4-Amino-5-bromo-6-methylthio-2-(1-(3-isoquinolyl)ethyl)thio-pyrimidine (Cpd#231)
4-Amino-6-methylthio-2-(1-(3-(5,6,7,8-tetrahydroisoquinolyl))ethyl)thio-pyrimidine (Cpd#233)
4-Amino-6-trifluoromethyl-2-(1-(3-(5,6,7,8-tetrahydro-isoquinolyl))ethyl)thio-pyrimidine (Cpd#234)
4-Amino-6-methylthio-2-(1-(7-chlorofuro[2,3c]pyridine-5-yl)ethyl)thio-pyrimidine (Cpd#237)
4-Amino-6-methylthio-2-(1-(furo[2,3-c]pyridin-5-yl)ethyl)thio-pyrimidine (Cpd #238)
4-Amino-6-trifluoromethyl-2-(1-(furo[2,3-c]pyridin-5-yl)ethyl)thio-pyrimidine (Cpd#239)
4-Amino-6-methylthio-2-(1-(7-chloro-2-methylfuro[2,3c]pyridine-5-yl)ethyl)thio-pyrimidine (Cpd #240)
4-Amino-6-trifluoromethyl-2-(1-(7-chloro-2-methylfuro[2,3c]pyridine-5-yl)ethyl)thio-pyrimidine (Cpd#241)
4-Amino-6-methylthio-2-(1-(2-methylfuro[2,3c]pyridine-5-yl)ethyl)thio-pyrimidine (Cpd #242)
4-Amino-6-trifluoromethyl-2-(1-(2-methylfuro[2,3c]pyridine-5-yl)ethyl)thio-pyrimidine (Cpd #243)
4-Amino-6-methylthio-2-(1-(3-methylfuro[2,3c]pyridine-5-yl)ethyl)thio-pyrimidine (Cpd #246)
4-Amino-6-methylthio-2-(1-(2,3-dihydrofuro[2,3c]pyridine-5-yl)ethyl)thio-pyrimidine (Cpd #247)
4-Amino-6-methylthio-2-(1-(3,3-dimethyl-2,3-dihydrofuro[2,3c]pyridine-5-yl)ethyl)thio-pyrimidine (Cpd #248)
4-Amino-6-methylthio-2-(1-(3-ethylfuro[2,3c]pyridine-5-yl)ethyl)thio-pyrimidine (Cpd #249)
4-Amino-6-methylthio-2-(1-(7-chloro-3,3-dimethyl-2,3-dihydrofuro[2,3c]pyridine-5-yl)ethyl)thio-pyrimidine (Cpd #250)
4-Amino-6-methylthio-2-(1-(7-chloro-3-ethylfuro-[2,3c]pyridine-5-yl)ethyl)thio-pyrimidine (Cpd #251)
4-Amino-6-methylthio-2-(1-(3-(1-methylethyl)furo[2,3c]-pyridin-5-yl)ethyl)thio-pyrimidine (Cpd #252)
4-amino-6-chloro-2-(1-(4-(1-methylpropyl)-2-pyridyl)-ethyl)thio-pyrimidine (Cpd #256)
4-amino-6-trifluoromethyl-2-(1-(4-(1-dimethylethyl)-2-pyridyl)-ethyl)thio-pyrimidine (Cpd #269)
4-amino-6-trifluoromethyl-2-(2-naphthylmethyl)thio-pyrimidine (Cpd #270)
4-amino-6-trifluoromethyl-2-((4-(1-methylethyl)-2-pyridyl)methyl)thio-pyrimidine (Cpd #271)
4-amino-6-trifluoromethyl-2-(1-(4-(1-methylethyl)-2-pyridyl)ethyl)thio-pyrimidine (Cpd #272)
4-amino-6-trifluoromethyl-2-((4-(1,1-dimethylethyl)-2-pyridyl)methyl)thio-pyrimidine (Cpd #273)
6-amino-2-(2-naphthylmethyl)thio-4-pyrimidine carbonitrile (Cpd 277),
4-Amino-6-methylthio-2-(1-(3-chlorofuro[2,3c]pyridine-5-yl)ethyl)thio-pyrimidine (Cpd #282)
4-Amino-6-methylthio-2-(1-(3,7-dichlorofuro[2,3c]pyridine-5-yl)ethyl)thio-pyrimidine, (Cpd #283)
4-Amino-6-methylthio-2-(1-(3-bromofuro[2,3c]pyridine-5-yl)ethyl)thio-pyrimidine, (Cpd #284)
4-Amino-6-methylthio-2-(1-(3-bromo-7-chlorofuro[2,3c]pyridine-5-yl)ethyl)thio-pyrimidine, (Cpd #285)
4-Amino-6-methylthio-2-(1-(7-chloro-3-methylfuro[2,3c]pyridine-5-yl)ethyl)thio-pyrimidine, (Cpd #286)
4-Amino-6-trifluoromethyl-2-(1-(7-chloro-3,3-dimethyl-2,3-dihydrofuro[2,3c]pyridine-5-yl)ethyl)thio-pyrimidine, (Cpd #287)
(R)-(+)-4-Amino-6-methylthio-2-(1-(3-methylfuro[2,3c]pyridine-5-yl)ethyl)thio-pyrimidine (Cpd #289)
(S)-(−)-4-Amino-6-methylthio-2-(1-(3-methylfuro[2,3c]pyridine-5-yl)ethyl)thio-pyrimidine Cpd (#290)
(S)-(−)-4-Amino-6-trifluoromethyl-2-(1-(3-methylfuro[2,3c]pyridin-5-yl)ethylthio)-pyrimidine (Cpd #297)
(S)-(−)-4-Amino-6-methylthio-2-(1-(furo[2,3c]pyridin-5-yl)ethylthio)-pyrimidine (Cpd #1);
and pharmaceutically acceptable salts, and hydrates thereof.

23. A method according to claim 21 where the compound is selected from the group consisting of (S)-(−)-4-Amino-6-methylthio-2-(1-(3-methylfuro[2,3c]pyridine-5-yl)ethyl)thio-pyrimidine;

- (S)-(−)-4-Amino-6-methylthio-2-(1-(3-methylfuro[2,3c]pyridin-5-yl)ethylthio)-pyrimidine esylate salt;
- (S)-(−)-4-Amino-2-(3-methyl-furano[2,3c]pyridin-5-yl)ethylthio-6-trifluoromethyl-pyrimidine mesylate salt;
- (S)-(−)-4-Amino-6-methylthio-2-(1-(furo[2,3c]pyridin-5-yl)ethylthio)-pyrimidine and
- (S)-(−)-4-Amino-6-methylthio-2-(1-(furo[2,3c]pyridin-5-yl)ethylthio)-pyrimidine mesylate salt.

24. A compound according to claim 1 and selected from the group consisting of

- (S)-(−)-4-Amino-6-methylthio-2-(1-(3-methylfuro[2,3c]pyridine-5-yl)ethyl)thio-pyrimidine;
- (S)-(−)-4-Amino-6-methylthio-2-(1-(3-methylfuro[2,3c]pyridin-5-yl)ethylthio-pyrimidine esylate salt;
- (S)-(−)-4-Amino-6-methylthio-2-(1-(furo[2,3c]pyridin-5-yl)ethylthio)-pyrimidine and
- (S)-(−)-4-Amino-6-methylthio-2-(1-(furo[2,3c]pyridin-5-yl)ethylthio)-pyrimidine mesylate salt.

\* \* \* \* \*